(12) United States Patent
Massimini et al.

(10) Patent No.: US 12,295,654 B2
(45) Date of Patent: May 13, 2025

(54) SYSTEM AND METHOD FOR MAINTAINING BALLOON INTEGRITY WITHIN INTRAVASCULAR LITHOTRIPSY DEVICE WITH PLASMA GENERATOR

(71) Applicants: BOSTON SCIENTIFIC SCIMED, INC., Maple Grove, MN (US); Bolt Medical, Inc., Carlsbad, CA (US)

(72) Inventors: Daniel Frank Massimini, Brooklyn Park, MN (US); Roger W. McGowan, Otsego, MN (US); Jeffrey Steven Fuller, Brooklyn Park, MN (US); Jeffrey S. Lindquist, Maple Grove, MN (US); Dave Parsons, Hanover, MN (US); Eric Schultheis, San Clemente, CA (US)

(73) Assignees: BOSTON SCIENTIFIC SCIMED, INC., Maple Grove, MN (US); BOLT MEDICAL, INC., Carlsbad, CA (US)

( * ) Notice: Subject to any disclaimer, the term of this patent is extended or adjusted under 35 U.S.C. 154(b) by 388 days.

(21) Appl. No.: 17/335,820

(22) Filed: Jun. 1, 2021

(65) Prior Publication Data
US 2021/0378743 A1    Dec. 9, 2021

Related U.S. Application Data

(60) Provisional application No. 63/033,929, filed on Jun. 3, 2020.

(51) Int. Cl.
*A61B 18/24*    (2006.01)
*A61B 18/14*    (2006.01)
(Continued)

(52) U.S. Cl.
CPC ........ *A61B 18/245* (2013.01); *A61B 18/1492* (2013.01); *A61B 2017/00154* (2013.01);
(Continued)

(58) Field of Classification Search
CPC .............. A61B 18/245; A61B 18/1492; A61B 2017/00154
See application file for complete search history.

(56) References Cited

U.S. PATENT DOCUMENTS 4,649,924 A    3/1987    Taccardi
4,699,147 A    10/1987   Chilson et al.
(Continued)

FOREIGN PATENT DOCUMENTS

AU    2017205323    1/2022
AU    2019452180    1/2022
(Continued)

OTHER PUBLICATIONS

International Search Report and Written Opinion dated Jun. 28, 2022, in PCT Application Serial No. PCT/US2022/015577.
(Continued)

*Primary Examiner* — Mallika D Fairchild
*Assistant Examiner* — Thien Jason Tran
(74) *Attorney, Agent, or Firm* — ROEDER & BRODER LLP; James P. Broder

(57) ABSTRACT

A catheter system (100) for treating a treatment site (106) within or adjacent to the vessel wall of a blood vessel (108), or the heart valve, includes an energy source (124), a balloon (104), an energy guide (122A), and a balloon integrity protection system (142). The energy source (124) generates energy. The balloon (104) is positionable substantially adjacent to the treatment site (106). The balloon (104) has a balloon wall (130) that defines a balloon interior (146). The balloon (104) is configured to retain a balloon fluid (132) within the balloon interior (146). The energy guide (122A) is configured to receive energy from the energy source (124) and guide the energy into the balloon interior (146) so that plasma is formed in the balloon fluid (132) within the
(Continued)

balloon interior (146). The balloon integrity protection system (142) is operatively coupled to the balloon (104). The balloon integrity protection system (142) is configured to inhibit rupture of the balloon (104) due to the plasma formed in the balloon fluid (132) within the balloon interior (146) during use of the catheter system (100).

26 Claims, 11 Drawing Sheets

(51) Int. Cl.
    *A61B 17/00*     (2006.01)
    *A61B 18/00*     (2006.01)

(52) U.S. Cl.
    CPC ............... *A61B 2018/00077* (2013.01); *A61B 2018/00095* (2013.01); *A61B 2018/0022* (2013.01); *A61B 2018/00369* (2013.01)

(56) References Cited

U.S. PATENT DOCUMENTS

| | | |
|---|---|---|
| 4,799,479 A | 1/1989 | Spears |
| 4,850,351 A | 7/1989 | Herman |
| 4,913,142 A | 4/1990 | Kittrell et al. |
| 4,932,954 A | 6/1990 | Wondrazek et al. |
| 4,955,895 A | 9/1990 | Suglyama |
| 4,960,108 A | 10/1990 | Reichel et al. |
| 4,994,059 A | 2/1991 | Kosa et al. |
| 4,998,930 A | 3/1991 | Lundahl |
| 5,034,010 A | 7/1991 | Kittrell et al. |
| 5,041,121 A | 8/1991 | Wondrazek et al. |
| 5,082,343 A | 1/1992 | Coult et al. |
| 5,093,877 A | 3/1992 | Aita et al. |
| 5,104,391 A | 4/1992 | Ingle |
| 5,104,392 A | 4/1992 | Kittrell et al. |
| 5,109,452 A | 4/1992 | Selvin et al. |
| 5,116,227 A | 5/1992 | Levy |
| 5,126,165 A | 6/1992 | Akihama et al. |
| 5,152,768 A | 10/1992 | Bhatta |
| 5,173,049 A | 12/1992 | Levy |
| 5,176,674 A | 1/1993 | Hofmann |
| 5,181,921 A † | 1/1993 | Makita |
| 5,200,838 A | 4/1993 | Nudelman |
| 5,290,277 A | 3/1994 | Vercimak et al. |
| 5,324,282 A | 6/1994 | Dodick |
| 5,328,472 A | 7/1994 | Steinke et al. |
| 5,336,184 A | 8/1994 | Teirstein |
| 5,372,138 A | 12/1994 | Crowley |
| 5,387,225 A | 2/1995 | Euteneur |
| 5,400,428 A | 3/1995 | Grace |
| 5,410,797 A | 5/1995 | Steinke et al. |
| 5,422,926 A | 6/1995 | Smith |
| 5,454,809 A | 10/1995 | Janssen |
| 5,456,680 A | 10/1995 | Taylor |
| 5,474,537 A | 12/1995 | Solar |
| 5,509,917 A | 4/1996 | Cecchetti |
| 5,540,679 A | 7/1996 | Fram |
| 5,562,657 A | 10/1996 | Griffin |
| 5,598,494 A | 1/1997 | Behrmann et al. |
| 5,609,606 A | 3/1997 | O'Boyle |
| 5,611,807 A | 3/1997 | O'Boyle |
| 5,661,829 A | 8/1997 | Zheng |
| 5,697,377 A | 12/1997 | Wittkamph |
| 5,718,241 A | 2/1998 | Ben-Haim et al. |
| 5,729,583 A | 3/1998 | Tang |
| 5,764,843 A | 6/1998 | Macken et al. |
| 5,772,609 A | 6/1998 | Nguyen et al. |
| 5,860,974 A | 1/1999 | Abele |
| 5,891,135 A | 4/1999 | Jackson et al. |
| 5,906,611 A | 5/1999 | Dodick et al. |
| 5,944,697 A | 8/1999 | Benett et al. |
| 6,015,404 A | 1/2000 | Altshuler |
| 6,080,119 A | 6/2000 | Schwarze et al. |
| 6,123,923 A | 9/2000 | Unger |
| 6,139,510 A | 10/2000 | Palermo |
| 6,186,963 B1 | 2/2001 | Schwarze et al. |
| 6,203,537 B1 | 3/2001 | Adrian |
| 6,210,404 B1 | 4/2001 | Shadduck |
| 6,339,470 B1 | 1/2002 | Papademetriou et al. |
| 6,356,575 B1 | 3/2002 | Fukumoto |
| 6,368,318 B1 | 4/2002 | Visuri et al. |
| 6,423,055 B1 | 7/2002 | Farr |
| 6,500,174 B1 | 12/2002 | Maguire et al. |
| 6,514,203 B2 | 2/2003 | Bukshpan |
| 6,514,249 B1 | 2/2003 | Maguire |
| 6,524,251 B2 | 3/2003 | Rabiner et al. |
| 6,538,739 B1 | 3/2003 | Visuri et al. |
| 6,548,010 B1 | 4/2003 | Stivland et al. |
| 6,560,387 B1 | 5/2003 | Hehlen et al. |
| 6,607,502 B1 | 8/2003 | Maguire et al. |
| 6,631,220 B1 | 10/2003 | Liang et al. |
| 6,652,547 B2 | 11/2003 | Rabiner et al. |
| 6,666,834 B2 | 12/2003 | Restle et al. |
| 6,702,781 B1 | 3/2004 | Reifart et al. |
| 6,773,447 B2 † | 8/2004 | Laguna |
| 6,824,554 B1 | 11/2004 | Jang |
| 6,849,994 B1 | 2/2005 | White et al. |
| 6,890,317 B2 | 5/2005 | Gerdts et al. |
| 6,947,785 B1 | 9/2005 | Beatty et al. |
| 6,966,890 B2 | 11/2005 | Coyle et al. |
| 6,978,168 B2 | 12/2005 | Beatty et al. |
| 6,990,370 B1 | 1/2006 | Beatty et al. |
| 7,273,470 B2 | 9/2007 | Wantink |
| 7,309,324 B2 | 12/2007 | Hayes et al. |
| 7,367,967 B2 | 5/2008 | Eidenschink |
| 7,470,240 B2 | 12/2008 | Schultheiss et al. |
| 7,539,231 B1 | 5/2009 | Honea et al. |
| 7,569,032 B2 | 8/2009 | Naimark et al. |
| 7,599,588 B2 | 10/2009 | Eberle et al. |
| 7,641,646 B2 | 1/2010 | Kennedy, II |
| 7,713,260 B2 | 5/2010 | Lessard |
| 7,758,572 B2 † | 7/2010 | Weber |
| 7,762,984 B2 | 7/2010 | Kumoyama et al. |
| 7,810,395 B2 | 10/2010 | Zhou |
| 7,850,685 B2 | 12/2010 | Kunis et al. |
| 7,867,178 B2 | 1/2011 | Simnacher |
| 7,909,797 B2 | 3/2011 | Kennedy, II et al. |
| 7,967,781 B2 | 6/2011 | Simpson et al. |
| 7,972,299 B2 | 7/2011 | Carter |
| 7,985,189 B1 | 7/2011 | Ogden et al. |
| 8,021,328 B2 | 9/2011 | Lee |
| 8,029,473 B2 | 10/2011 | Carter |
| 8,043,256 B2 | 10/2011 | Hansen |
| 8,088,121 B2 | 1/2012 | Nishide |
| 8,162,859 B2 | 4/2012 | Schultheiss et al. |
| 8,166,825 B2 | 5/2012 | Zhou |
| 8,192,368 B2 | 6/2012 | Woodruff |
| 8,267,886 B2 | 9/2012 | Ewing |
| 8,292,913 B2 | 10/2012 | Warnack |
| 8,328,820 B2 | 12/2012 | Diamant |
| 8,364,235 B2 | 1/2013 | Kordis et al. |
| 8,382,738 B2 | 2/2013 | Simpson et al. |
| 8,414,527 B2 | 4/2013 | Mallaby |
| 8,419,613 B2 | 4/2013 | Saadat |
| 8,439,890 B2 | 5/2013 | Beyar |
| 8,556,813 B2 | 10/2013 | Cashman et al. |
| 8,574,247 B2 | 11/2013 | Adams et al. |
| 8,657,814 B2 | 2/2014 | Werneth |
| 8,709,075 B2 | 4/2014 | Adams et al. |
| 8,728,091 B2 | 5/2014 | Hakala et al. |
| 8,734,424 B2 | 5/2014 | Watanabe |
| 8,747,416 B2 † | 6/2014 | Hakala |
| 8,784,362 B2 | 7/2014 | Boutilette |
| 8,834,510 B2 | 9/2014 | Wilson et al. |
| 8,888,788 B2 | 11/2014 | Hakala et al. |
| 8,956,371 B2 † | 2/2015 | Hawkins |
| 8,956,374 B2 | 2/2015 | Hawkins et al. |
| 8,986,339 B2 | 3/2015 | Warnack |
| 8,992,817 B2 † | 3/2015 | Stamberg |
| 9,005,216 B2 | 4/2015 | Hakala et al. |
| 9,011,462 B2 | 4/2015 | Adams et al. |
| 9,011,463 B2 | 4/2015 | Adams et al. |

(56) References Cited

U.S. PATENT DOCUMENTS

| | | |
|---|---|---|
| 9,011,511 B2 | 4/2015 | Gregorich |
| 9,044,618 B2 | 6/2015 | Hawkins et al. |
| 9,044,619 B2 | 6/2015 | Hawkins et al. |
| 9,072,534 B2 | 7/2015 | Adams et al. |
| 9,089,669 B2 | 7/2015 | Haslinger et al. |
| 9,131,949 B2 | 9/2015 | Coleman et al. |
| 9,138,249 B2 | 9/2015 | Adams et al. |
| 9,138,260 B2 | 9/2015 | Miller et al. |
| 9,180,280 B2 † | 11/2015 | Hawkins |
| 9,220,521 B2 | 12/2015 | Hawkins et al. |
| 9,237,984 B2 | 1/2016 | Hawkins et al. |
| 9,289,132 B2 | 3/2016 | Ghaffari et al. |
| 9,289,224 B2 | 3/2016 | Adams et al. |
| 9,320,530 B2 | 4/2016 | Grace |
| 9,333,000 B2 | 5/2016 | Hakala et al. |
| 9,339,632 B2 | 5/2016 | Eidenschink et al. |
| 9,364,645 B2 | 6/2016 | Erikawa |
| 9,375,223 B2 | 6/2016 | Wallace |
| 9,421,025 B2 | 8/2016 | Hawkins et al. |
| 9,433,428 B2 | 9/2016 | Hakala et al. |
| 9,433,745 B2 | 9/2016 | Cully |
| 9,504,809 B2 | 11/2016 | Bo |
| 9,510,887 B2 | 12/2016 | Burnett |
| 9,522,012 B2 | 12/2016 | Adams |
| 9,554,815 B2 | 1/2017 | Adams et al. |
| 9,555,267 B2 | 1/2017 | Ein-gal |
| 9,566,209 B2 | 2/2017 | Katragadda et al. |
| 9,579,114 B2 | 2/2017 | Mantell et al. |
| 9,585,684 B2 | 3/2017 | Nita et al. |
| 9,592,328 B2 | 3/2017 | Jeevanandam |
| 9,629,567 B2 | 4/2017 | Porath et al. |
| 9,642,673 B2 | 5/2017 | Adams |
| 9,662,069 B2 | 5/2017 | De Graff et al. |
| 9,687,166 B2 | 6/2017 | Subramaniam |
| 9,730,715 B2 | 8/2017 | Adams |
| 9,737,361 B2 | 8/2017 | Magana |
| 9,764,142 B2 | 9/2017 | Imran |
| 9,782,570 B2 | 10/2017 | Hirszowicz |
| 9,814,476 B2 | 11/2017 | Adams et al. |
| 9,833,348 B2 | 12/2017 | Jordan et al. |
| 9,839,764 B2 | 12/2017 | Chouinard |
| 9,861,377 B2 | 1/2018 | Mantell et al. |
| 9,867,629 B2 | 1/2018 | Hawkins et al. |
| 9,878,135 B2 | 1/2018 | Holzapfel et al. |
| 9,894,756 B2 | 2/2018 | Weinkam et al. |
| 9,901,704 B2 | 2/2018 | Appling |
| 9,955,946 B2 | 5/2018 | Miller et al. |
| 9,974,963 B2 | 5/2018 | Imran |
| 9,974,970 B2 | 5/2018 | Nuta et al. |
| 9,993,292 B2 | 6/2018 | Adams et al. |
| 10,039,561 B2 | 8/2018 | Adams et al. |
| 10,086,175 B2 | 10/2018 | Torres et al. |
| 10,124,153 B2 | 11/2018 | Feig |
| 10,136,829 B2 | 11/2018 | Deno et al. |
| 10,149,690 B2 | 12/2018 | Hawkins et al. |
| 10,159,505 B2 | 12/2018 | Hakala et al. |
| 10,194,994 B2 | 2/2019 | Deno et al. |
| 10,201,387 B2 | 2/2019 | Grace et al. |
| 10,206,698 B2 | 2/2019 | Hakala et al. |
| 10,226,265 B2 | 3/2019 | Ku et al. |
| 10,245,410 B2 | 4/2019 | Aggerholm |
| 10,357,264 B2 | 7/2019 | Kat-Kuoy |
| 10,405,923 B2 | 9/2019 | Yu et al. |
| 10,406,031 B2 | 9/2019 | Thyzel |
| 10,406,318 B2 | 9/2019 | Williams |
| 10,420,569 B2 | 9/2019 | Adams |
| 10,439,791 B2 | 10/2019 | Kalhan |
| 10,441,300 B2 | 10/2019 | Hawkins |
| 10,449,339 B2 | 10/2019 | Wilson et al. |
| 10,463,430 B2 | 11/2019 | Dick |
| 10,478,202 B2 | 11/2019 | Adams et al. |
| 10,517,620 B2 | 12/2019 | Adams |
| 10,517,621 B1 | 12/2019 | Hakala et al. |
| 10,537,287 B2 | 1/2020 | Braido et al. |
| 10,555,744 B2 | 2/2020 | Nguyen et al. |
| 10,561,428 B2 | 2/2020 | Eggert et al. |
| 10,583,277 B2 | 3/2020 | Rundquist |
| 10,589,073 B2 | 3/2020 | Mallaby |
| 10,617,850 B2 | 4/2020 | Tal |
| 10,646,240 B2 | 5/2020 | Betelia et al. |
| 10,668,245 B2 | 6/2020 | Kanae |
| 10,682,178 B2 | 6/2020 | Adams et al. |
| 10,695,531 B2 | 6/2020 | Suzuki |
| 10,702,293 B2 | 7/2020 | Adams et al. |
| 10,709,462 B2 | 7/2020 | Nguyen et al. |
| 10,709,872 B2 | 7/2020 | Alvarez et al. |
| 10,758,255 B2 | 9/2020 | Adams |
| 10,797,684 B1 | 10/2020 | Benz et al. |
| 10,799,688 B2 | 10/2020 | Calhoun |
| 10,842,567 B2 | 11/2020 | Grace et al. |
| 10,850,075 B2 | 12/2020 | Tarunaga |
| 10,857,329 B2 | 12/2020 | Davies |
| 10,933,225 B2 | 3/2021 | Campbell |
| 10,959,743 B2 | 3/2021 | Adams et al. |
| 10,966,737 B2 | 4/2021 | Nguyen |
| 10,967,156 B2 | 4/2021 | Gulachenski |
| 10,973,538 B2 | 4/2021 | Hakala et al. |
| 10,980,987 B2 | 4/2021 | Tarunaga |
| 11,000,299 B2 | 5/2021 | Hawkins et al. |
| 11,020,135 B1 | 6/2021 | Hawkins |
| 11,026,707 B2 | 6/2021 | Ku et al. |
| 11,058,492 B2 | 7/2021 | Grace et al. |
| 11,076,874 B2 | 8/2021 | Hakala et al. |
| 11,116,939 B2 | 9/2021 | Jamous et al. |
| 11,141,131 B2 | 10/2021 | Stigall |
| 11,207,493 B2 | 12/2021 | Suzuki et al. |
| 11,213,661 B2 | 1/2022 | Spindler |
| 11,229,772 B2 | 1/2022 | Nita |
| 11,229,776 B2 | 1/2022 | Kugler et al. |
| 11,246,659 B2 | 2/2022 | Grace et al. |
| 11,253,681 B2 | 2/2022 | Williams |
| 11,484,327 B2 | 11/2022 | Anderson et al. |
| 11,633,200 B2 | 4/2023 | Anderson et al. |
| 11,779,363 B2 | 10/2023 | Vo |
| 11,826,530 B2 | 11/2023 | Suzuki |
| 11,911,054 B2 | 2/2024 | Singla |
| 11,911,056 B2 | 2/2024 | Anderson et al. |
| 11,918,285 B2 | 3/2024 | Sun et al. |
| 11,944,331 B2 | 4/2024 | Anderson et al. |
| 2001/0016761 A1 | 8/2001 | Rudie |
| 2001/0049464 A1 | 12/2001 | Ganz |
| 2001/0051784 A1 | 12/2001 | Brisken |
| 2002/0045811 A1 | 4/2002 | Kittrell et al. |
| 2002/0052621 A1 | 5/2002 | Fried et al. |
| 2002/0065512 A1 | 5/2002 | Fjield et al. |
| 2002/0082553 A1 | 6/2002 | Duchamp |
| 2002/0183620 A1 | 12/2002 | Tearney |
| 2002/0183729 A1 | 12/2002 | Farr et al. |
| 2002/0188204 A1 | 12/2002 | McNamara et al. |
| 2003/0009157 A1 | 1/2003 | Levine et al. |
| 2003/0050632 A1 | 3/2003 | Fjield et al. |
| 2003/0065316 A1 | 4/2003 | Levine et al. |
| 2003/0114901 A1 | 6/2003 | Loeb et al. |
| 2003/0125719 A1 | 7/2003 | Furnish |
| 2003/0144654 A1 | 7/2003 | Hilal |
| 2003/0176873 A1 | 9/2003 | Chernenko et al. |
| 2004/0002677 A1 | 1/2004 | Gentsler |
| 2004/0024349 A1 | 2/2004 | Flock et al. |
| 2004/0073251 A1 | 4/2004 | Weber |
| 2004/0097996 A1 | 5/2004 | Rabiner |
| 2004/0133254 A1 | 7/2004 | Sterzer et al. |
| 2004/0162508 A1 | 8/2004 | Uebelacker |
| 2004/0210278 A1 | 10/2004 | Boll |
| 2004/0243119 A1 | 12/2004 | Lane et al. |
| 2004/0249401 A1 | 12/2004 | Rabiner |
| 2004/0254570 A1 | 12/2004 | Hadsjicostis |
| 2005/0010095 A1 | 1/2005 | Stewart et al. |
| 2005/0021013 A1 | 1/2005 | Visuri |
| 2005/0080396 A1 | 4/2005 | Rontal |
| 2005/0113722 A1 | 5/2005 | Schultheiss |
| 2005/0171437 A1 | 8/2005 | Carberry |
| 2005/0171527 A1 | 8/2005 | Bhola |
| 2005/0251131 A1 | 11/2005 | Lesh |
| 2005/0259319 A1 | 11/2005 | Brooker |

(56) References Cited

U.S. PATENT DOCUMENTS

| | | |
|---|---|---|
| 2005/0273014 A1 | 12/2005 | Gianchandani et al. |
| 2005/0277839 A1 | 12/2005 | Alderman et al. |
| 2006/0033241 A1 | 2/2006 | Schewe et al. |
| 2006/0084966 A1 | 4/2006 | Maguire et al. |
| 2006/0098921 A1 | 5/2006 | Benaron et al. |
| 2006/0190022 A1 | 8/2006 | Beyar et al. |
| 2006/0200039 A1 | 9/2006 | Brockway et al. |
| 2006/0221528 A1 | 10/2006 | Li et al. |
| 2006/0241524 A1 | 10/2006 | Lee et al. |
| 2006/0241572 A1 | 10/2006 | Zhou |
| 2006/0241733 A1 | 10/2006 | Zhang et al. |
| 2006/0270976 A1 | 11/2006 | Savage et al. |
| 2007/0027524 A1 | 2/2007 | Johnson |
| 2007/0043340 A1 | 2/2007 | Thyzel |
| 2007/0060990 A1 | 3/2007 | Satake |
| 2007/0088380 A1 | 4/2007 | Hirszowicz et al. |
| 2007/0118057 A1 | 5/2007 | Ein-gal |
| 2007/0142819 A1 | 6/2007 | El-Nounou et al. |
| 2007/0142821 A1 | 6/2007 | Hennessy et al. |
| 2007/0179496 A1 | 8/2007 | Swoyer |
| 2007/0239082 A1 | 10/2007 | Schultheiss et al. |
| 2007/0255270 A1 | 11/2007 | Carney |
| 2007/0264353 A1 | 11/2007 | Myntti et al. |
| 2007/0270897 A1 | 11/2007 | Skerven |
| 2007/0280311 A1 | 12/2007 | Hofmann |
| 2007/0299392 A1 | 12/2007 | Beyar et al. |
| 2008/0033519 A1 | 2/2008 | Burwell |
| 2008/0081950 A1 | 4/2008 | Koenig et al. |
| 2008/0086118 A1 | 4/2008 | Lai |
| 2008/0095714 A1 | 4/2008 | Castella et al. |
| 2008/0097251 A1 | 4/2008 | Babaev |
| 2008/0108867 A1 | 5/2008 | Zhou |
| 2008/0114341 A1 | 5/2008 | Thyzel |
| 2008/0132810 A1 | 6/2008 | Scoseria et al. |
| 2008/0175539 A1 | 7/2008 | Brown |
| 2008/0195088 A1 | 8/2008 | Farr et al. |
| 2008/0214891 A1 | 9/2008 | Slenker et al. |
| 2008/0221550 A1 | 9/2008 | Lee |
| 2008/0281157 A1 | 11/2008 | Miyagi et al. |
| 2008/0296152 A1 | 12/2008 | Voss |
| 2008/0319356 A1 | 12/2008 | Cain et al. |
| 2009/0036803 A1 | 2/2009 | Warlick et al. |
| 2009/0043300 A1 | 2/2009 | Reitmajer et al. |
| 2009/0054881 A1 | 2/2009 | Krespi |
| 2009/0097806 A1 | 4/2009 | Viellerobe et al. |
| 2009/0125007 A1 | 5/2009 | Splinter |
| 2009/0131921 A1 | 5/2009 | Kurtz et al. |
| 2009/0192495 A1 | 7/2009 | Ostrovsky et al. |
| 2009/0240242 A1 | 9/2009 | Neuberger |
| 2009/0247945 A1 | 10/2009 | Levit |
| 2009/0281531 A1 | 11/2009 | Rizoiu |
| 2009/0292296 A1 | 11/2009 | Pansky |
| 2009/0296751 A1 | 12/2009 | Kewitsch et al. |
| 2009/0299327 A1 | 12/2009 | Tilson et al. |
| 2009/0306533 A1 | 12/2009 | Rousche |
| 2009/0312768 A1 | 12/2009 | Hawkins et al. |
| 2010/0016862 A1 | 1/2010 | Hawkins et al. |
| 2010/0036294 A1† | 2/2010 | Mantell |
| 2010/0063491 A1 | 3/2010 | Verhagen |
| 2010/0094209 A1 | 4/2010 | Drasler et al. |
| 2010/0114020 A1 | 5/2010 | Hawkins et al. |
| 2010/0114065 A1 | 5/2010 | Hawkins et al. |
| 2010/0125268 A1 | 5/2010 | Gustus et al. |
| 2010/0160838 A1 | 6/2010 | Krespi |
| 2010/0160903 A1 | 6/2010 | Krespi |
| 2010/0168572 A1 | 7/2010 | Sliwa |
| 2010/0168836 A1 | 7/2010 | Kassab |
| 2010/0168862 A1 | 7/2010 | Edie et al. |
| 2010/0179632 A1 | 7/2010 | Bruszewski et al. |
| 2010/0191089 A1 | 7/2010 | Stebler et al. |
| 2010/0198114 A1 | 8/2010 | Novak et al. |
| 2010/0199773 A1 | 8/2010 | Zhou |
| 2010/0222786 A1 | 9/2010 | Kassab |
| 2010/0234875 A1 | 9/2010 | Allex et al. |
| 2010/0256535 A1 | 10/2010 | Novak et al. |
| 2010/0265733 A1 | 10/2010 | O'Leary |
| 2010/0316333 A1 | 12/2010 | Luther |
| 2011/0034832 A1 | 2/2011 | Cioanta et al. |
| 2011/0059415 A1 | 3/2011 | Kasenbacher |
| 2011/0082452 A1 | 4/2011 | Melsky |
| 2011/0082534 A1 | 4/2011 | Wallace |
| 2011/0118634 A1 | 5/2011 | Golan |
| 2011/0144502 A1 | 6/2011 | Zhou et al. |
| 2011/0184244 A1 | 7/2011 | Kagaya et al. |
| 2011/0208185 A1 | 8/2011 | Diamant et al. |
| 2011/0213349 A1 | 9/2011 | Brown |
| 2011/0245740 A1 | 10/2011 | Novak et al. |
| 2011/0257641 A1 | 10/2011 | Hastings et al. |
| 2011/0263921 A1 | 10/2011 | Vrba et al. |
| 2011/0275990 A1 | 11/2011 | Besser et al. |
| 2011/0306956 A1 | 12/2011 | Islam |
| 2012/0064141 A1 | 3/2012 | Andreacchi et al. |
| 2012/0071715 A1 | 3/2012 | Beyar et al. |
| 2012/0071867 A1 | 3/2012 | Ryan |
| 2012/0071889 A1 | 3/2012 | Mantell et al. |
| 2012/0089132 A1 | 4/2012 | Dick et al. |
| 2012/0095335 A1 | 4/2012 | Sverdlik et al. |
| 2012/0095461 A1 | 4/2012 | Herscher et al. |
| 2012/0116289 A1 | 5/2012 | Hawkins et al. |
| 2012/0116486 A1 | 5/2012 | Naga et al. |
| 2012/0123331 A1 | 5/2012 | Satake |
| 2012/0123399 A1 | 5/2012 | Belikov |
| 2012/0143131 A1 | 6/2012 | Tun |
| 2012/0157892 A1 | 6/2012 | Reitmajer et al. |
| 2012/0197245 A1* | 8/2012 | Burnett ............ A61B 18/04 |
| | | 606/21 |
| 2012/0203255 A1 | 8/2012 | Hawkins et al. |
| 2012/0221013 A1 | 8/2012 | Hawkins et al. |
| 2012/0232409 A1 | 9/2012 | Stahmann |
| 2012/0296367 A1 | 11/2012 | Grovender et al. |
| 2012/0323211 A1* | 12/2012 | Ogle ................ A61L 29/145 |
| | | 604/500 |
| 2012/0330293 A1 | 12/2012 | Arai |
| 2013/0030431 A1 | 1/2013 | Adams |
| 2013/0030447 A1 | 1/2013 | Adams |
| 2013/0041355 A1 | 2/2013 | Heeren et al. |
| 2013/0046207 A1 | 2/2013 | Capelli |
| 2013/0046293 A1 | 2/2013 | Arai et al. |
| 2013/0053762 A1 | 2/2013 | Rontal et al. |
| 2013/0110003 A1 | 5/2013 | Surti |
| 2013/0116714 A1 | 5/2013 | Adams et al. |
| 2013/0165764 A1 | 6/2013 | Scheuermann |
| 2013/0190803 A1 | 7/2013 | Angel et al. |
| 2013/0197614 A1 | 8/2013 | Gustus |
| 2013/0218054 A1 | 8/2013 | Sverdlik et al. |
| 2013/0226131 A1 | 8/2013 | Bacino et al. |
| 2013/0253466 A1 | 9/2013 | Campbell |
| 2013/0274726 A1 | 10/2013 | Takayama |
| 2013/0345617 A1 | 12/2013 | Wallace |
| 2014/0005576 A1 | 1/2014 | Adams |
| 2014/0005706 A1 | 1/2014 | Gelfand et al. |
| 2014/0012186 A1 | 1/2014 | Thyzel |
| 2014/0039002 A1 | 1/2014 | Adams et al. |
| 2014/0039358 A1 | 2/2014 | Zhou et al. |
| 2014/0039513 A1 | 2/2014 | Hakala |
| 2014/0046229 A1 | 2/2014 | Hawkins et al. |
| 2014/0046353 A1 | 2/2014 | Adams |
| 2014/0052146 A1 | 2/2014 | Curtis et al. |
| 2014/0052147 A1 | 2/2014 | Hakala et al. |
| 2014/0058294 A1 | 2/2014 | Gross et al. |
| 2014/0074111 A1 | 3/2014 | Hakala |
| 2014/0114198 A1 | 4/2014 | Samada et al. |
| 2014/0153087 A1 | 6/2014 | Hutchings et al. |
| 2014/0155990 A1 | 6/2014 | Nyuli |
| 2014/0180069 A1 | 6/2014 | Millett |
| 2014/0180126 A1 | 6/2014 | Millett |
| 2014/0180134 A1 | 6/2014 | Hoseit |
| 2014/0188094 A1 | 7/2014 | Islam |
| 2014/0228829 A1 | 8/2014 | Schmitt |
| 2014/0257144 A1 | 9/2014 | Capelli et al. |
| 2014/0257148 A1 | 9/2014 | Jie |
| 2014/0276573 A1 | 9/2014 | Miesel |
| 2014/0288570 A1 | 9/2014 | Adams |
| 2014/0309536 A1 | 10/2014 | Douk et al. |

(56) References Cited

U.S. PATENT DOCUMENTS

| | | | |
|---|---|---|---|
| 2014/0336632 A1* | 11/2014 | Toth | A61B 18/1492 606/34 |
| 2014/0336637 A1 | 11/2014 | Agrawal | |
| 2014/0357997 A1 | 12/2014 | Hartmann | |
| 2015/0003900 A1 | 1/2015 | Ullrich et al. | |
| 2015/0005576 A1 | 1/2015 | Diodone et al. | |
| 2015/0039002 A1 | 2/2015 | Hawkins | |
| 2015/0057648 A1 | 2/2015 | Swift et al. | |
| 2015/0073430 A1 | 3/2015 | Hakala et al. | |
| 2015/0080875 A1 | 3/2015 | Kasprzyk et al. | |
| 2015/0100048 A1 | 4/2015 | Hiereth et al. | |
| 2015/0105715 A1 | 4/2015 | Pikus et al. | |
| 2015/0119870 A1 | 4/2015 | Rudie | |
| 2015/0126990 A1 | 5/2015 | Sharma | |
| 2015/0141764 A1 | 5/2015 | Harks et al. | |
| 2015/0250542 A1 | 9/2015 | Islam | |
| 2015/0276689 A1 | 10/2015 | Watanabe | |
| 2015/0313732 A1 | 11/2015 | Fulton, III | |
| 2015/0320432 A1 | 11/2015 | Adams | |
| 2015/0342678 A1 | 12/2015 | Deladurantaye et al. | |
| 2015/0359432 A1 | 12/2015 | Ehrenreich | |
| 2015/0359557 A1 | 12/2015 | Shimokawa | |
| 2016/0008016 A1 | 1/2016 | Cioanta et al. | |
| 2016/0016016 A1 | 1/2016 | Taylor et al. | |
| 2016/0018602 A1 | 1/2016 | Govari et al. | |
| 2016/0022294 A1 | 1/2016 | Cioanta et al. | |
| 2016/0038087 A1 | 2/2016 | Hunter | |
| 2016/0095610 A1 | 4/2016 | Lipowski et al. | |
| 2016/0135828 A1 | 5/2016 | Hawkins et al. | |
| 2016/0135891 A1 | 5/2016 | Feldman | |
| 2016/0143522 A1 | 5/2016 | Ransbury | |
| 2016/0151639 A1 | 6/2016 | Scharf et al. | |
| 2016/0183819 A1 | 6/2016 | Burnett | |
| 2016/0183957 A1 | 6/2016 | Hakala et al. | |
| 2016/0184020 A1 | 6/2016 | Kowalewski et al. | |
| 2016/0184022 A1 | 6/2016 | Grace et al. | |
| 2016/0184023 A1 | 6/2016 | Grace et al. | |
| 2016/0184526 A1 | 6/2016 | Beyar | |
| 2016/0184570 A1 | 6/2016 | Grace et al. | |
| 2016/0228187 A1 | 8/2016 | Gross | |
| 2016/0262784 A1 | 9/2016 | Grace et al. | |
| 2016/0270806 A1 | 9/2016 | Wallace | |
| 2016/0302762 A1 | 10/2016 | Stigall et al. | |
| 2016/0234534 A1 | 11/2016 | Hawkins et al. | |
| 2016/0324564 A1 | 11/2016 | Gerlach et al. | |
| 2016/0331389 A1 | 11/2016 | Hakala et al. | |
| 2016/0367274 A1 | 12/2016 | Wallace | |
| 2016/0367275 A1 | 12/2016 | Wallace | |
| 2017/0049463 A1 | 2/2017 | Popovic et al. | |
| 2017/0056035 A1 | 3/2017 | Adams | |
| 2017/0056087 A1* | 3/2017 | Buckley | A61B 18/02 |
| 2017/0086867 A1 | 3/2017 | Adams | |
| 2017/0119469 A1 | 5/2017 | Shimizu et al. | |
| 2017/0119470 A1 | 5/2017 | Diamant et al. | |
| 2017/0135709 A1 | 5/2017 | Nguyen et al. | |
| 2017/0151421 A1 | 6/2017 | Asher | |
| 2017/0192242 A1 | 7/2017 | Laycock | |
| 2017/0209050 A1 | 7/2017 | Fengler et al. | |
| 2017/0265942 A1 | 9/2017 | Grace et al. | |
| 2017/0303946 A1 | 10/2017 | Ku et al. | |
| 2017/0311965 A1 | 11/2017 | Adams | |
| 2018/0008348 A1 | 1/2018 | Grace et al. | |
| 2018/0042661 A1 | 2/2018 | Long | |
| 2018/0042677 A1 | 2/2018 | Yu et al. | |
| 2018/0045897 A1 | 2/2018 | Chia | |
| 2018/0049877 A1 | 2/2018 | Venkatasubramanian | |
| 2018/0085174 A1 | 3/2018 | Radtke et al. | |
| 2018/0092763 A1 | 4/2018 | Dagan et al. | |
| 2018/0095287 A1 | 4/2018 | Jeng et al. | |
| 2018/0098779 A1 | 4/2018 | Betelia et al. | |
| 2018/0152568 A1 | 6/2018 | Kat-kuoy | |
| 2018/0214677 A1 | 8/2018 | Tarunaga | |
| 2018/0238675 A1 | 8/2018 | Wan | |
| 2018/0256250 A1 | 9/2018 | Adams et al. | |
| 2018/0280005 A1 | 10/2018 | Parmentier | |
| 2018/0303501 A1 | 10/2018 | Hawkins | |
| 2018/0303503 A1 | 10/2018 | Eggert et al. | |
| 2018/0303504 A1 | 10/2018 | Eggert et al. | |
| 2018/0304053 A1 | 10/2018 | Eggert et al. | |
| 2018/0323571 A1 | 11/2018 | Brown et al. | |
| 2018/0333043 A1 | 11/2018 | Teriluc | |
| 2018/0360482 A1 | 12/2018 | Nguyen | |
| 2019/0029702 A1 | 1/2019 | De Cicco | |
| 2019/0029703 A1 | 1/2019 | Wasdyke et al. | |
| 2019/0069916 A1 | 3/2019 | Hawkins et al. | |
| 2019/0072378 A1 | 3/2019 | Hane et al. | |
| 2019/0097380 A1 | 3/2019 | Luft et al. | |
| 2019/0099588 A1 | 4/2019 | Ramanath et al. | |
| 2019/0104933 A1 | 4/2019 | Stern | |
| 2019/0117242 A1* | 4/2019 | Lawinger | A61B 18/26 |
| 2019/0150960 A1 | 5/2019 | Nguyen et al. | |
| 2019/0150961 A1 | 5/2019 | Tozzi | |
| 2019/0167349 A1 | 6/2019 | Shamay | |
| 2019/0175111 A1 | 6/2019 | Genereux et al. | |
| 2019/0175300 A1 | 6/2019 | Horn et al. | |
| 2019/0175372 A1 | 6/2019 | Boyden et al. | |
| 2019/0175407 A1 | 6/2019 | Bacher | |
| 2019/0209368 A1 | 7/2019 | Park et al. | |
| 2019/0232066 A1 | 8/2019 | Lim et al. | |
| 2019/0247680 A1 | 8/2019 | Mayer | |
| 2019/0262594 A1 | 8/2019 | Ogata et al. | |
| 2019/0265419 A1 | 8/2019 | Tayebati | |
| 2019/0282249 A1 | 9/2019 | Tran et al. | |
| 2019/0282250 A1 | 9/2019 | Tran et al. | |
| 2019/0321100 A1 | 10/2019 | Masotti et al. | |
| 2019/0321101 A1 | 10/2019 | Massoti et al. | |
| 2019/0328259 A1 | 10/2019 | Deno et al. | |
| 2019/0365400 A1* | 12/2019 | Adams | A61B 17/22029 |
| 2019/0380589 A1 | 12/2019 | Lloret | |
| 2019/0388002 A1 | 12/2019 | Bozsak et al. | |
| 2019/0388110 A1 | 12/2019 | Nguyen et al. | |
| 2019/0388133 A1 | 12/2019 | Sharma | |
| 2019/0388151 A1 | 12/2019 | Bhawalkar | |
| 2020/0000484 A1 | 1/2020 | Hawkins | |
| 2020/0008856 A1 | 1/2020 | Harmouche | |
| 2020/0022754 A1 | 1/2020 | Cottone | |
| 2020/0038087 A1* | 2/2020 | Harmouche | A61B 18/02 |
| 2020/0046429 A1 | 2/2020 | Tschida et al. | |
| 2020/0046949 A1 | 2/2020 | Chisena et al. | |
| 2020/0054352 A1 | 2/2020 | Brouillette et al. | |
| 2020/0060814 A1 | 2/2020 | Murphy | |
| 2020/0061931 A1 | 2/2020 | Brown et al. | |
| 2020/0069371 A1 | 3/2020 | Brown et al. | |
| 2020/0085458 A1 | 3/2020 | Nguyen et al. | |
| 2020/0085459 A1 | 3/2020 | Adams | |
| 2020/0101269 A1 | 4/2020 | Hayes | |
| 2020/0107960 A1 | 4/2020 | Bacher | |
| 2020/0108236 A1 | 4/2020 | Salazar et al. | |
| 2020/0129195 A1 | 4/2020 | McGowan et al. | |
| 2020/0129741 A1 | 4/2020 | Kawwas | |
| 2020/0155812 A1 | 5/2020 | Zhang et al. | |
| 2020/0197019 A1 | 6/2020 | Harper | |
| 2020/0205890 A1* | 7/2020 | Harlev | A61B 18/1492 |
| 2020/0246032 A1 | 8/2020 | Betelia et al. | |
| 2020/0289202 A1 | 9/2020 | Miyagawa et al. | |
| 2020/0297366 A1 | 9/2020 | Nguyen et al. | |
| 2020/0337717 A1 | 10/2020 | Walzman | |
| 2020/0383724 A1 | 12/2020 | Adams et al. | |
| 2020/0397230 A1 | 12/2020 | Massimini et al. | |
| 2020/0397453 A1 | 12/2020 | McGowan | |
| 2020/0398033 A1 | 12/2020 | McGowan et al. | |
| 2020/0405333 A1 | 12/2020 | Massimini et al. | |
| 2020/0405391 A1 | 12/2020 | Massimini | |
| 2020/0406009 A1 | 12/2020 | Massimini et al. | |
| 2020/0406010 A1 | 12/2020 | Massimini et al. | |
| 2021/0038237 A1 | 2/2021 | Adams | |
| 2021/0085347 A1 | 3/2021 | Phan et al. | |
| 2021/0085348 A1 | 3/2021 | Nguyen | |
| 2021/0085383 A1 | 3/2021 | Vo et al. | |
| 2021/0116302 A1 | 4/2021 | Jean-Ruel | |
| 2021/0128241 A1 | 5/2021 | Schultheis | |
| 2021/0137598 A1 | 5/2021 | Cook | |
| 2021/0153939 A1 | 5/2021 | Cook | |
| 2021/0177442 A1 | 6/2021 | Girdhar et al. | |

(56) References Cited

U.S. PATENT DOCUMENTS

| | | | |
|---|---|---|---|
| 2021/0177445 A1 | 6/2021 | Nguyen | |
| 2021/0186613 A1 | 6/2021 | Cook | |
| 2021/0212765 A1 | 7/2021 | Verhagen | |
| 2021/0220052 A1 | 7/2021 | Cook | |
| 2021/0220053 A1 | 7/2021 | Cook | |
| 2021/0244473 A1 | 8/2021 | Cook et al. | |
| 2021/0267685 A1 | 9/2021 | Schultheis | |
| 2021/0275247 A1 † | 9/2021 | Schultheis | |
| 2021/0275249 A1 † | 9/2021 | Massimini | |
| 2021/0282792 A1 | 9/2021 | Adams et al. | |
| 2021/0290259 A1 | 9/2021 | Hakala et al. | |
| 2021/0290286 A1 | 9/2021 | Cook | |
| 2021/0290305 A1 | 9/2021 | Cook | |
| 2021/0298603 A1 | 9/2021 | Feldman | |
| 2021/0307828 A1 † | 10/2021 | Schultheis | |
| 2021/0330384 A1 | 10/2021 | Cook | |
| 2021/0338258 A1 | 11/2021 | Hawkins et al. | |
| 2021/0353359 A1 | 11/2021 | Cook | |
| 2021/0369348 A1 | 12/2021 | Cook | |
| 2021/0378743 A1 | 12/2021 | Massimini et al. | |
| 2021/0378744 A1 | 12/2021 | Fanier et al. | |
| 2021/0386479 A1 | 12/2021 | Massimini et al. | |
| 2022/0000505 A1 | 1/2022 | Hauser | |
| 2022/0000506 A1 | 1/2022 | Hauser | |
| 2022/0000507 A1 | 1/2022 | Hauser | |
| 2022/0000508 A1 | 1/2022 | Schmitt et al. | |
| 2022/0000509 A1 | 1/2022 | Laser et al. | |
| 2022/0000551 A1 | 1/2022 | Govari et al. | |
| 2022/0008130 A1 | 1/2022 | Massimini et al. | |
| 2022/0008693 A1 | 1/2022 | Humbert et al. | |
| 2022/0015785 A1 | 1/2022 | Hakala et al. | |
| 2022/0021190 A1 | 1/2022 | Pecquois | |
| 2022/0022902 A1 | 1/2022 | Spano | |
| 2022/0022912 A1 | 1/2022 | Efremkin | |
| 2022/0023528 A1 | 1/2022 | Long et al. | |
| 2022/0071704 A1 | 3/2022 | Le | |
| 2022/0168594 A1 | 6/2022 | Mayer | |
| 2022/0183738 A1 | 6/2022 | Flores et al. | |
| 2022/0218402 A1 | 7/2022 | Schultheis | |
| 2022/0249165 A1 | 8/2022 | Cook | |
| 2022/0273324 A1 | 9/2022 | Schultheis | |
| 2022/0287732 A1 | 9/2022 | Anderson et al. | |
| 2022/0313293 A1 | 10/2022 | Singh | |
| 2022/0338890 A1 | 10/2022 | Anderson et al. | |
| 2022/0354578 A1 | 11/2022 | Cook | |
| 2022/0387106 A1 | 12/2022 | Cook | |
| 2023/0013920 A1 | 1/2023 | Massimini | |
| 2023/0248376 A1 | 8/2023 | Anderson et al. | |
| 2023/0310073 A1 | 10/2023 | Adams et al. | |
| 2023/0414234 A1 | 12/2023 | Anderson et al. | |
| 2024/0058060 A1 | 2/2024 | Cook | |
| 2024/0065712 A1 | 2/2024 | Schultheis | |
| 2024/0122648 A1 | 4/2024 | Cook | |
| 2024/0189543 A1 | 6/2024 | Salinas | |
| 2024/0216062 A1 | 7/2024 | Cook | |
| 2024/0277410 A1 | 8/2024 | Cook | |
| 2024/0285296 A1 | 8/2024 | Vo | |
| 2024/0382258 A1 | 11/2024 | Schultheis | |

FOREIGN PATENT DOCUMENTS

| | | | |
|---|---|---|---|
| AU | 2022227829 | | 9/2022 |
| CA | 2229806 | | 3/1997 |
| CA | 2281519 | | 8/1998 |
| CA | 2983655 | | 10/2016 |
| CA | 3209797 | | 9/2022 |
| CN | 102057422 | | 5/2011 |
| CN | 109223100 | | 1/2019 |
| CN | 110638501 | | 1/2020 |
| CN | 110638501 | A | 1/2020 |
| CN | 106794043 | | 3/2020 |
| CN | 11399346 | | 1/2022 |
| CN | 107411805 | | 1/2022 |
| CN | 107899126 | | 1/2022 |
| CN | 109475378 | | 1/2022 |
| CN | 113876388 | | 1/2022 |
| CN | 113877044 | | 1/2022 |
| CN | 113907838 | | 1/2022 |
| CN | 113951972 | A | 1/2022 |
| CN | 113951973 | A | 1/2022 |
| CN | 113974765 | | 1/2022 |
| CN | 113974826 | A | 1/2022 |
| CN | 215384399 | | 1/2022 |
| CN | 215386905 | | 1/2022 |
| CN | 215458400 | | 1/2022 |
| CN | 215458401 | | 1/2022 |
| CN | 215505065 | | 1/2022 |
| CN | 215534803 | | 1/2022 |
| CN | 215537694 | | 1/2022 |
| CN | 215584286 | | 1/2022 |
| CN | 215606068 | | 1/2022 |
| CN | 215651393 | | 1/2022 |
| CN | 215651394 | | 1/2022 |
| CN | 215651484 | | 1/2022 |
| CN | 215653328 | | 1/2022 |
| CN | 114053552 | | 2/2022 |
| CN | 115175625 | | 10/2022 |
| DE | 3038445 | A1 | 5/1982 |
| DE | 3836337 | A1 | 4/1990 |
| DE | 3913027 | A1 | 10/1990 |
| DE | 69431758 | | 1/2003 |
| DE | 10230626 | | 1/2004 |
| DE | 202008016760 | | 3/2009 |
| DE | 102007046902 | | 4/2009 |
| DE | 102008034702 | | 1/2010 |
| DE | 102009007129 | | 8/2010 |
| DE | 202010009899 | | 11/2010 |
| DE | 102013201928 | | 8/2014 |
| DE | 102020117713 | | 1/2022 |
| EP | 0119296 | | 9/1984 |
| EP | 0261831 | A2 † | 6/1992 |
| EP | 0261831 | B1 | 6/1992 |
| EP | 558297 | A2 | 9/1993 |
| EP | 0571306 | A1 † | 11/1993 |
| EP | 1179993 | A1 | 2/2002 |
| EP | 1946712 | | 7/2008 |
| EP | 1946712 | A1 | 7/2008 |
| EP | 1453566 | | 9/2008 |
| EP | 2157569 | | 2/2010 |
| EP | 2879595 | | 6/2015 |
| EP | 2879595 | A1 | 6/2015 |
| EP | 2944264 | A1 | 6/2015 |
| EP | 3226795 | A1 | 10/2017 |
| EP | 3266487 | | 1/2018 |
| EP | 3318204 | | 5/2018 |
| EP | 2879607 | | 2/2019 |
| EP | 3461438 | A1 | 4/2019 |
| EP | 3473195 | A1 | 4/2019 |
| EP | 3643260 | A1 | 4/2020 |
| EP | 3076881 | B1 | 1/2022 |
| EP | 3932342 | | 1/2022 |
| EP | 3936140 | | 1/2022 |
| EP | 3960099 | | 3/2022 |
| EP | 4051154 | | 9/2022 |
| EP | 4129213 | | 2/2023 |
| EP | 4277537 | | 11/2023 |
| EP | 4297669 | | 1/2024 |
| EP | 3182931 | | 6/2024 |
| EP | 3950036 | | 8/2024 |
| GB | 1082397 | | 9/1967 |
| JP | S62-275446 | † | 11/1987 |
| JP | S62275446 | A | 11/1987 |
| JP | 1996089511 | | 4/1996 |
| JP | H09117407 | | 5/1997 |
| JP | 2004519296 | | 7/2004 |
| JP | 2008506447 | | 3/2008 |
| JP | 2008083273 | | 4/2008 |
| JP | 2009519777 | | 5/2009 |
| JP | 2009213589 | | 9/2009 |
| JP | 2011524203 | | 9/2011 |
| JP | 4805208 | | 11/2011 |
| JP | 4808620 | | 11/2011 |
| JP | 2014123147 | | 7/2014 |
| JP | 2015217215 | | 12/2015 |

(56) References Cited

FOREIGN PATENT DOCUMENTS

| | | |
|---|---|---|
| JP | 2018538077 | 12/2018 |
| JP | 2024511710 | 3/2024 |
| KR | 20050098932 | 10/2005 |
| KR | 20080040111 | 5/2008 |
| KR | 20160090877 A | 8/2016 |
| KR | 20180054041 | 5/2018 |
| WO | WO9007904 A1 | 7/1990 |
| WO | WO9105332 A1 | 4/1991 |
| WO | 9203095 A1 | 3/1992 |
| WO | WO9208515 | 5/1992 |
| WO | WO9524867 | 9/1995 |
| WO | 9902095 A1 | 1/1999 |
| WO | 1999002095 A1 | 1/1999 |
| WO | 9920189 A1 | 4/1999 |
| WO | 1999020189 A1 | 4/1999 |
| WO | WO200067648 | 11/2000 |
| WO | WO2000067648 A1 | 11/2000 |
| WO | WO0103599 | 1/2001 |
| WO | WO0103599 A2 | 1/2001 |
| WO | 20060006169 A2 | 1/2006 |
| WO | WO2006006169 | 1/2006 |
| WO | WO2009121017 | 10/2009 |
| WO | WO2009149321 A1 | 12/2009 |
| WO | WO2009152352 A2 | 12/2009 |
| WO | 2010042653 A1 | 4/2010 |
| WO | WO2011094379 | 8/2011 |
| WO | 20110126580 A2 | 10/2011 |
| WO | WO2011126580 A3 | 10/2011 |
| WO | WO2012025833 | 3/2012 |
| WO | WO2012042619 | 4/2012 |
| WO | WO20120052924 A1 | 4/2012 |
| WO | WO2012058156 | 5/2012 |
| WO | WO2012099974 A2 | 7/2012 |
| WO | WO20120120495 A2 | 9/2012 |
| WO | WO2013119662 | 8/2013 |
| WO | 20130169807 A1 | 11/2013 |
| WO | WO2013169807 | 11/2013 |
| WO | WO2014022436 A1 | 2/2014 |
| WO | WO2014025397 A1 | 2/2014 |
| WO | WO20140022867 A1 | 2/2014 |
| WO | WO2014138582 | 9/2014 |
| WO | WO2015056662 | 4/2015 |
| WO | WO2015097251 A2 | 7/2015 |
| WO | 20150177790 A1 | 11/2015 |
| WO | WO2016014999 | 1/2016 |
| WO | WO2016089683 A1 | 6/2016 |
| WO | WO2016090175 | 6/2016 |
| WO | WO2016098670 | 6/2016 |
| WO | WO2016109739 | 7/2016 |
| WO | WO2016143556 | 9/2016 |
| WO | WO2016151595 A1 | 9/2016 |
| WO | WO2017004432 A1 | 1/2017 |
| WO | WO20170192869 A1 | 11/2017 |
| WO | 20180022641 A1 | 2/2018 |
| WO | WO2018022593 A1 | 2/2018 |
| WO | WO2018083666 | 5/2018 |
| WO | 20180175322 A1 | 9/2018 |
| WO | WO2018175322 | 9/2018 |
| WO | WO2018191013 | 10/2018 |
| WO | WO2019200201 A1 | 10/2019 |
| WO | WO2019215869 A1 | 11/2019 |
| WO | WO2019222843 | 11/2019 |
| WO | WO2020056031 | 3/2020 |
| WO | WO20200086361 A1 | 4/2020 |
| WO | WO2020089876 A1 | 5/2020 |
| WO | WO2020157648 | 8/2020 |
| WO | WO2020256898 | 12/2020 |
| WO | WO2020256898 A1 | 12/2020 |
| WO | WO2020256949 | 12/2020 |
| WO | WO2020256949 A1 | 12/2020 |
| WO | WO2020263469 A1 | 12/2020 |
| WO | WO2020263685 A1 | 12/2020 |
| WO | WO2020263687 A1 | 12/2020 |
| WO | WO2020263688 A1 | 12/2020 |
| WO | WO2020263689 A1 | 12/2020 |
| WO | WO2021061451 | 4/2021 |
| WO | WO2021067563 | 4/2021 |
| WO | WO2021086571 A1 | 5/2021 |
| WO | WO2021096922 A1 | 5/2021 |
| WO | WO2021101766 | 5/2021 |
| WO | WO2021101766 A1 | 5/2021 |
| WO | WO2021126762 | 6/2021 |
| WO | WO2021162855 A1 | 8/2021 |
| WO | WO2021173417 A1 | 9/2021 |
| WO | WO2021183367 A1 | 9/2021 |
| WO | WO2021183401 A1 | 9/2021 |
| WO | WO2021188233 A1 | 9/2021 |
| WO | WO2021202248 A1 | 10/2021 |
| WO | WO2021231178 A1 | 11/2021 |
| WO | WO2021247685 A1 | 12/2021 |
| WO | WO2021257425 A1 | 12/2021 |
| WO | WO2022007490 | 1/2022 |
| WO | WO2022008440 | 1/2022 |
| WO | WO2022010767 A1 | 1/2022 |
| WO | WO2022055784 | 3/2022 |
| WO | WO2022125525 | 6/2022 |
| WO | WO2022154954 | 7/2022 |
| WO | WO2022173719 | 8/2022 |
| WO | WO2022183075 | 9/2022 |
| WO | WO2022187058 | 9/2022 |
| WO | WO2022216488 | 10/2022 |
| WO | WO2022240674 | 11/2022 |
| WO | WO2022260932 | 12/2022 |
| WO | WO2023107334 | 6/2023 |

OTHER PUBLICATIONS

International Search Report and Written Opinion dated Jun. 27, 2022, in PCT Application Serial No. PCT/US2022/022460.
Medlight, "Cylindrical light diffuser Model RD-ML", Medlight S.A., Switzerland. 2015. (This reference was cited in a prior Information Disclosure Statement. However, the relevant date was missing. The date has now been added.).
Medlight, "Cylindircal light diffuser Model RD", Medlight S.A., Switzerland. 2015. (This reference was cited in a prior Information Disclosure Statement. However, the relevant date was missing. The date has now been added.).
Ohl, Siew-Wan, et al. "Bubbles with shock waves and ultrasound: a review", Interface Focus, pp. 1-15, vol. 5, The Royal Society Publishing. Oct. 2015. (This reference was cited in a prior Information Disclosure Statement. However, the relevant date was missing. The date has now been added.).
Schafter+Kirchhoff, Laser Beam Couplers series 60SMS for coupling into single-mode and polarization-maintaining fiber cables, Schafter+Kirchhoff, pp. 1-5, Germany. Dec. 2, 2021. (This reference was cited in a prior Information Disclosure Statement. However, the relevant date was missing. The date has now been added.).
Meng et al., "Accurate Recovery Of Atrial Endocardial Potential Maps From Non-contact Electrode Data." Auckland Bioengineering Institute. (ID 1421). May 2019. (This reference was cited in a prior Information Disclosure Statement. However, the relevant date was missing. The date has now been added.).
Jiang et al., "Multielectrode Catheter For Substrate Mapping For Scar-related VT Ablation: A Comparison Between Grid Versus Linear Configurations." UChicago Medicine, Center for Arrhythmia Care, Chicago IL (ID 1368). Poster for conference in San Francisco, May 8-11, 2019. (This reference was cited in a prior Information Disclosure Statement. However, the relevant date was missing. The date has now been added.).
Sacher et al., "Comparison Of Manual Vs Automatic Annotation To Identify Abnormal Substrate For Scar Related VT Ablation." Liryc Institute, Bordeaux University Hospital, France (ID 1336). Poster for conference in San Francisco, May 8-11, 2019. (This reference was cited in a prior Information Disclosure Statement. However, the relevant date was missing. The date has now been added.).
International Search Report and Written Opinion, issued by the EP/ISA, in PCT/US2021/048819, dated Jan. 14, 2022.
International Search Report and Written Opinion dated Aug. 20, 2021 in PCT Application Serial No. PCT/US2021/031130.

(56) References Cited

OTHER PUBLICATIONS

International Search Report and Written Opinion, PCT Application Serial No. PCT/US2022/047751 issued Feb. 10, 2023, by the European Patent Office.
International Search Report and Written Opinion dated Aug. 25, 2022 in PCT Application Serial No. PCT US/2022/028035.
International Search Report and Written Opinion dated Sep. 15, 2022 in PCT Application Serial No. PCT US/2022/032045.
International Search Report and Written Opinion, issued by the European Patent Office for PCT/2021/XXX, dated Sep. 30, 2021.
International Search Report and Written Opinion dated Nov. 8, 2022 in PCT Application Serial No. PCT US/2022/039678.
International Search Report and Written Opinion dated Apr. 4, 2022 in PCT Application Serial No. PCT/US2021/062170.
International Search Report and Written Opinion dated Apr. 4, 2022 in PCT Application Serial No. PCT/US2021/065073.
Partial Search Report and Provisional Opinion dated May 3, 2022 in PCT Application No. PCT/ US2022/015577.
International Search Report and Written Opinion dated May 13, 2022 in PCT Application Serial No. PCT/US2022/017562.
Vogel, A., et al. "Intraocular Photodisruption With Picosecond and Nanosecond Laser Pulses: Tissue Effects in Cornea, Lens, and Retina", Investigative Ophthalmology & Visual Science, Jun. 1994, pp. 3032-3044, vol. 35, No. 7, Association for Research in Vision and Ophthalmology.
Jones, H. M., et al. "Pulsed dielectric breakdown of pressurized water and salt solutions", Journal of Applied Physics, Jun. 1998, pp. 795-805, vol. 77, No. 2, American Institute of Physics.
Kozulin, I., et al. "The dynamic of the water explosive vaporization on the flat microheater", Journal of Physics: Conference Series, 2018, pp. 1-4, IOP Publishing, Russia.
Cross, F., "Laser Angioplasty", Vascular Medicine Review, 1992, pp. 21-30, Edward Arnold.
Doukas, A. G., et al. "Laser-generated stress waves and their effects on the cell membrane", IEEE Journal of Selected Topics in Quantum Electronics, 1999, pp. 997-1003, vol. 5, Issue 4, IEEE.
Noack, J., et al. "Laser-Induced Plasma Formation in Water at Nanosecond to Femtosecond Time Scales: Calculation of Thresholds, Absorption Coefficients, and Energy Density", IEEE Journal of Quantum Electronics, 1999, pp. 1156-1167, vol. 35, No. 8, IEEE.
Pratsos, A., "The use of Laser for the treatment of coronary artery disease", Bryn Mawr Hospital, 2010.
Li, Xian-Dong, et al. "Influence of deposited energy on shock wave induced by underwater pulsed current discharge", Physics of Plasmas, 2016, vol. 23, American Institute of Physics.
Logunov, S., et al. "Light diffusing optical fiber illumination", Renewable Energy and the Environment Congress, 2013, Corning, NY, USA.
Maxwell, A. D., et al. "Cavitation clouds created by shock scattering from bubbles during histotripsy", Acoustical Society of America, 2011, pp. 1888-1898, vol. 130, No. 4, Acoustical Society of America.
McAteer, James A., et al. "Ultracal-30 Gypsum Artificial Stones For Research On The Mechinisms Of Stone Breakage In Shock Wave Lithotripsy", 2005, pp. 429-434, Springer-Verlag.
Vogel, A., et al. "Mechanisms of Intraocular Photodisruption With Picosecond and Nanosecond Laser Pulses", Lasers in Surgery and Medicine, 1994, pp. 32-43, vol. 15, Wiley-Liss Inc., Lubeck, Germany.
Vogel, A., et al. "Mechanisms of Pulsed Laser Ablation of Biological Tissues", Chemical Reviews, 2003, pp. 577-644, vol. 103, No. 2, American Chemical Society.
Medlight, "Cylindrical light diffuser Model RD-ML", Medlight S.A., Switzerland.
Medlight, "Cylindircal light diffuser Model RD", Medlight S.A., Switzerland.
Mayo, Michael E., "Interaction of Laser Radiation with Urinary Calculi", Cranfield University Defense and Security, PhD Thesis, 2009, Cranfield University.
Vogel, A., et al. "Minimization of Cavitation Effects in Pulsed Laser Ablation Illustrated on Laser Angioplasty", Applied Physics, 1996, pp. 173-182, vol. 62, Springer-Verlag.
Mirshekari, G., et al. "Microscale Shock Tube", Journal of Microelectromechanical Systems, 2012, pp. 739-747, vol. 21, No. 3, IEEE.
"Polymicro Sculpted Silica Fiber Tips", Molex, 2013, Molex.
Zhou, J., et al. "Optical Fiber Tips and Their Applications", Polymicro Technologies A Subsidiary of Molex, Nov. 2007.
Liang, Xiao-Xuan, et al. "Multi-Rate-Equation modeling of the energy spectrum of laser-induced conduction band electrons in water", Optics Express, 2019, vol. 27, No. 4, Optical Society of America.
Nachabe, R., et al. "Diagnosis of breast cancer using diffuse optical spectroscopy from 500 to 1600 nm: comparison of classification methods", Journal of Biomedical Optics, 2011, vol. 16(8), SPIE.
Naugol'nykh, K. A., et al. "Spark Discharges in Water", Academy of Sciences USSR Institute of Acoustics, 1971, Nauka Publishing Co., Moscow, USSR.
Van Leeuwen, Ton G., et al. "Noncontact Tissue Ablation by Holmium: YSGG Laser Pulses in Blood", Lasers in Surgery and Medicine, 1991, vol. 11, pp. 26-34, Wiley-Liss Inc.
Nyame, Yaw A., et al. "Kidney Stone Models for In Vitro Lithotripsy Research: A Comprehensive Review", Journal of Endourology, Oct. 2015, pp. 1106-1109, vol. 29, No. 10, Mary Ann Liebert Inc., Cleveland, USA.
Ohl, Siew-Wan, et al. "Bubbles with shock waves and ultrasound: a review", Interface Focus, pp. 1-15, vol. 5, The Royal Society Publishing.
Zheng, W., "Optical Lenses Manufactured on Fiber Ends", IEEE, 2015, Splicer Engineering, Duncan SC USA.
Dwyer, P. J., et al. "Optically integrating balloon device for photodynamic therapy", Lasers in Surgery and Medicine, 2000, pp. 58-66, vol. 26, Issue 1, Wiley-Liss Inc., Boston MA USA.
"The New Optiguide DCYL700 Fiber Optic Diffuser Series", Optiguide Fiber Optic Spec Sheet, Pinnacle Biologics, 2014, Pinnacle Biologics, Illinois, USA.
Van Leeuwen, Ton G., et al. "Origin of arterial wall dissections induced by pulsed excimer and mid-infared laser ablation in the pig", JACC, 1992, pp. 1610-1618, vol. 19, No. 7, American College of Cardiology.
Oshita, D., et al. "Characteristic of Cavitation Bubbles and Shock Waves Generated by Pulsed Electric Discharges with Different Voltages", IEEE, 2012, pp. 102-105, Kumamoto, Japan.
Karsch, Karl R., et al. "Percutaneous Coronary Excimer Laser Angioplasty in Patients With Stable and Unstable Angina Pectoris", Circulation, 1990, pp. 1849-1859, vol. 81, No. 6, American Heart Association, Dallas TX, USA.
Murray, A., et al. "Peripheral laser angioplasty with pulsed dye laser and ball tipped optical fibres", The Lancet, 1989, pp. 1471-1474, vol. 2, Issue 8678-8679.
Mohammadzadeh, M., et al. "Photoacoustic Shock Wave Emission and Cavitation from Structured Optical Fiber Tips", Applied Physics Letters, 2016, vol. 108, American Institute of Physics Publishing LLC.
Doukas, A. G., et al. "Physical characteristics and biological effects of laser-induced stress waves", Ultrasound in Medicine and Biology, 1996, pp. 151-164, vol. 22, Issue 2, World Federation for Ultrasound in Medicine and Biology, USA.
Doukas, A. G., et al. "Physical factors involved in stress-wave-induced cell injury: the effect of stress gradient", Ultrasound in Medicine and Biology, 1995, pp. 961-967, vol. 21, Issue 7, Elsevier Science Ltd., USA.
Piedrahita, Francisco S., "Experimental Research Work On A Sub-Millimeter Spark-Gap For Sub Nanosecond Gas Breakdown", Thesis for Universidad Nacional De Colombia, 2012, Bogota, Colombia.
Vogel, A., et al. "Plasma Formation in Water by Picosecond and Nanosecond Nd: YAG Laser Pulses—Part I: Optical Breakdown at Threshold and Superthreshold Irradiance", IEEE Journal of Selected Topics in Quantum Electronics, 1996, pp. 847-859, vol. 2, No. 4, IEEE.

(56) References Cited

OTHER PUBLICATIONS

Park, Hee K., et al. "Pressure Generation and Measurement in the Rapid Vaporization of Water on a Pulsed-Laser-Heated Surface", Journal of Applied Physics, 1996, pp. 4072-4081, vol. 80, No. 7, American Institute of Physics.

Cummings, Joseph P., et al. "Q-Switched laser ablation of tissue: plume dynamics and the effect of tissue mechanical properties", SPIE, Laser-Tissue Interaction III, 1992, pp. 242-253, vol. 1646.

Lee, Seung H., et al. "Radial-firing optical fiber tip containing conical-shaped air-pocket for biomedical applications", Optics Express, 2015, vol. 23, No. 16, Optical Society of America.

Hui, C., et al. "Research on sound fields generated by laser-induced liquid breakdown", Optica Applicata, 2010, pp. 898-907, vol. XL, No. 4, Xi'an, China.

Riel, Louis-Philippe, et al. "Characterization of Calcified Plaques Retrieved From Occluded Arteries and Comparison with Potential Artificial Analogues", Proceedings of the ASME 2014 International Mechanical Engineering Congress and Exposition, 2014, pp. 1-11, ASME, Canada.

Roberts, Randy M., et al. "The Energy Partition of Underwater Sparks", The Journal of the Acoustical Society of America, 1996, pp. 3465-3475, vol. 99, No. 6, Acoustical Society of America.

Rocha, R., et al. "Fluorescence and Reflectance Spectroscopy for Identification of Atherosclerosis in Human Carotid Arteries Using Principal Components Analysis", Photomedicine and Lsser Surgery, 2008, pp. 329-335, vol. 26, No. 4, Mary Ann Liebert Inc.

Scepanovic, Obrad R., et al. "Multimodal spectroscopy detects features of vulnerable atherosclerotic plaque", Journal of Biomedical Optics, 2011, pp. 1-10, vol. 16, No. 1, SPIE.

Serruys, P. W., et al. "Shaking and Breaking Calcified Plaque Lithoplasty, a Breakthrough in Interventional Armamentarium?", JACC: Cardiovascular Imaging, 2017, pp. 907-911, vol. 10, No. 8, Elsevier.

Vogel, A., et al. "Shock wave emission and cavitation bubble generation by picosecond and nanosecond optical breakdown in water", The Journal of the Acoustical Society of America, 1996, pp. 148-165, vol. 100, No. 1, Acoustical Society of America.

Vogel, A., et al. "Shock-Wave Energy and Acoustic Energy Dissipation After Laser-induced Breakdown", SPIE, 1998, pp. 180-189, vol. 3254, SPIE.

International Preliminary Report on Patentability dated Sep. 15, 2020 in PCT Application Serial No. PCT/US2019/022009.

International Search Report and Written Opinion dated Sep. 14, 2020 in PCT Application Serial No. PCT/US2020/038523.

International Search Report and Written Opinion dated Oct. 2, 2020 in PCT Application Serial No. PCT/US2020/036107.

Schafter+Kirchhoff, Laser Beam Couplers series 60SMS for coupling into single-mode and polarization-maintaining fiber cables, Schafter+Kirchhoff, pp. 1-5, Germany.

International Search Report and Written Opinion dated Jan. 29, 2020 in PCT Application Serial No. PCT/US2020/059961.

International Search Report and Written Opinion dated Jan. 20, 2020 in PCT Application Serial No. PCT/US2020/054792.

Partial Search Report and Provisional Opinion dated Feb. 19, 2021 in PCT Application Serial No. PCT/US2020/059960.

Shariat, Mohammad H., et al. "Localization of the ectopic spiral electrical source using intracardiac electrograms during atrial fibrillation." 2015 IEEE 28th Canadian Conference on Electrical and Computer Engineering (CCECE). IEEE, 2015.

Nademanee, Koonlawee, et al. "A new approach for catheter ablation of atrial fibrillation: mapping of the electrophysiologic substrate." Journal of the American College of Cardiology 43.11 (2004): 2044-2053.

Calkins, Hugh. "Three dimensional mapping of atrial fibrillation: techniques and necessity." Journal of interventional cardiac electrophysiology 13.1 (2005): 53-59.

Shariat, Mohammad Hassan. Processing the intracardiac electrogram for atrial fibrillation ablation. Diss. Queen's University (Canada), 2016.

Meng et al., "Accurate Recovery Of Atrial Endocardial Potential Maps From Non-contact Electrode Data." Auckland Bioengineering Institute. (ID 1421).

Jiang et al., "Multielectrode Catheter For Substrate Mapping For Scar-related VT Ablation: A Comparison Between Grid Versus Linear Configurations." UChicago Medicine, Center for Arrhythmia Care, Chicago IL (ID 1368).

Sacher et al., "Comparison Of Manual Vs Automatic Annotation To Identify Abnormal Substrate For Scar Related VT Ablation." Liryc Institute, Bordeaux University Hospital, France (ID 1336).

Oriel Instruments, "Introduction to Beam Splitters for Optical Research Applications", Apr. 2014, pp. 1-9, https://www.azoptics.com/Article.aspx?ArticaID=871.

International Search Report and Written Opinion dated Apr. 12, 2021 in PCT Application Serial No. PCT/US2020/059960.

International Search Report and Written Opinion dated Apr. 13, 2021 in PCT Application Serial No. PCT/US2020/064846.

International Search Report and Written Opinion dated Apr. 13, 2021 in PCT Application Serial No. PCT/US2021/013944.

International Search Report and Written Opinion dated May 25, 2021 in PCT Application Serial No. PCT/US2021/017604.

International Search Report and Written Opinion dated Jun. 2, 2021 in PCT Application Serial No. PCT/US2021/018522.

International Search Report and Written Opinion dated Jun. 2, 2021 in PCT Application Serial No. PCT/US2021/015204.

International Search Report and Written Opinion dated Jun. 17, 2021 in PCT Application Serial No. PCT/US2021/020934.

International Search Report and Written Opinion dated Jul. 13, 2021 in PCT Application Serial No. PCT/US2021/024216.

International Search Report and Written Opinion dated Jun. 22, 2021 in PCT Application Serial No. PCT/US2021/020937.

International Search Report and Written Opinion dated Jun. 24, 2021 in PCT Application Serial No. PCT/US2021/021272.

Stelzle, F., et al. "Diffuse Reflectance Spectroscopy for Optical Soft Tissue Differentiation as Remote Feedback Control for Tissue-Specific Laser Surgery", Lasers in Surgery and Medicine, 2010, pp. 319-325, vol. 42, Wiley-Liss Inc.

Stelzle, F., et al. Tissue Discrimination by Uncorrected Autofluorescence Spectra: A Proof-of-Principle Study for Tissue-Specific Laser Surgery, Sensors, 2013, pp. 13717-13731, vol. 13, Basel, Switzerland.

Tagawa, Y., et al. "Structure of laser-induced shock wave in water", Japan Society for the Promotion of Science, 2016.

Shen, Y., et al. "Theoretical and experimental studies of directivity of sound field generated by pulsed laser induced breakdown in liquid water", SPIE, 2013, pp. 8796141-8796148, vol. 8796, SPIE.

Preisack, M., et al. "Ultrafast imaging of tissue ablation by a XeCl excimer laser in saline", Lasers in Surgery and Medicine, 1992, pp. 520-527, vol. 12, Wiley-Liss Inc.

Versluis, M., et al. "How Snapping Shrimp Snap: Through Cavitating Bubbles", Science Mag, 2000, pp. 2114-2117, vol. 289, American Association for the Advancement of Science, Washington DC, USA.

Yan, D., et al. "Study of the Electrical Characteristics, Shock-Wave Pressure Characteristics, and Attenuation Law Based on Pulse Discharge in Water", Shock and Vibration, 2016, pp. 1-11, vol. 2016, Article ID 6412309, Hindawi Publishing Corporation.

Zhang, Q., et al. "Improved Instruments and Methods for the Photographic Study of Spark-Induced Cavitation Bubbles", Water, 2018, pp. 1-12, vol. 10, No. 1683.

"Damage threshold of fiber facets", NKT Photonics, 2012, pp. 1-4, Denmark.

Smith, A., et al. "Bulk and surface laser damage of silica by picosecond and nanosecond pulses at 1064 nm", Applied Optics, 2008, pp. 4812-4832, vol. 47, No. 26, Optical Society of America.

Smith, A., et al. "Deterministic Nanosecond Laser-Induced Breakdown Thresholds In Pure and Yb3 Doped Fused Silica", SPIE, 2007, pp. 6453171-64531712, vol. 6453, SPIE.

Sun, X., et al. "Laser Induced Damage to Large Core Optical Fiber by High Peak Power Laser", Specialty Photonics Division, 2010.

Smith, A., et al. "Nanosecond laser-induced breakdown in pure and Yb3 doped fused silica", SPIE, 2007, vol. 6403, SPIE.

(56) References Cited

OTHER PUBLICATIONS

Smith, A., et al. "Optical Damage Limits to Pulse Energy From Fibers", IEEE Journal of Selected Topics in Quantum Electronics, 2009, pp. 153-158, vol. 15, No. 1, IEEE.
Reichel, E., et al. "A Special Irrigation Liquid to Increase the Reliability of Laser-Induced Shockwave Lithotripsy", Lasers in Surgery and Medicine, 1992, pp. 204-209, vol. 12, Wiley-Liss Inc., Graz, Austria.
Reichel, E., et al. "Bifunctional irrigation liquid as an ideal energy converter for laser lithotripsy with nanosecond laser pulses", SPIE Lasers in Urology, Laparoscopy, and General Surgery, 1991, pp. 129-133, vol. 1421, SPIE.
Reichel, E., et al. "Laser-induced Shock Wave Lithotripsy with a Regenerative Energy Converter", Lasers in Medical Science, 1992, pp. 423-425, vol. 7, Bailliere Tindall.
Hardy, L., et al. "Cavitation Bubble Dynamics during Thulium Fiber Laser Lithotripsy", SPIE BiOS, 2016, vol. 9689, SPIE.
Deckelbaum, L., "Coronary Laser Angioplasty", Lasers in Surgery and Medicine, 1994, pp. 101-110, vol. 14, Wiley-Liss Inc., Conneticuit, USA.
Shangguan, H., et al. "Effects of Material Properties on Laser-induced Bubble Formation in Absorbing Liquids and On Submerged Targets", Diagnostic and Therapeutic Cardiovascular Interventions VII, SPIE, 1997, pp. 783-791, vol. 2869, SPIE.
Van Leeuwen, T., et al. "Excimer Laser Induced Bubble: Dimensions, Theory, and Implications for Laser Angioplasty", Lasers in Surgery and Medicine, 1996, pp. 381-390, vol. 18, Wiley-Liss Inc., The Netherlands.
Vogel, A., et al. "Shock Wave Emission and Cavitation Bubble Generation by Picosecond and Nanosecond Optical Breakdown in Water", The Journal of Acoustical Society of America, 1996, pp. 148-165, vol. 100, No. 1, The Acoustical Society of America.
Varghese, B., et al. "Influence of absorption induced thermal initiation pathway on irradiance threshold for laser induced breakdown", Biomedical Optics Express, 2015, vol. 6, No. 4, Optical Society of America.
Linz, N., et al. "Wavelength dependence of nanosecond infrared laser-induced breakdown in water: Evidence for multiphoton initiation via an intermediate state", Physical Review, 2015, pp. 134114.1-1341141.10, vol. 91, American Physical Society.
International Search Report and Written Opinion dated Jun. 27, 2018, in PCT Application Serial No. PCT/US2018/027121.
International Search Report and Written Opinion dated Jul. 20, 2018, in PCT Application Serial No. PCT/US2018/027801.
International Search Report and Written Opinion dated Jul. 20, 2018, in PCT Application Serial No. PCT/US2018/027784.
European Search Report, for European Patent Application No. 18185152, mailed Dec. 13, 2018.
International Search Report and Written Opinion dated May 22, 2019, in PCT Application Serial No. PCT/US2019/022009.
International Search Report and Written Opinion dated May 29, 2019, in PCT Application Serial No. PCT/US2019/022016.
International Search Report and Written Opinion dated Jun. 22, 2018, in Application Serial No. NL2019807, issued by the European Patent Office.
Noimark, Sacha, et al., "Carbon-Nanotube-PDMS Composite Coatings on Optical Fibers for All-Optical Ultrasound Imaging", Advanced Functional Materials, 2016, pp. 8390-8396, vol. 26, Wiley-Liss Inc.
Chen, Sung-Liang, "Review of Laser-Generated Ultrasound Transmitters and their Applications to All-Optical Ultrasound Transducers and Imaging", Appl. Sci. 2017, 7, 25.
Colchester, R., et al. "Laser-Generated ultrasound with optica fibres using functionalised carbon nanotube composite coatings", Appl. Phys. Lett., 2014, vol. 104, 173504, American Institute of Physics.
Poduval, R., et al. "Optical fiber ultrasound transmitter with electrospun carbon nanotube-polymer composite", Appl. Phys. Lett., 2017, vol. 110, 223701, American Institute of Physics.
Tian, J., et al. "Distributed fiber-optic laser-ultrasound generation based on ghost-mode of tilted fiber Bragg gratings", Optics Express, Mar. 2013, pp. 6109-6114, vol. 21, No. 5, Optical Society of America.
Kim, J., et al. "Optical Fiber Laser-Generated-Focused-Ultrasound Transducers for Intravascular Therapies", IEEE, 2017.
Kang, H., et al. "Enhanced photocoagulation with catheter-based diffusing optical device", Journal of Biomedical Optics, 2012, vol. 17, Issue 11, 118001, SPIE.
International Search Report and Written Opinion dated Jan. 3, 2020, in PCT Application Serial No. PCT/US2019/056579.
Communication Pursuant to Article 94(3) EPC, for European Patent Application No. 18185152.8, mailed Jan. 16, 2019.
European Search Report, for European Patent Application No. 18185152.8, mailed Dec. 20, 2018.
International Search Report and Written Opinion dated Jul. 29, 2020 in PCT Application Serial No. PCT/US2020/034005.
International Search Report and Written Opinion dated Sep. 11, 2020 in PCT Application Serial No. PCT/US2020/038517.
International Search Report and Written Opinion dated Sep. 9, 2020 in PCT Application Serial No. PCT/US2020/038530.
International Search Report and Written Opinion dated Sep. 11, 2020 in PCT Application Serial No. PCT/US2020/038521.
International Search Report and Written Opinion dated Sep. 7, 2020 in PCT Application Serial No. PCT/US2020/034642.
Shen, Yajie et al. "High-peak-power and narrow-linewidth Q-switched Ho: YAG laser in-band pumped at 1931 nm." Applied Physics Express 13.5 (2020): 052006. (Year 2020).
PathFinder Digital, "Free Space Optics vs. Fiber Optics", 2023.
International Search Report and Written Opinion, issued in Application Serial No. PCT/US2023/016152, dated Jul. 12, 2023.
AccuCoat, "Beamsplitter: Divide, combine & conquer"; 2023.
Lin et al., "Photoacoustic imaging", Science Direct; 2021.
Zhou et al., "Photoacoustic Imaging with fiber optic technology: A review", Science Direct; 2020.
International Search Report and Written Opinion issued by the European Patent Office, for Serial No. PCT/US2022/053775, dated Apr. 21, 2023.
International Search Report and Written Opinion issued by the European Patent Office, for Serial No. PCT/US2023/011497, dated Apr. 28, 2023.
International Search Report and Written Opinion issued by the European Patent Office, for Serial No. PCT/US2023/012599, dated May 19, 2023.
"Custom Medical Skived Tubing", Duke Extrusion, 2025. https://www.dukeextrusion.com/tubing-options/skived-tubing.
Davletshin, Yevgeniy R., "A Computational Analysis of Nanoparticle-Mediated Optical Breakdown", A dissertation presented to Ryerson University in Partial Fulfillment of the requirements for the degree of Doctor of Philosophy in the Program of Physics, Toronto, Ontario, CA 2017.
Vogel, A., et al. "Acoustic transient generation by laser-produced cavitation bubbles near solid boundaries", Journal Acoustical Society of America, 1988, pp. 719-731, vol. 84.
Asshauer, T., et al. "Acoustic transient generation by holmium-laser-induced cavitation bubbles", Journal of Applied Physics, Nov. 1, 1994, pp. 5007-5013, vol. 76, No. 9, American Institute of Physics.
Zheng, W., "Optic Lenses Manufactured on Fiber Ends", 2015, Splicer Engineering AFL, Duncan, SC USA.
Ali, Ziad A., et al. "Optical Coherence Tomography Characterization of Coronary Lithoplasty for Treatment of Calcified Lesions", JACC: Cardiovascular Imaging, 2017, pp. 897-906, vol. 109, No. 8, Elsevier.
Ali, Ziad A., et al. "Intravascular lithotripsy for treatment of stent underexpansion secondary to severe coronary calcification" 2018, European Society of Cardiology.
Ashok, Praveen C., et al. "Raman spectroscopy bio-sensor for tissue discrimination in surgical robotics—full article", Journal of Biophotonics, 2014, pp. 103-109, vol. 7, No. 1-2.
Ashok, Praveen C., et al. "Raman spectroscopy bio-sensor for tissue discrimination in surgical robotics—proof" Journal of Biophotonics 7, 2014, No. 1-2.

(56) References Cited

OTHER PUBLICATIONS

Bian, D. C., et al. "Experimental Study of Pulsed Discharge Underwater Shock-Related Properties in Pressurized Liquid Water", Hindawi Advances in Materials Science and Engineering, Jan. 2018, 12 pages, vol. 2018, Article ID 8025708.

Bian, D. C., et al. "Study on Breakdown Delay Characteristics Based on High-voltage Pulse Discharge in Water with Hydrostatic Pressure", Journal of Power Technologies 97(2), 2017, pp. 89-102.

Doukas, A. G., et al. "Biological effects of laser induced shock waves: Structural and functional cell damage in vitro", Ultrasound in Medicine and Biology, 1993, pp. 137-146, vol. 19, Issue 2, Pergamon Press, USA.

Brodmann, Marianne et al. "Safety and Performance of Lithoplasty for Treatment of Calcified Peripheral Artery Lesions", JACC, 2017, vol. 70, No. 7.

Brouillette, M., "Shock Waves at Microscales", 2003, pp. 3-12, Springer-Verlag.

Mirshekari, G., et al. "Shock Waves in Microchannels", 2013, pp. 259-283, vol. 724, Cambridge University Press.

"Bubble Dynamics and Shock Waves", Springer, 2013, Springer-Verlag, Berlin Heildelberg.

Hardy, Luke A., et al. "Cavitation Bubble Dynamics During Thulium Fiber Laser Lithotripsy", SPIE, Feb. 29, 2016, vol. 9689, San Francisco, California, USA.

Claverie, A., et al. "Experimental characterization of plasma formation and shockwave propagation induced by high power pulsed underwater electrical discharge", Review of Scientific Instruments, 2014, American Institute of Physics.

Blackmon, Richard L., et al. "Comparison of holmium: YAG and thulium fiber laser lithotripsy ablation thresholds, ablation rates, and retropulsion effects", Journal of Biomedical Optics, 2011, vol. 16(7), SPIE.

Debasis, P., et al. "Continuous-wave and quasi-continuous wave thulium-doped all-fiber laser: implementation on kidney stone fragmentations", Applied Optics, Aug. 10, 2016, vol. 55, No. 23, Optical Society of America.

Cook, Jason R., et al. "Tissue mimicking phantoms for photoacoustic and ultrasonic imaging", Biomedical Optics Express, 2011, vol. 2, No. 11, Optical Society of America.

Deckelbaum, Lawrence I., "Coronary Laser Angioplasty", Lasers in Surgery and Medicine, 1994, pp. 101-110, Wiley-Liss Inc.

Costanzo, F., "Underwater Explosion Phenomena and Shock Physics", Research Gate, 2011.

Mizeret, J. C., et al. "Cylindrical fiber optic light diffuser for medical applications", Lasers in Surgery and Medicine, 1996, pp. 159-167, vol. 19, Issue 2, Wiley-Liss Inc., Lausanne, Switzerland.

De Silva, K., et al. "A Calcific, Undilatable Stenosis Lithoplasty, a New Tool in the Box?", JACC: Cardiovascular Interventions, 2017, vol. 10, No. 3, Elsevier.

Vesselov, L., et al. "Design and performance of thin cylindrical diffusers created in Ge-doped multimode optical fibers", Applied Optics, 2005, pp. 2754-2758, vol. 44, Issue 14, Optical Society of America.

Hutchens, Thomas C., et al. "Detachable fiber optic tips for use in thulium fiber laser lithotripsy", Journal of Biomedical Optics, Mar. 2013, vol. 18(3), SPIE.

Kostanski, Kris L., et al. "Development of Novel Tunable Light Scattering Coating Materials for Fiber Optic Diffusers In Photodynamic Cancer Therapy", Journal of Applied Polymer Science, 2009, pp. 1516-1523, vol. 112, Wiley InterScience.

Kristiansen, M., et al. "High Voltage Water Breakdown Studies", DoD, 1998, Alexandria, VA, USA.

Dwyer, J. R., et al. "A study of X-ray emission from laboratory sparks in air at atmospheric pressure", Journal of Geophysical Research, 2008, vol. 113, American Geophysical Union.

Jansen, Duco E., et al. "Effect of Pulse Duration on Bubble Formation and Laser-Induced Pressure Waves During Holmium Laser Ablation", Lasers in Surgery and Medicine 18, 1996, pp. 278-293, Wiley-Liss Inc., Austin, TX, USA.

Shangguan, HanQun et al. "Effects of Material Properties on Laser-induced Bubble Formation in Absorbing Liquids and On Submerged Targets", SPIE, 1997, pp. 783-791, vol. 2869.

Varghese, B., et al. "Effects of polarization and absorption on laser induced optical breakdown threshold for skin rejuvenation", SPIE, Mar. 9, 2016, vol. 9740, SPIE, San Francisco, USA.

Varghese, B., et al. "Effects of polarization and apodization on laser induced optical breakdown threshold", Optics Express, Jul. 29, 2013, vol. 21, No. 15, Optical Society of America.

Bonito, Valentina, "Effects of polarization, plasma and thermal initiation pathway on irradiance threshold of laser Induced optical breakdown", Philips Research, 2013, The Netherlands.

Vogel, A. et al. "Energy balance of optical breakdown in water at nanosecond to femtosecond time scales", Applied Physics B 68, 1999, pp. 271-280, Springer-Verlag.

Kang, Hyun W., et al. "Enhanced photocoagulation with catheter based diffusing optical device", Journal of Biomedical Optics, Nov. 2012, vol. 17(11), SPIE.

Esch, E., et al. "A Simple Method For Fabricating Artificial Kidney Stones Of Different Physical Properties", National Institute of Health Public Access Author Manuscript, Aug. 2010.

Isner, Jeffrey M., et al. "Excimer Laser Atherectomy", Circulation, Jun. 1990, vol. 81, No. 6, American Heart Association, Dallas, TX, USA.

Israel, Douglas H., et al. "Excimer Laser-Facilitated Balloon Angioplasty of a Nondilateable Lesion", JACC, Oct. 1991, vol. 18, No. 4, American College of Cardiology, New York, USA.

Van Leeuwen, Ton G., et al. "Excimer Laser Induced Bubble: Dimensions, Theory, and Implications for Laser Angioplasty", Lasers in Surgery and Medicine 18, 1996, pp. 381-390, Wiley-Liss Inc., Utrecht, The Netherlands.

Nguyen, H., et al. "Fabrication of multipoint side-firing optical fiber by laser micro-ablation", Optics Letters, May 1, 2017, vol. 42, No. 9, Optical Society of America.

Zheng, W., "Optic Lenses Manufactured on Fiber Ends", 2015, IEEE, Duncan, SC, USA.

Whitesides, George M., et al. "Fluidic Optics", 2006, vol. 6329, SPIE, Cambridge, MA, USA.

Forero, M., et al. "Coronary lithoplasty: a novel treatment for stent underexpansion", Cardiovascular Flashlight, 2018, European Society of Cardiology.

Ghanate, A. D., et al. "Comparative evaluation of spectroscopic models using different multivariate statistical tools in a multicancer scenario", Journal of Biomedical Optics, Feb. 2011, pp. 1-9, vol. 16(2), SPIE.

Roberts, Randy M., et al. "The Energy Partition of Underwater Sparks", The Journal of the Acoustical Society of America, Jun. 1996, pp. 3465-3474, Acoustical Society of America, Austin, TX, USA.

Blackmon, Richard L., et al. "Holmium: YAG Versus Thulium Fiber Laser Lithotripsy", Lasers in Surgery and Medicine, 2010, pp. 232-236, Wiley-Liss Inc.

Varghese, B., "Influence of absorption induced thermal initiation pathway on irradiance threshold for laser induced breakdown", Biomedical Optics Express, 2015, vol. 6, No. 4, Optical Society of America.

Noack, J., "Influence of pulse duration on mechanical effects after laser-induced breakdown in water", Journal of Applied Physics, 1998, pp. 7488-EOA, vol. 83, American Institute of Physics.

Van Leeuwen, Ton G., et al. "Intraluminal Vapor Bubble Induced by Excimer Laser Pulse Causes Microsecond Arterial Dilation and Invagination Leading to Extensive Wall Damage in the Rabbit", Circulation, Apr. 1993, vol. 87, No. 4, American Heart Association, Dallas, TX, USA.

\* cited by examiner
† cited by third party

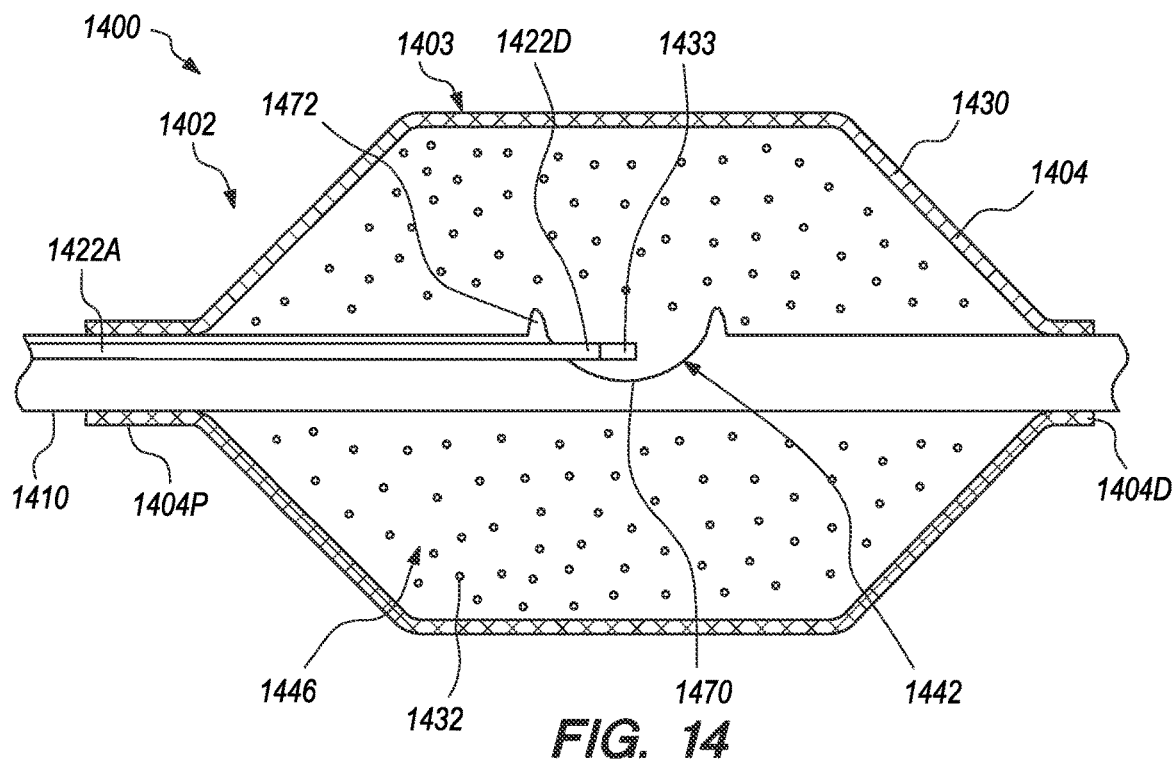

SYSTEM AND METHOD FOR MAINTAINING BALLOON INTEGRITY WITHIN INTRAVASCULAR LITHOTRIPSY DEVICE WITH PLASMA GENERATOR

RELATED APPLICATION

This application claims priority on U.S. Provisional Application Ser. No. 63/033,929, filed on Jun. 3, 2020. To the extent permitted, the contents of U.S. Provisional Application Ser. No. 63/033,929 are incorporated in their entirety herein by reference.

BACKGROUND

Vascular lesions within vessels in the body can be associated with an increased risk for major adverse events, such as myocardial infarction, embolism, deep vein thrombosis, stroke, and the like. Severe vascular lesions, such as severely calcified vascular lesions, can be difficult to treat and achieve patency for a physician in a clinical setting.

Vascular lesions may be treated using interventions such as drug therapy, balloon angioplasty, atherectomy, stent placement, vascular graft bypass, to name a few. Such interventions may not always be ideal or may require subsequent treatment to address the lesion.

Intravascular lithotripsy is one method that has been recently used with some success for breaking up vascular lesions within vessels in the body. Intravascular lithotripsy utilizes a combination of pressure waves and bubble dynamics that are generated intravascularly in a fluid-filled balloon catheter. In particular, during a intravascular lithotripsy treatment, a high energy source is used to generate plasma and ultimately pressure waves as well as a rapid bubble expansion within a fluid-filled balloon to crack calcification at a lesion site within the vasculature. The associated rapid bubble formation from the plasma initiation and resulting localized fluid velocity within the balloon transfers mechanical energy through the incompressible fluid to impart a fracture force on the intravascular calcium, which is opposed to the balloon wall. The rapid change in fluid momentum upon hitting the balloon wall is known as hydraulic shock, or water hammer.

The generation of the plasma within the balloon interior can create a risk of rupture of the balloon due to the extremely high temperatures of the plasma. For example, plasma temperature can be greater than 4000° K, which is significantly higher than the melt temperature of traditional balloon materials. One limitation of creating a plasma within an angioplasty balloon, is risk of balloon rupture if the plasma is in close proximity to the balloon material, as the temperature of the plasma generated within the balloon is typically significantly greater than the melt temperature of traditional balloon materials. This is especially true in tortuous anatomy with severely calcified lesions of minimal lumen diameter such that before therapy, the catheter shaft is in very close proximity or touching the vessel wall. Thus, it is desired to develop means to minimize the possibility of balloon rupture due to the high temperatures of the plasma that is generated within the fluid-filled balloon so as to more effectively maintain catheter integrity.

SUMMARY

The present invention is directed toward a catheter system for placement within a blood vessel or a heart valve. The catheter system can be used for treating a treatment site within or adjacent to the vessel wall or the heart valve. In various embodiments, the catheter system includes an energy source, a balloon, an energy guide, and a balloon integrity protection system. The energy source generates energy. The balloon is positionable substantially adjacent to the treatment site. The balloon has a balloon wall that defines a balloon interior, the balloon being configured to retain a balloon fluid within the balloon interior. The energy guide is configured to receive energy from the energy source and guide the energy into the balloon interior so that plasma is formed in the balloon fluid within the balloon interior. The balloon integrity protection system is operatively coupled to the balloon. The balloon integrity protection system is configured to inhibit rupture of the balloon due to the plasma formed in the balloon fluid within the balloon interior during use of the catheter system.

In some embodiments, the catheter system further includes a plasma generator that is positioned at a guide distal end of the energy guide, the plasma generator being configured to generate the plasma in the balloon fluid within the balloon interior. In some embodiments, the plasma formation causes rapid bubble formation and imparts pressure waves upon the balloon wall adjacent to the treatment site.

In certain embodiments, the energy source generates pulses of energy that are guided along the energy guide into the balloon interior to induce the plasma formation in the balloon fluid within the balloon interior.

In some embodiments, the energy source is a laser source that provides pulses of laser energy. In such embodiments, the energy guide can include an optical fiber.

In certain embodiments, the energy source is a high voltage energy source that provides pulses of high voltage. In such embodiments, the energy guide can include an electrode pair including spaced apart electrodes that extend into the balloon interior; and pulses of high voltage from the energy source can be applied to the electrodes and form an electrical arc across the electrodes.

The present invention is also directed toward a method for treating a treatment site within or adjacent to a vessel wall utilizing the catheter system as described above.

In certain applications, the present invention is directed toward a catheter system for treating a treatment site within or adjacent to a vessel wall or heart valve, the catheter system including an energy source that generates energy; a balloon that is positionable substantially adjacent to the treatment site, the balloon having a balloon wall that defines a balloon interior, the balloon being configured to retain a balloon fluid within the balloon interior; an energy guide that is configured to receive energy from the energy source and guide the energy into the balloon interior so that plasma is formed in the balloon fluid within the balloon interior; and a second balloon that is positioned to substantially completely encircle the balloon, the second balloon including a second balloon wall that is positioned such that a majority of the second balloon wall is positioned spaced apart from the balloon wall.

In some embodiments, the catheter system further includes a cooling fluid that is positioned substantially between the balloon wall and the second balloon wall. In such embodiments, the cooling fluid can be circulated between the balloon wall and the second balloon wall to maintain a balloon temperature of the second balloon wall below a melting temperature of the second balloon. In certain embodiments, the cooling fluid is formed from a mixture of saline and contrast medium. Alternatively, in other embodiments, the cooling fluid is formed from one or more of water, saline, contrast medium, fluorocarbons, perfluorocarbons, and carbon dioxide.

In some applications, the present invention is directed toward a catheter system for treating a treatment site within or adjacent to a vessel wall or heart valve, the catheter system including an energy source that generates energy; a balloon that is positionable substantially adjacent to the treatment site, the balloon having a balloon wall that defines a balloon interior, the balloon being configured to retain a balloon fluid within the balloon interior; an energy guide that is configured to receive energy from the energy source and guide the energy into the balloon interior so that plasma is formed in the balloon fluid within the balloon interior; and a second balloon that is positioned to substantially completely encircle the balloon, the second balloon including a second balloon wall that is positioned such that the second balloon wall is positioned substantially directly adjacent to the balloon wall.

In certain embodiments, the balloon is made from a first material and the second balloon is made from a second material that is different than the first material. In some such embodiments, the first material that is used to form the balloon has a higher melting temperature than the second material that is used to form the second balloon. For example, in such embodiments, the first material that is used to form the balloon can have a melting temperature that is at least approximately 10 degrees Kelvin higher than a second melting temperature of the second material that is used to form the second balloon. Further in such embodiments, the first material can be a silicone-based material.

In various embodiments, the first material that is used to form the balloon has a lower melting temperature than the second material that is used to form the second balloon. For example, in such embodiments, the first material that is used to form the balloon can have a melting temperature that is at least approximately 10 degrees Kelvin lower than a second melting temperature of the second material that is used to form the second balloon. Further, in such embodiments, the second material can be a silicone-based material.

The first material can be an open cell foam material. In some embodiments, at least one void formed within the open cell foam material is filled with an inflation material.

In certain embodiments, the catheter system further includes a third balloon that is positioned to substantially completely encircle the balloon, the third balloon being positioned substantially directly adjacent to the second balloon. In some such embodiments, the balloon is made from a first material, the second balloon is made from a second material, and the third balloon is made from a third material; and wherein at least one of the first material, the second material and the third material is different than the other materials. For example, in one such embodiment, the second material is different than each of the first material and the third material. In particular, in such embodiment, the second material can be configured to one of reflect and absorb light and heat. In certain such alternative embodiments, the second material is formed from one or more of a metallic foil, a carbon foil, and a closed-cell membrane filled with a fluid.

In certain applications, the present invention is directed toward a catheter system for treating a treatment site within or adjacent to a vessel wall or heart valve, the catheter system including an energy source that generates energy; a balloon that is positionable substantially adjacent to the treatment site, the balloon having a balloon wall that defines a balloon interior, the balloon being configured to retain a balloon fluid within the balloon interior; an energy guide that is configured to receive energy from the energy source and guide the energy into the balloon interior so that plasma is formed in the balloon fluid within the balloon interior; and a composite material that is added onto a surface of the balloon.

In some embodiments, the composite material is added onto an inner surface of the balloon.

The catheter system can also include a plasma generator that is positioned at a guide distal end of the energy guide, the plasma generator being configured to generate the plasma in the balloon fluid within the balloon interior. In such embodiment, the composite material can be added onto an inner surface of the balloon near the plasma generator. Additionally, the composite material can be configured to one of reflect and absorb light and heat. In certain such embodiments, the composite material is formed from one or more of a metallic foil, a carbon foil, and a closed-cell membrane filled with a fluid.

In some applications, the present invention is directed toward a catheter system for treating a treatment site within or adjacent to a vessel wall or heart valve, the catheter system including an energy source that generates energy; a balloon that is positionable substantially adjacent to the treatment site, the balloon having a balloon wall that defines a balloon interior, the balloon being configured to retain a balloon fluid within the balloon interior; an energy guide that is configured to receive energy from the energy source and guide the energy into the balloon interior so that plasma is formed in the balloon fluid within the balloon interior; and a braided material layer that is wrapped around a surface of the balloon to provide a braided balloon composite.

In certain embodiments, the braided material layer is wrapped around an outer surface of the balloon. Additionally, in some embodiments, the braided material layer is wrapped around the surface of the balloon to provide increased hoop and axial strength.

In some embodiments, the braided material layer is wrapped around the surface of the balloon in a manner so as to shorten the balloon upon inflation of the balloon. In another such embodiment, the braided material layer is configured to inhibit propagation of tears in the balloon.

In some embodiments, the braided material layer is formed from a high strength fiber such as nitinol, stainless steel, carbon, aramid, rayon, polyester, aromatic polyester (such as Vectran), nylon, natural (silk, wool, cotton and linen) fibers, and/or any other suitable materials.

In certain applications, the present invention is directed toward a catheter system for treating a treatment site within or adjacent to a vessel wall or heart valve, the catheter system including an energy source that generates energy; a balloon that is positionable substantially adjacent to the treatment site, the balloon having a balloon wall that defines a balloon interior, the balloon being configured to retain a balloon fluid within the balloon interior; and an energy guide that is configured to receive energy from the energy source and guide the energy into the balloon interior so that plasma is formed in the balloon fluid within the balloon interior; and wherein the balloon is formed as an electro-spun balloon. In such embodiments, the balloon is formed as an electro-spun balloon to increase a melting temperature of the balloon.

In some applications, the present invention is directed toward a catheter system for treating a treatment site within or adjacent to a vessel wall or heart valve, the catheter system including an energy source that generates energy; a balloon that is positionable substantially adjacent to the treatment site, the balloon having a balloon wall that defines a balloon interior, the balloon being configured to retain a balloon fluid within the balloon interior; and an energy guide that is configured to receive energy from the energy source and guide the energy into the balloon interior so that plasma is formed in the balloon fluid within the balloon interior; and wherein the balloon is formed from electrically conductive balloon material.

In certain applications, the present invention is directed toward a catheter system for treating a treatment site within or adjacent to a vessel wall or heart valve, the catheter system including an energy source that generates energy; a balloon that is positionable substantially adjacent to the treatment site, the balloon having a balloon wall that defines a balloon interior, the balloon being configured to retain a balloon fluid within the balloon interior; and an energy guide that is configured to receive energy from the energy source and guide the energy into the balloon interior so that plasma is formed in the balloon fluid within the balloon interior; and wherein the balloon is formed from thermally conductive balloon material.

In some applications, the present invention is directed toward a catheter system for treating a treatment site within or adjacent to a vessel wall or heart valve, the catheter system including an energy source that generates energy; a balloon that is positionable substantially adjacent to the treatment site, the balloon having a balloon wall that defines a balloon interior, the balloon being configured to retain a balloon fluid within the balloon interior; a catheter shaft that extends into the balloon interior, the balloon being coupled to the catheter shaft, the catheter shaft including a shaft recess; an energy guide that is configured to receive energy from the energy source and guide the energy into the balloon interior; and a plasma generator that is positioned at a guide distal end of the energy guide, the plasma generator being configured to generate the plasma in the balloon fluid within the balloon interior; and wherein the energy guide is positioned such that the plasma generator is positioned substantially within the shaft recess.

In certain embodiments, the catheter shaft further includes at least one shaft projection that is positioned along the catheter shaft and about the plasma generator. In one such embodiment, the at least one shaft projection is positioned about the shaft recess.

In some embodiments, the catheter system further includes a protection cage that is fitted over the plasma generator. In such embodiments, the protection cage can be formed from one or more of a polymeric material and a metallic material.

In certain embodiments, the catheter system further includes a pair of separator balloons that are positioned about the catheter shaft at either end of the shaft recess. In some such embodiments, the separator balloons are configured to extend substantially completely from the catheter shaft to the balloon wall of the balloon on either side of the plasma generator when the separator balloons are inflated.

In some embodiments, the catheter system further includes one or more raised features that are molded onto a surface of the balloon. For example, in such embodiments, the one or more raised features can be molded onto an inner surface of the balloon. In certain such embodiments, the one or more raised features includes one or more circumferential raised features that extend about a circumference of the balloon. Additionally, or in the alternative, the one or more raised features includes one or more axial raised features that extend axial along the surface of the balloon.

In certain applications, the present invention is directed toward a catheter system for treating a treatment site within or adjacent to a vessel wall or heart valve, the catheter system including an energy source that generates energy; a catheter shaft that extends into the blood vessel, the catheter shaft including a shaft recess; an energy guide that is configured to receive energy from the energy source and guide the energy into the blood vessel; and a plasma generator that is positioned at a guide distal end of the energy guide, the plasma generator being configured to generate the plasma in a fluid within the blood vessel; and wherein the energy guide is positioned such that the plasma generator is positioned substantially within the shaft recess.

In some such embodiments, the catheter system further includes a pair of separator balloons that are positioned about the catheter shaft at either end of the shaft recess. Additionally, in such embodiments, the separator balloons can be configured to extend substantially completely from the catheter shaft to the vessel wall of the blood vessel on either side of the plasma generator when the separator balloons are inflated.

In some applications, the present invention is directed toward a catheter system for treating a treatment site within or adjacent to a vessel wall or heart valve, the catheter system including an energy source that generates energy; a balloon that is positionable substantially adjacent to the treatment site, the balloon having a balloon wall that defines a balloon interior, the balloon being configured to retain a balloon fluid within the balloon interior; an energy guide that is configured to receive energy from the energy source and guide the energy into the balloon interior so that plasma is formed in the balloon fluid within the balloon interior; and leak plugging material that is distributed within the balloon interior, the leak plugging material being configured to plug leaks in the balloon if any leaks develop in the balloon during use of the catheter system.

In certain such embodiments, the leak plugging material is provided in the form of beads that are between approximately one µm and 100 µm in diameter. Additionally, in some embodiments, the leak plugging material is non-absorbable. Alternatively, in other embodiments, the leak plugging material is bio-absorbable.

In certain applications, the present invention is directed toward a catheter system for treating a treatment site within or adjacent to a vessel wall or heart valve, the catheter system including an energy source that generates energy; a balloon that is positionable substantially adjacent to the treatment site, the balloon having a balloon wall that defines a balloon interior, the balloon being configured to retain a balloon fluid within the balloon interior; and an energy guide that is configured to receive energy from the energy source and guide the energy into the balloon interior so that plasma is formed in the balloon fluid within the balloon interior; and wherein the balloon is optically opaque.

The present invention is also directed toward a method for treating a treatment site within or adjacent to a vessel wall or heart valve, utilizing any of the catheter systems as described above.

The present invention is also directed toward a method for treating a treatment site within or adjacent to a vessel wall or heart valve, the method including the steps of generating energy with an energy source; positioning a balloon substantially adjacent to the treatment site, the balloon having a balloon wall that defines a balloon interior; retaining a balloon fluid within the balloon interior; receiving energy from the energy source with an energy guide; guiding the energy into the balloon interior with the energy guide to form plasma in the balloon fluid within the balloon interior; and operatively coupling a balloon integrity protection system to the balloon, the balloon integrity protection system being configured to inhibit rupture of the balloon due to the plasma formed in the balloon fluid within the balloon interior during use of the catheter system.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 14 is a schematic cross-sectional view of a portion of the catheter system including yet another embodiment of the balloon integrity protection system;

FIG. 15 is a schematic cross-sectional view of a portion of the catheter system including another embodiment of the balloon integrity protection system;

Figure 1:
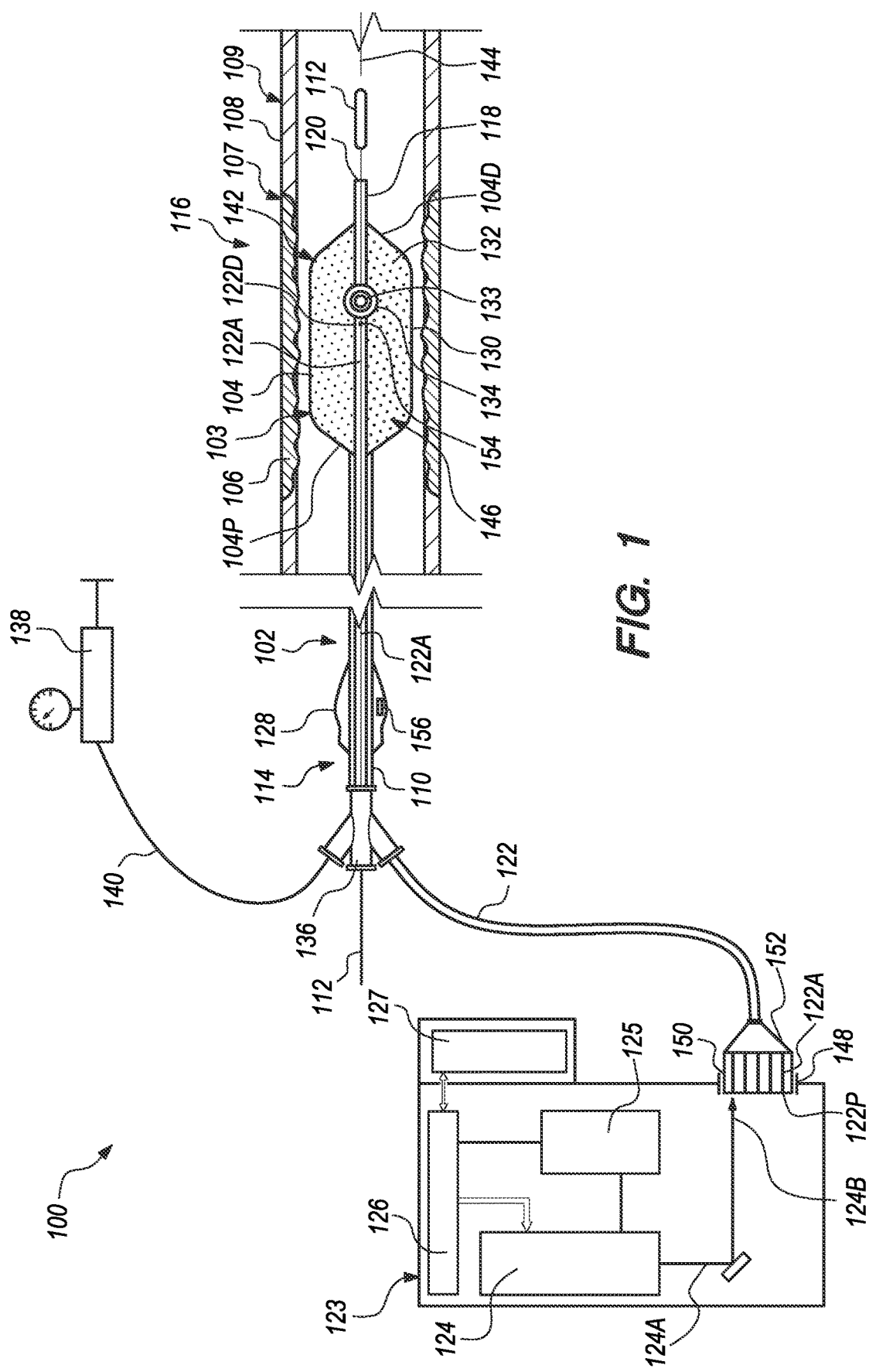
FIG. 1 is a schematic cross-sectional view of an embodiment of a catheter system in accordance with various embodiments herein, the catheter system including a balloon integrity protection system having features of the present invention.

While embodiments of the present invention are susceptible to various modifications and alternative forms, specifics thereof have been shown by way of example and drawings, and are described in detail herein. It is understood, however, that the scope herein is not limited to the particular embodiments described. On the contrary, the intention is to cover modifications, equivalents, and alternatives falling within the spirit and scope herein.

DESCRIPTION

Treatment of vascular lesions (also sometimes referred to herein as "treatment sites") can reduce major adverse events or death in affected subjects. As referred to herein, a major adverse event is one that can occur anywhere within the body due to the presence of a vascular lesion. Major adverse events can include, but are not limited to, major adverse cardiac events, major adverse events in the peripheral or central vasculature, major adverse events in the brain, major adverse events in the musculature, or major adverse events in any of the internal organs.

The catheter systems and related methods disclosed herein are configured to minimize the possibility of balloon rupture and maintain catheter integrity when performing intravascular lithotripsy with a plasma generator. In various embodiments, the catheter systems and related methods of the present invention utilize a high energy source, e.g., in some embodiments, a light source such as a high energy laser source or another suitable high energy source, which provides energy that is guided by an energy guide, e.g., in some embodiments, a light guide, to create a localized plasma in the balloon fluid that is retained within a balloon interior of an inflatable balloon of the catheter. As such, the energy guide can sometimes be referred to as, or can be said to incorporate a "plasma generator" at or near a guide distal end of the energy guide that is positioned within the balloon interior. The creation of the localized plasma, in turn, induces a high energy bubble inside the balloon interior to create pressure waves to impart pressure onto and induce fractures in a vascular lesion, such as a calcified vascular lesion or a fibrous vascular lesion, at a treatment site within or adjacent to a blood vessel wall within a body of a patient. As used herein, the treatment site can include a vascular lesion such as a calcified vascular lesion or a fibrous vascular lesion, typically found in a blood vessel and/or a heart valve.

As used herein, the terms "intravascular lesion" and "vascular lesion" are used interchangeably unless otherwise noted. As such, the intravascular lesions and/or the vascular lesions are sometimes referred to herein simply as "lesions".

Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application-related and business-related constraints, and that these specific goals will vary from one implementation to another and from one developer to another. Moreover, it is appreciated that such a development effort might be complex and time-consuming, but would nevertheless be a routine undertaking of engineering for those of ordinary skill in the art having the benefit of this disclosure.

It is appreciated that the catheter systems disclosed herein can include many different forms. Referring now to FIG. 1, a schematic cross-sectional view is shown of a catheter system 100 in accordance with various embodiments herein. As described herein, the catheter system 100 is suitable for imparting pressure to induce fractures in one or more vascular lesions within or adjacent a vessel wall of a blood vessel. In the embodiment illustrated in FIG. 1, the catheter system 100 can include one or more of a catheter 102, a light guide bundle 122 including one or more light guides 122A, a source manifold 136, a fluid pump 138, a system console 123 including one or more of a light source 124, a power source 125, a system controller 126, and a graphic user interface 127 (a "GUI"), and a handle assembly 128. Additionally, as described in detail herein, the catheter system 100 can further incorporate a balloon integrity protection system 142, which in many embodiments is incorporated into the catheter 102. Alternatively, the catheter system 100 can have more components or fewer components than those specifically illustrated and described in relation to FIG. 1.

The catheter 102 is configured to move to a treatment site 106 within or adjacent to a blood vessel 108 within a body 107 of a patient 109. The treatment site 106 can include one or more vascular lesions such as calcified vascular lesions, for example. Additionally, or in the alternative, the treatment site 106 can include vascular lesions such as fibrous vascular lesions.

The catheter 102 can include a balloon assembly 103 including an inflatable balloon 104 (sometimes referred to herein simply as a "balloon"), a catheter shaft 110 and a guidewire 112. The balloon 104 can be coupled to the catheter shaft 110. The balloon 104 can include a balloon proximal end 104P and a balloon distal end 104D. The catheter shaft 110 can extend from a proximal portion 114 of the catheter system 100 to a distal portion 116 of the catheter system 100. The catheter shaft 110 can include a longitudinal axis 144. The catheter shaft 110 can also include a guidewire lumen 118 which is configured to move over the guidewire 112. As utilized herein, the guidewire lumen 118 is intended to define the structure that provides a conduit through which the guidewire extends. The catheter shaft 110 can further include an inflation lumen (not shown). In some embodiments, the catheter 102 can have a distal end opening 120 and can accommodate and be tracked over the guidewire 112 as the catheter 102 is moved and positioned at or near the treatment site 106.

Importantly, as described in detail in various non-exclusive alternative embodiments herein below, the catheter system 100, the catheter 102 and/or the balloon assembly 103 can further include the balloon integrity protection system 142 that is operatively coupled to the balloon 104, the balloon integrity protection system 142 being configured to inhibit rupture or other damage to the balloon 104 during use of the catheter system 100. More particularly, in various embodiments, such as described in detail herein below, the balloon integrity protection system 142 can be incorporated into the balloon assembly 103 in order to more effectively protect the integrity of the balloon 104.

The catheter shaft 110 of the catheter 102 can be coupled to the one or more light guides 122A of the light guide bundle 122 that are in optical communication with the light source 124. The light guide(s) 122A can be disposed along the catheter shaft 110 and within the balloon 104. In some embodiments, each light guide 122A can be an optical fiber and the light source 124 can be a laser. The light source 124 can be in optical communication with the light guides 122A at the proximal portion 114 of the catheter system 100.

In some embodiments, the catheter shaft 110 can be coupled to multiple light guides 122A such as a first light guide, a second light guide, a third light guide, etc., which can be disposed at any suitable positions about the guidewire lumen 118 and/or the catheter shaft 110. For example, in certain non-exclusive embodiments, two light guides 122A can be spaced apart by approximately 180 degrees about the circumference of the guidewire lumen 118 and/or the catheter shaft 110; three light guides 122A can be spaced apart by approximately 120 degrees about the circumference of the guidewire lumen 118 and/or the catheter shaft 110; or four light guides 122A can be spaced apart by approximately 90 degrees about the circumference of the guidewire lumen 118 and/or the catheter shaft 110. Still alternatively, multiple light guides 122A need not be uniformly spaced apart from one another about the circumference of the guidewire lumen 118 and/or the catheter shaft 110. More particularly, it is further appreciated that the light guides 122A described herein can be disposed uniformly or non-uniformly about the guidewire lumen 118 and/or the catheter shaft 110 to achieve the desired effect in the desired locations.

The balloon 104 can include a balloon wall 130 that defines a balloon interior 146, and can be inflated with a balloon fluid 132 to expand from a deflated configuration suitable for advancing the catheter 102 through a patient's vasculature, to an inflated configuration suitable for anchoring the catheter 102 in position relative to the treatment site 106. Stated in another manner, when the balloon 104 is in the inflated configuration, the balloon wall 130 of the balloon 104 is configured to be positioned substantially adjacent to the treatment site 106, i.e. to the vascular lesion(s). It is appreciated that although FIG. 1 illustrates the balloon wall 130 of the balloon 104 being shown spaced apart from the treatment site 106 of the blood vessel 108, this is done merely for ease of illustration, and the balloon wall 130 of the balloon 104 will typically be substantially directly adjacent to the treatment site 106 when the balloon is in the inflated configuration.

In some embodiments, the light source 124 of the catheter system 100 can be configured to provide sub-millisecond pulses of light from the light source 124, along the light guides 122A, to a location within the balloon interior 146 of the balloon 104, thereby inducing plasma formation in the balloon fluid 132 within the balloon interior 146 of the balloon 104, i.e. via a plasma generator 133 located at a guide distal end 122D of the light guide 122A. The plasma formation causes rapid bubble formation, and imparts pressure waves upon the treatment site 106. Exemplary plasma-induced bubbles are shown as bubbles 134 in FIG. 1.

It is appreciated that although the catheter systems 100 illustrated herein are generally described as including a light source 124 and one or more light guides 122A, the catheter system 100 can alternatively include any suitable energy source and energy guides for purposes of generating the desired plasma in the balloon fluid 132 within the balloon interior 146. For example, in one non-exclusive alternative embodiment, the energy source 124 can be configured to provide high voltage pulses, and each energy guide 122A can include an electrode pair including spaced apart electrodes that extend into the balloon interior 146. In such embodiment, each pulse of high voltage is applied to the electrodes and forms an electrical arc across the electrodes, which, in turn, generates the plasma and forms the pressure waves within the balloon fluid 132 that are utilized to provide the fracture force onto the vascular lesions at the treatment site 106. Still alternatively, the energy source 124 and/or the energy guides 122A can have another suitable design and/or configuration.

The balloons 104 suitable for use in the catheter systems 100 described in detail herein include those that can be passed through the vasculature of a patient when in the deflated configuration. In some embodiments, the balloons 104 herein are made from silicone. In other embodiments, the balloons 104 herein are made from polydimethylsiloxane (PDMS), polyurethane, polymers such as PEBAX™ material available from Arkema, which has a location at King of Prussia, Pennsylvania, USA, nylon, and the like. In some embodiments, the balloons 104 can include those having diameters ranging from one millimeter (mm) to 25 mm in diameter. In some embodiments, the balloons 104 can include those having diameters ranging from at least 1.5 mm to 14 mm in diameter. In some embodiments, the balloons 104 can include those having diameters ranging from at least one mm to five mm in diameter.

Additionally, in some embodiments, the balloons 104 herein can include those having a length ranging from at least three mm to 300 mm. More particularly, in some embodiments, the balloons 104 herein can include those having a length ranging from at least eight mm to 200 mm. It is appreciated that balloons 104 of greater length can be positioned adjacent to larger treatment sites 106, and, thus, may be usable for imparting pressure onto and inducing fractures in larger vascular lesions or multiple vascular lesions at precise locations within the treatment site 106. It is further appreciated that such longer balloons 104 can also be positioned adjacent to multiple treatment sites 106 at any given time.

Further, the balloons 104 herein can be inflated to inflation pressures of between approximately one atmosphere (atm) and 70 atm. In some embodiments, the balloons 104 herein can be inflated to inflation pressures of from at least 20 atm to 70 atm. In other embodiments, the balloons 104 herein can be inflated to inflation pressures of from at least six atm to 20 atm. In still other embodiments, the balloons 104 herein can be inflated to inflation pressures of from at least three atm to 20 atm. In yet other embodiments, the balloons 104 herein can be inflated to inflation pressures of from at least two atm to ten atm.

Still further, the balloons 104 herein can include those having various shapes, including, but not to be limited to, a conical shape, a square shape, a rectangular shape, a spherical shape, a conical/square shape, a conical/spherical shape, an extended spherical shape, an oval shape, a tapered shape, a bone shape, a stepped diameter shape, an offset shape, or a conical offset shape. In some embodiments, the balloons 104 herein can include a drug eluting coating or a drug eluting stent structure. The drug elution coating or drug eluting stent can include one or more therapeutic agents including anti-inflammatory agents, anti-neoplastic agents, anti-angiogenic agents, and the like.

The balloon fluid 132 can be a liquid or a gas. Exemplary balloon fluids 132 suitable for use herein can include, but are not limited to one or more of water, saline, contrast medium, fluorocarbons, perfluorocarbons, gases, such as carbon dioxide, and the like. In some embodiments, the balloon fluids 132 described can be used as base inflation fluids. In some embodiments, the balloon fluids 132 include a mixture of saline to contrast medium in a volume ratio of 50:50. In other embodiments, the balloon fluids 132 include a mixture of saline to contrast medium in a volume ratio of 25:75. In still other embodiments, the balloon fluids 132 include a mixture of saline to contrast medium in a volume ratio of 75:25. Additionally, the balloon fluids 132 suitable for use herein can be tailored on the basis of composition, viscosity, and the like in order to manipulate the rate of travel of the pressure waves therein. In certain embodiments, the balloon fluids 132 suitable for use herein are biocompatible. A volume of balloon fluid 132 can be tailored by the chosen light source 124 and the type of balloon fluid 132 used.

In some embodiments, the contrast agents used in the contrast media herein can include, but are not to be limited to, iodine-based contrast agents, such as ionic or non-ionic iodine-based contrast agents. Some non-limiting examples of ionic iodine-based contrast agents include diatrizoate, metrizoate, iothalamate, and ioxaglate. Some non-limiting examples of non-ionic iodine-based contrast agents include iopamidol, iohexol, ioxilan, iopromide, iodixanol, and ioversol. In other embodiments, non-iodine based contrast agents can be used. Suitable non-iodine containing contrast agents can include gadolinium (III)-based contrast agents. Suitable fluorocarbon and perfluorocarbon agents can include, but are not to be limited to, agents such as the perfluorocarbon dodecafluoropentane (DDFP, C5F12).

Additionally, the balloon fluids 132 herein can include those that include absorptive agents that can selectively absorb light in the ultraviolet region (e.g., at least ten nanometers (nm) to 400 nm), the visible region (e.g., at least 400 nm to 780 nm), or the near-infrared region (e.g., at least 780 nm to 2.5 µm) of the electromagnetic spectrum. Suitable absorptive agents can include those with absorption maxima along the spectrum from at least ten nm to 2.5 µm. Alternatively, the balloon fluids 132 can include those that include absorptive agents that can selectively absorb light in the mid-infrared region (e.g., at least 2.5 µm to 15 µm), or the far-infrared region (e.g., at least 15 µm to one mm) of the electromagnetic spectrum. In various embodiments, the absorptive agent can be those that have an absorption maximum matched with the emission maximum of the laser used in the catheter system 100. By way of non-limiting examples, various lasers described herein can include neodymium:yttrium-aluminum-garnet (Nd:YAG–emission maximum=1064 nm) lasers, holmium:YAG (Ho:YAG–emission maximum=2.1 µm) lasers, or erbium:YAG (Er:YAG–emission maximum=2.94 µm) lasers. In some embodiments, the absorptive agents used herein can be water soluble. In other embodiments, the absorptive agents used herein are not water soluble. In some embodiments, the absorptive agents used in the balloon fluids 132 herein can be tailored to match the peak emission of the light source 124. Various light sources 124 having emission wavelengths of at least ten nanometers to one millimeter are discussed elsewhere herein.

It is appreciated that the catheter system 100 and/or the light guide bundle 122 disclosed herein can include any number of light guides 122A in optical communication with the light source 124 at the proximal portion 114, and with the balloon fluid 132 within the balloon interior 146 of the balloon 104 at the distal portion 116. For example, in some embodiments, the catheter system 100 and/or the light guide bundle 122 can include from one light guide 122A to five light guides 122A. In other embodiments, the catheter system 100 and/or the light guide bundle 122 can include from five light guides 122A to fifteen light guides 122A. In yet other embodiments, the catheter system 100 and/or the light guide bundle 122 can include from ten light guides 122A to thirty light guides 122A. Alternatively, in still other embodiments, the catheter system 100 and/or the light guide bundle 122 can include greater than thirty light guides 122A.

The light guides 122A herein can include an optical fiber or flexible light pipe. The light guides 122A herein can be thin and flexible and can allow light signals to be sent with very little loss of strength. The light guides 122A herein can include a core surrounded by a cladding about its circumference. In some embodiments, the core can be a cylindrical core or a partially cylindrical core. The core and cladding of the light guides 122A can be formed from one or more materials, including but not limited to one or more types of glass, silica, or one or more polymers. The light guides 122A may also include a protective coating, such as a polymer. It is appreciated that the index of refraction of the core will be greater than the index of refraction of the cladding.

Each light guide 122A can guide light along its length from a proximal portion, i.e. a guide proximal end 122P, to a distal portion, i.e. the guide distal end 122D, having at least one optical window (not shown) that is positioned within the balloon interior 146. The light guides 122A can create a light path as a portion of an optical network including the light source 124. The light path within the optical network allows light to travel from one part of the network to another. Both the optical fiber and the flexible light pipe can provide a light path within the optical networks herein.

Further, the light guides 122A herein can assume many configurations about and/or relative to the catheter shaft 110 of the catheters 102 described herein. In some embodiments, the light guides 122A can run parallel to the longitudinal axis 144 of the catheter shaft 110. In some embodiments, the light guides 122A can be physically coupled to the catheter shaft 110. In other embodiments, the light guides 122A can be disposed along a length of an outer diameter of the catheter shaft 110. In yet other embodiments, the light guides 122A herein can be disposed within one or more light guide lumens within the catheter shaft 110.

Additionally, it is further appreciated that the light guides 122A can be disposed at any suitable positions about the circumference of the guidewire lumen 118 and/or the catheter shaft 110, and the guide distal end 122D of each of the light guides 122A can be disposed at any suitable longitudinal position relative to the length of the balloon 104 and/or relative to the length of the guidewire lumen 118.

Further, the light guides 122A herein can include one or more photoacoustic transducers 154, where each photoacoustic transducer 154 can be in optical communication with the light guide 122A within which it is disposed. In some embodiments, the photoacoustic transducers 154 can be in optical communication with the guide distal end 122D of the light guide 122A. Additionally, in such embodiments, the photoacoustic transducers 154 can have a shape that corresponds with and/or conforms to the guide distal end 122D of the light guide 122A.

The photoacoustic transducer 154 is configured to convert light energy into an acoustic wave at or near the guide distal end 122D of the light guide 122A. It is appreciated that the direction of the acoustic wave can be tailored by changing an angle of the guide distal end 122D of the light guide 122A.

It is further appreciated that the photoacoustic transducers 154 disposed at the guide distal end 122D of the light guide 122A herein can assume the same shape as the guide distal end 122D of the light guide 122A. For example, in certain non-exclusive embodiments, the photoacoustic transducer 154 and/or the guide distal end 122D can have a conical shape, a convex shape, a concave shape, a bulbous shape, a square shape, a stepped shape, a half-circle shape, an ovoid shape, and the like. It is also appreciated that the light guide 122A can further include additional photoacoustic transducers 154 disposed along one or more side surfaces of the length of the light guide 122A.

The light guides 122A described herein can further include one or more diverting features or "diverters" (not shown in FIG. 1) within the light guide 122A that are configured to direct light to exit the light guide 122A toward a side surface e.g., at or near the guide distal end 122D of the light guide 122A, and toward the balloon wall 130. A diverting feature can include any feature of the system herein that diverts light from the light guide 122A away from its axial path toward a side surface of the light guide 122A. Additionally, the light guides 122A can each include one or more light windows disposed along the longitudinal or axial surfaces of each light guide 122A and in optical communication with a diverting feature. Stated in another manner, the diverting features herein can be configured to direct light in the light guide 122A toward a side surface, e.g., at or near the guide distal end 122D, where the side surface is in optical communication with a light window. The light windows can include a portion of the light guide 122A that allows light to exit the light guide 122A from within the light guide 122A, such as a portion of the light guide 122A lacking a cladding material on or about the light guide 122A.

Examples of the diverting features suitable for use herein include a reflecting element, a refracting element, and a fiber diffuser. Additionally, the diverting features suitable for focusing light away from the tip of the light guides 122A herein can include, but are not to be limited to, those having a convex surface, a gradient-index (GRIN) lens, and a mirror focus lens. Upon contact with the diverting feature, the light is diverted within the light guide 122A to the plasma generator 133 and/or the photoacoustic transducer(s) 154 that are in optical communication with a side surface of the light guide 122A. As noted, the plasma generator 133 and/or the photoacoustic transducer(s) 154 then convert light energy into an acoustic pressure wave and bubble that extend away from the side surface of the light guide 122A.

The source manifold 136 can be positioned at or near the proximal portion 114 of the catheter system 100. The source manifold 136 can include one or more proximal end openings that can receive the plurality of light guides 122A of the light guide bundle 122, the guidewire 112, and/or an inflation conduit 140 that is coupled in fluid communication with the fluid pump 138. The catheter system 100 can also include the fluid pump 138 that is configured to inflate the balloon 104 with the balloon fluid 132, i.e. via the inflation conduit 140, as needed.

As noted above, in the embodiment illustrated in FIG. 1, the system console 123 includes one or more of the light source 124, the power source 125, the system controller 126, and the GUI 127. Alternatively, the system console 123 can include more components or fewer components than those specifically illustrated in FIG. 1. For example, in certain non-exclusive alternative embodiments, the system console 123 can be designed without the GUI 127. Still alternatively, one or more of the light source 124, the power source 125, the system controller 126, and the GUI 127 can be provided within the catheter system 100 without the specific need for the system console 123.

Additionally, as shown, the system console 123, and the components included therewith, is operatively coupled to the catheter 102, the light guide bundle 122, and the remainder of the catheter system 100. For example, in some embodiments, as illustrated in FIG. 1, the system console 123 can include a console connection aperture 148 (also sometimes referred to generally as a "socket") by which the light guide bundle 122 is mechanically coupled to the system console 123. In such embodiments, the light guide bundle 122 can include a guide coupling housing 150 (also sometimes referred to generally as a "ferrule") that houses a portion, e.g., the guide proximal end 122P, of each of the light guides 122A. The guide coupling housing 150 is configured to fit and be selectively retained within the console connection aperture 148 to provide the desired mechanical coupling between the light guide bundle 122 and the system console 123.

Further, the light guide bundle 122 can also include a guide bundler 152 (or "shell") that brings each of the individual light guides 122A closer together so that the light guides 122A and/or the light guide bundle 122 can be in a more compact form as it extends with the catheter 102 into the blood vessel 108 during use of the catheter system 100.

As provided herein, the light source 124 can be selectively and/or alternatively coupled in optical communication with each of the light guides 122A, i.e. to the guide proximal end 122P of each of the light guides 122A, in the light guide bundle 122. In particular, the light source 124 is configured to generate light energy in the form of a source beam 124A, e.g., a pulsed source beam, that can be selectively and/or alternatively directed to and received by each of the light guides 122A in the light guide bundle 122 as an individual guide beam 124B. Alternatively, the catheter system 100 can include more than one light source 124. For example, in one non-exclusive alternative embodiment, the catheter system 100 can include a separate light source 124 for each of the light guides 122A in the light guide bundle 122.

The light source 124 can have any suitable design. In certain embodiments, as noted above, the light source 124 can be configured to provide sub-millisecond pulses of light from the light source 124 that are focused onto a small spot in order to couple it into the guide proximal end 122P of the light guide 122A. Such pulses of light energy are then directed along the light guides 122A to a location within the balloon 104, thereby inducing plasma formation in the balloon fluid 132 within the balloon interior 146 of the balloon 104. In particular, the light energy emitted at the guide distal end 122D of the light guide 122A energizes the plasma generator 133 to form the plasma within the balloon fluid 132 within the balloon interior 146. The plasma formation causes rapid bubble formation, and imparts pressure waves upon the treatment site 106. In such embodiments, the sub-millisecond pulses of light from the light source 124 can be delivered to the treatment site 106 at a frequency of between approximately one hertz (Hz) and 5000 Hz. In some embodiments, the sub-millisecond pulses of light from the light source 124 can be delivered to the treatment site 106 at a frequency of between approximately 30 Hz and 1000 Hz. In other embodiments, the sub-millisecond pulses of light from the light source 124 can be delivered to the treatment site 106 at a frequency of between approximately ten Hz and 100 Hz. In yet other embodiments, the sub-millisecond pulses of light from the light source 124 can be delivered to the treatment site 106 at a frequency of between approximately one Hz and 30 Hz. Alternatively, the sub-millisecond pulses of light can be delivered to the treatment site 106 at a frequency that can be greater than 5000 Hz.

It is appreciated that although the light source 124 is typically utilized to provide pulses of light energy, the light source 124 can still be described as providing a single source beam 124A, i.e. a single pulsed source beam.

The light sources 124 suitable for use herein can include various types of light sources including lasers and lamps. Alternatively, as noted above, the light sources 124, as referred to herein, can include any suitable type of energy source.

Suitable lasers can include short pulse lasers on the sub-millisecond timescale. In some embodiments, the light source 124 can include lasers on the nanosecond (ns) timescale. The lasers can also include short pulse lasers on the picosecond (ps), femtosecond (fs), and microsecond (us) timescales. It is appreciated that there are many combinations of laser wavelengths, pulse widths and energy levels that can be employed to achieve plasma in the balloon fluid 132 of the catheters 102 described herein. In various embodiments, the pulse widths can include those falling within a range including from at least ten ns to 2000 ns. In some embodiments, the pulse widths can include those falling within a range including from at least 20 ns to 100 ns. In other embodiments, the pulse widths can include those falling within a range including from at least one ns to 500 ns.

Additionally, exemplary nanosecond lasers can include those within the UV to IR spectrum, spanning wavelengths of about ten nanometers (nm) to one millimeter (mm). In some embodiments, the light sources 124 suitable for use in the catheter systems 100 herein can include those capable of producing light at wavelengths of from at least 750 nm to 2000 nm. In other embodiments, the light sources 124 can include those capable of producing light at wavelengths of from at least 700 nm to 3000 nm. In still other embodiments, the light sources 124 can include those capable of producing light at wavelengths of from at least 100 nm to ten micrometers (μm). Nanosecond lasers can include those having repetition rates of up to 200 kHz. In some embodiments, the laser can include a Q-switched thulium:yttrium-aluminum-garnet (Tm:YAG) laser. In other embodiments, the laser can include a neodymium:yttrium-aluminum-garnet (Nd:YAG) laser, holmium:yttrium-aluminum-garnet (Ho:YAG) laser, erbium:yttrium-aluminum-garnet (Er:YAG) laser, excimer laser, helium-neon laser, carbon dioxide laser, as well as doped, pulsed, fiber lasers.

The catheter systems 100 disclosed herein can generate pressure waves having maximum pressures in the range of at least one megapascal (MPa) to 100 MPa. The maximum pressure generated by a particular catheter system 100 will depend on the light source 124, the absorbing material, the bubble expansion, the propagation medium, the balloon material, and other factors. In some embodiments, the catheter systems 100 herein can generate pressure waves having maximum pressures in the range of at least two MPa to 50 MPa. In other embodiments, the catheter systems 100 herein can generate pressure waves having maximum pressures in the range of at least two MPa to 30 MPa. In yet other embodiments, the catheter systems 100 herein can generate pressure waves having maximum pressures in the range of at least 15 MPa to 25 MPa.

The pressure waves described herein can be imparted upon the treatment site 106 from a distance within a range from at least 0.1 millimeters (mm) to 25 mm extending radially from the light guides 122A when the catheter 102 is placed at the treatment site 106. In some embodiments, the pressure waves can be imparted upon the treatment site 106 from a distance within a range from at least ten mm to 20 mm extending radially from the light guides 122A when the catheter 102 is placed at the treatment site 106. In other embodiments, the pressure waves can be imparted upon the treatment site 106 from a distance within a range from at least one mm to ten mm extending radially from the light guides 122A when the catheter 102 is placed at the treatment site 106. In yet other embodiments, the pressure waves can be imparted upon the treatment site 106 from a distance within a range from at least 1.5 mm to four mm extending radially from the light guides 122A when the catheter 102 is placed at the treatment site 106. In some embodiments, the pressure waves can be imparted upon the treatment site 106 from a range of at least two MPa to 30 MPa at a distance from 0.1 mm to ten mm. In some embodiments, the pressure waves can be imparted upon the treatment site 106 from a range of at least two MPa to 25 MPa at a distance from 0.1 mm to ten mm.

The power source 125 is electrically coupled to and is configured to provide necessary power to each of the light source 124, the system controller 126, the GUI 127, and the handle assembly 128. The power source 125 can have any suitable design for such purposes.

As noted, the system controller 126 is electrically coupled to and receives power from the power source 125. Additionally, the system controller 126 is coupled to and is configured to control operation of each of the light source 124 and the GUI 127. The system controller 126 can include one or more processors or circuits for purposes of controlling the operation of at least the light source 124 and the GUI 127. For example, the system controller 126 can control the light source 124 for generating pulses of light energy as desired, e.g., at any desired firing rate.

Additionally, the system controller 126 can further be configured to control operation of other components of the catheter system 100, e.g., the positioning of the catheter 102 adjacent to the treatment site 106, the inflation of the balloon 104 with the balloon fluid 132, etc. Further, or in the alternative, the catheter system 100 can include one or more additional controllers that can be positioned in any suitable manner for purposes of controlling the various operations of the catheter system 100. For example, in certain embodiments, an additional controller and/or a portion of the system controller 126 can be positioned and/or incorporated within the handle assembly 128.

The GUI 127 is accessible by the user or operator of the catheter system 100. Additionally, the GUI 127 is electrically connected to the system controller 126. With such design, the GUI 127 can be used by the user or operator to ensure that the catheter system 100 is employed as desired to impart pressure onto and induce fractures into the vascular lesions at the treatment site 106. Additionally, the GUI 127 can provide the user or operator with information that can be used before, during and after use of the catheter system 100. In one embodiment, the GUI 127 can provide static visual data and/or information to the user or operator.

In addition, or in the alternative, the GUI 127 can provide dynamic visual data and/or information to the user or operator, such as video data or any other data that changes over time, e.g., during use of the catheter system 100. Further, in various embodiments, the GUI 127 can include one or more colors, different sizes, varying brightness, etc., that may act as alerts to the user or operator. Additionally, or in the alternative, the GUI 127 can provide audio data or information to the user or operator. It is appreciated that the specifics of the GUI 127 can vary depending upon the design requirements of the catheter system 100, or the specific needs, specifications and/or desires of the user or operator.

As shown in FIG. 1, the handle assembly 128 can be positioned at or near the proximal portion 114 of the catheter system 100, and/or near the source manifold 136. Additionally, in this embodiment, the handle assembly 128 is coupled to the balloon 104 and is positioned spaced apart from the balloon 104. Alternatively, the handle assembly 128 can be positioned at another suitable location.

The handle assembly 128 is handled and used by the user or operator to operate, position and control the catheter 102. The design and specific features of the handle assembly 128 can vary to suit the design requirements of the catheter system 100. In the embodiment illustrated in FIG. 1, the handle assembly 128 is separate from, but in electrical and/or fluid communication with one or more of the system controller 126, the light source 124, the fluid pump 138, and the GUI 127. In some embodiments, the handle assembly 128 can integrate and/or include at least a portion of the system controller 126 within an interior of the handle assembly 128. For example, as shown, in certain such embodiments, the handle assembly 128 can include circuitry 156 that can form at least a portion of the system controller 126.

In one embodiment, the circuitry 156 can include a printed circuit board having one or more integrated circuits, or any other suitable circuitry. In an alternative embodiment, the circuitry 156 can be omitted, or can be included within the system controller 126, which in various embodiments can be positioned outside of the handle assembly 128, e.g., within the system console 123. It is understood that the handle assembly 128 can include fewer or additional components than those specifically illustrated and described herein.

As noted above, in various embodiments, the balloon integrity protection system 142 can be included with and/or incorporated into the catheter system 100, the catheter 102 and/or the balloon assembly 103 in order to inhibit rupture or other damage to the balloon 104 during use of the catheter system 100 in order to more effectively protect the integrity of the balloon 104. Various embodiments of the balloon integrity protection system 142 are described in greater detail herein below in relation to FIGS. 2-20.

Figure 2:
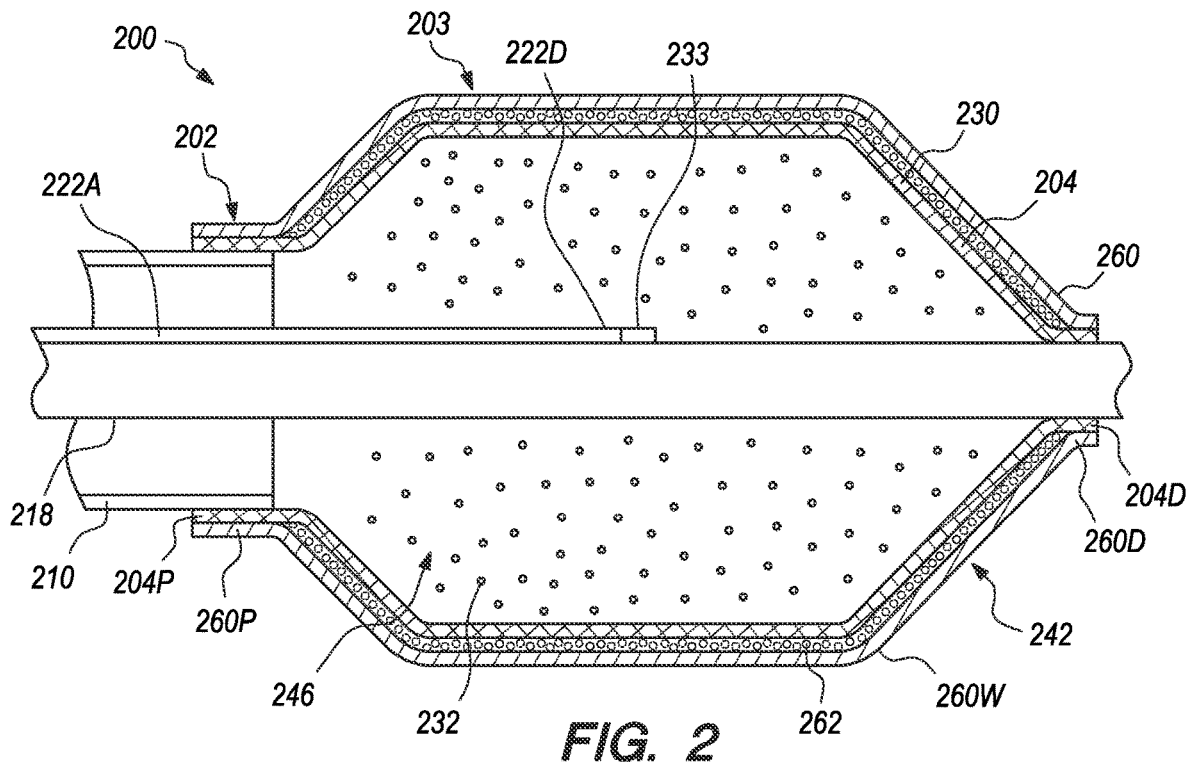
FIG. 2 is a schematic cross-sectional view of a portion of the catheter system including an embodiment of the balloon integrity protection system.

FIG. 2 is a schematic cross-sectional view of a portion of the catheter system 200 including an embodiment of the balloon integrity protection system 242. As described in detail herein, the design of the catheter system 200 can be varied. In various embodiments, as illustrated in FIG. 2, the catheter system 200 can include a catheter 202 including a catheter shaft 210, a balloon assembly 203 including a balloon 204 having a balloon wall 230 that defines a balloon interior 246, a balloon proximal end 204P, and a balloon distal end 204D, a balloon fluid 232 that is retained substantially within the balloon interior 246, and a guidewire lumen 218 that extends into and runs through the balloon interior 246; and an energy guide 222A including a plasma generator 233 that is included and/or incorporated at a guide distal end 222D of the energy guide 222A. Additionally, as described in detail herein, the catheter system 200, the catheter 202 and/or the balloon assembly 203 can further include the balloon integrity protection system 242 that is operatively coupled to the balloon 204 and that is configured to inhibit rupture or other damage to the balloon 204 or otherwise protect the integrity of the balloon 204 during use of the catheter system 200. Alternatively, in other embodiments, the catheter system 200 can include more components or fewer components than what is specifically illustrated and described herein. For example, certain components that were illustrated in FIG. 1, e.g., the guidewire 112, the light source 124, the power source 125, the system controller 126, the GUI 127, the handle assembly 128, the source manifold 136 and the fluid pump 138, are not specifically illustrated in FIG. 2 for purposes of clarity, but would likely be included in any embodiment of the catheter system 200.

The catheter 202, including the catheter shaft 210, the balloon 204, and the guidewire lumen 218, is generally similar in design and operation to what has been described in detail herein above. Thus, such components will not be described in detail again in relation to the embodiment shown in FIG. 2.

As above, the balloon 204 is selectively movable between a deflated configuration suitable for advancing the catheter 202 through a patient's vasculature, and an inflated configuration suitable for anchoring the catheter 202 in position relative to the treatment site 106 (illustrated in FIG. 1). In some embodiments, the balloon proximal end 204P can be coupled to the catheter shaft 210, and the balloon distal end 204D can be coupled to the guidewire lumen 218. In other embodiments, the catheter shaft 210 can extend fully through the balloon 204, and the balloon distal end 204D can also be coupled to the catheter shaft 210. In still other embodiments, the balloon distal end 204D can be coupled to another structure of the catheter 202. Additionally, the balloon 204 can be inflated with the balloon fluid 232, e.g., from the fluid pump 138 (illustrated in FIG. 1), that is directed into the balloon interior 246 of the balloon 204 via the inflation conduit 140 (illustrated in FIG. 1).

As provided herein, the balloon integrity protection system 242 can have any suitable design for purposes of inhibiting rupture or other damage to the balloon 204 or otherwise protecting the integrity of the balloon 204 during use of the catheter system 200. For example, as shown in the embodiment illustrated in FIG. 2, the balloon integrity protection system 242 can include a second balloon 260, and a cooling fluid 262.

As illustrated in FIG. 2, the second balloon 260 includes a second balloon proximal end 260P that is coupled to the balloon proximal end 204P of the balloon 204, and a second balloon distal end 260D that is coupled to the balloon distal end 204D of the balloon 204. Additionally, as illustrated, the balloon 204 is smaller than the second balloon 260 such that the second balloon 260 substantially completely, if not entirely, encircles the balloon 204. Stated in another manner, in this embodiment, the balloon 204 is positioned substantially, if not completely, within the second balloon 260. Further, for a majority of the second balloon 260, the second balloon 260 includes a second balloon wall 260W that is spaced apart and/or separated from the balloon wall 230 of the balloon 204. The separation between the second wall 260W of the second balloon 260 and the balloon wall 230 of the balloon 204 is intended to provide insulation so that any increased temperature at the balloon wall 230 is not directly transferred to the second balloon wall 260W of the second balloon 260.

Additionally, as shown, the cooling fluid 262 is positioned substantially between the balloon wall 230 of the balloon 204 and the second balloon wall 260W of the second balloon 260. In this embodiment, the cooling fluid 262 is circulated between the balloon wall 230 and the second balloon wall 260W to maintain a balloon temperature, e.g., at the second balloon wall 260W, which is below a melting temperature of the second balloon 260. More particularly, with such design, the second balloon 260 is better protected from any increases in temperature in the event that the balloon 204 may rupture or otherwise become damaged during use of the catheter system 200.

The cooling fluid 262 can be formed from any suitable fluid materials. In certain embodiments, the cooling fluid 262 can be formed from the same or similar materials that are used for the balloon fluid 232. For example, in one non-exclusive embodiment, the cooling fluid 262 is formed from a mixture of saline and contrast medium. Alternatively, in other non-exclusive embodiments, the cooling fluid 262 can be formed from water, saline, contrast medium, fluorocarbons, perfluorocarbons, and/or gases, such as carbon dioxide, and the like. Still alternatively, the cooling fluid 262 can be formed from other suitable materials.

Figure 3:
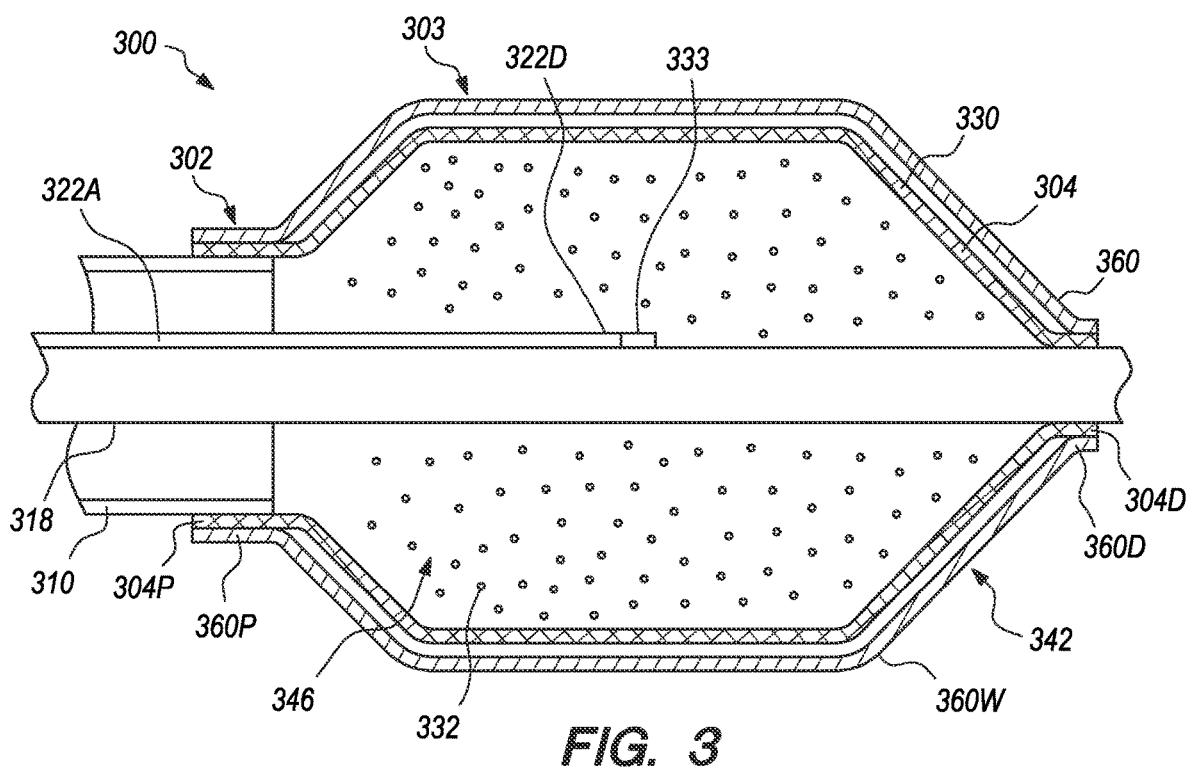
FIG. 3 is a schematic cross-sectional view of a portion of the catheter system including another embodiment of the balloon integrity protection system.

FIG. 3 is a schematic cross-sectional view of a portion of the catheter system 300 including another embodiment of the balloon integrity protection system 342. As with the previous embodiments, as illustrated in FIG. 3, the catheter system 300 can include a catheter 302 including a catheter shaft 310, a balloon assembly 303 including a balloon 304 having a balloon wall 330 that defines a balloon interior 346, a balloon proximal end 304P, and a balloon distal end 304D, a balloon fluid 332 that is retained substantially within the balloon interior 346, and a guidewire lumen 318 that extends into and runs through the balloon interior 346; and an energy guide 322A including a plasma generator 333 that is included and/or incorporated at a guide distal end 322D of the energy guide 322A. Additionally, as with the previous embodiments, the catheter system 300, the catheter 302 and/or the balloon assembly 303 can further include the balloon integrity protection system 342 that is operatively coupled to the balloon 304 and that is configured to inhibit rupture or other damage to the balloon 304 or otherwise protect the integrity of the balloon 304 during use of the catheter system 300. Alternatively, in other embodiments, the catheter system 300 can include more components or fewer components than what is specifically illustrated and described herein. For example, certain components that were illustrated in FIG. 1, e.g., the guidewire 112, the light source 124, the power source 125, the system controller 126, the GUI 127, the handle assembly 128, the source manifold 136 and the fluid pump 138, are not specifically illustrated in FIG. 3 for purposes of clarity, but would likely be included in any embodiment of the catheter system 300.

The catheter 302, including the catheter shaft 310, the balloon 304, and the guidewire lumen 318, is generally similar in design and operation to what has been described in detail herein above. Thus, such components will not be described in detail again in relation to the embodiment shown in FIG. 3.

As above, the balloon 304 is selectively movable between a deflated configuration suitable for advancing the catheter 302 through a patient's vasculature, and an inflated configuration suitable for anchoring the catheter 302 in position relative to the treatment site 106 (illustrated in FIG. 1). In some embodiments, the balloon proximal end 304P can be coupled to the catheter shaft 310, and the balloon distal end 304D can be coupled to the guidewire lumen 318. In other embodiments, the catheter shaft 310 can extend fully through the balloon 304, and the balloon distal end 304D can also be coupled to the catheter shaft 310. In still other embodiments, the balloon distal end 304D can be coupled to another structure of the catheter 302. Additionally, the balloon 304 can be inflated with the balloon fluid 332, e.g., from the fluid pump 138 (illustrated in FIG. 1), that is directed into the balloon interior 346 of the balloon 304 via the inflation conduit 140 (illustrated in FIG. 1).

Further, in this embodiment, the balloon integrity protection system 342 is substantially similar to the embodiment illustrated and described in relation to FIG. 2. In particular, as shown in FIG. 3, the balloon integrity protection system 342 includes a second balloon 360. As shown, the second balloon 360 includes a second balloon proximal end 360P that is coupled to the balloon proximal end 304P of the balloon 304, and a second balloon distal end 360D that is coupled to the balloon distal end 304D of the balloon 304. Additionally, as illustrated, the balloon 304 is smaller than the second balloon 360 such that the second balloon 360 substantially completely, if not entirely, encircles the balloon 304. Stated in another manner, in this embodiment, the balloon 304 is positioned substantially, if not completely, within the second balloon 360. Further, for a majority of the second balloon 360, the second balloon 360 includes a second balloon wall 360W that is spaced apart and/or separated from the balloon wall 330 of the balloon 304. The separation between the second wall 360W of the second balloon 360 and the balloon wall 330 of the balloon 304 is intended to provide insulation so that any increased temperature at the balloon wall 330 is not directly transferred to the second balloon wall 360W of the second balloon 360. Moreover, with the separation between the second balloon wall 360W and the balloon wall 230, the second balloon 360 is better able to maintain pressure in the event that the balloon 204 may rupture or otherwise become damaged during use of the catheter system 300.

Figure 4:
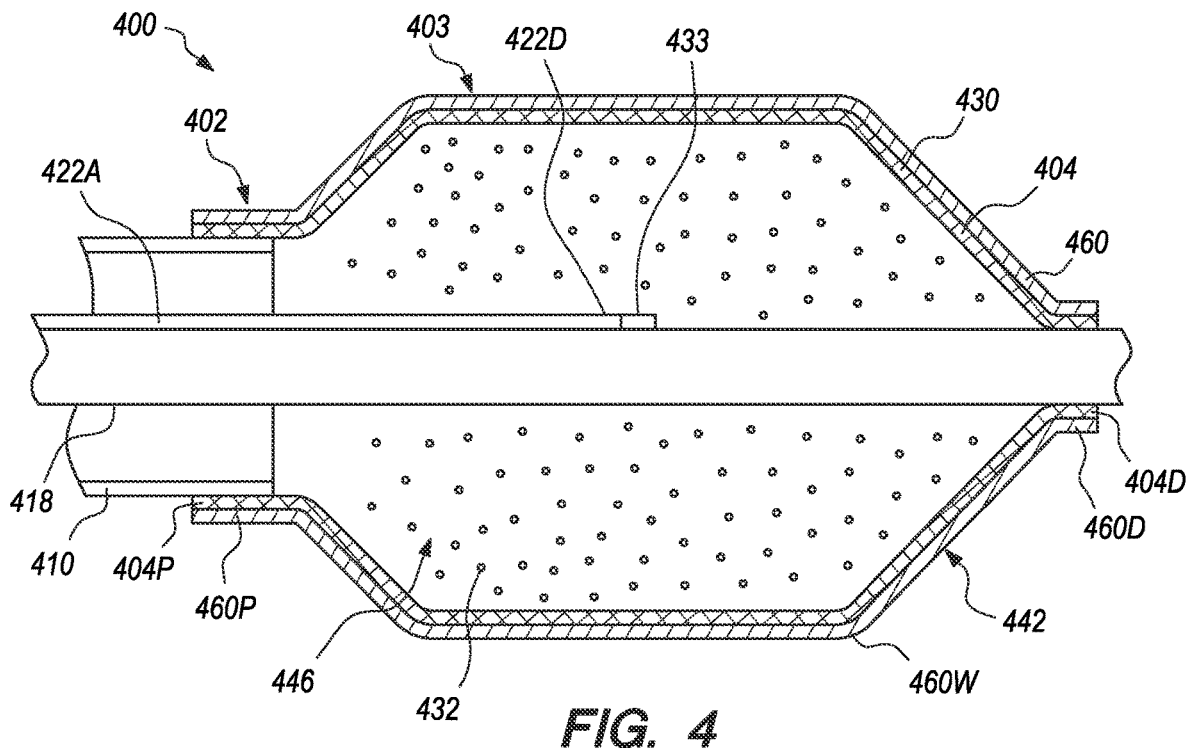
FIG. 4 is a schematic cross-sectional view of a portion of the catheter system including still another embodiment of the balloon integrity protection system.

FIG. 4 is a schematic cross-sectional view of a portion of the catheter system 400 including still another embodiment of the balloon integrity protection system 442. As with the previous embodiments, as illustrated in FIG. 4, the catheter system 400 can include a catheter 402 including a catheter shaft 410, a balloon assembly 403 including a balloon 404 having a balloon wall 430 that defines a balloon interior 446, a balloon proximal end 404P, and a balloon distal end 404D, a balloon fluid 432 that is retained substantially within the balloon interior 446, and a guidewire lumen 418 that extends into and runs through the balloon interior 446; and an energy guide 422A including a plasma generator 433 that is included and/or incorporated at a guide distal end 422D of the energy guide 422A. Additionally, as with the previous embodiments, the catheter system 400, the catheter 402 and/or the balloon assembly 403 can further include the balloon integrity protection system 442 that is operatively coupled to the balloon 404 and that is configured to inhibit rupture or other damage to the balloon 404 or otherwise protect the integrity of the balloon 404 during use of the catheter system 400. Alternatively, in other embodiments, the catheter system 400 can include more components or fewer components than what is specifically illustrated and described herein. For example, certain components that were illustrated in FIG. 1, e.g., the guidewire 112, the light source 124, the power source 125, the system controller 126, the GUI 127, the handle assembly 128, the source manifold 136 and the fluid pump 138, are not specifically illustrated in FIG. 4 for purposes of clarity, but would likely be included in any embodiment of the catheter system 400.

The catheter 402, including the catheter shaft 410, the balloon 404, and the guidewire lumen 418, is generally similar in design and operation to what has been described in detail herein above. Thus, such components will not be described in detail again in relation to the embodiment shown in FIG. 4.

As above, the balloon 404 is selectively movable between a deflated configuration suitable for advancing the catheter 402 through a patient's vasculature, and an inflated configuration suitable for anchoring the catheter 402 in position relative to the treatment site 106 (illustrated in FIG. 1). In some embodiments, the balloon proximal end 404P can be coupled to the catheter shaft 410, and the balloon distal end 404D can be coupled to the guidewire lumen 418. In other embodiments, the catheter shaft 410 can extend fully through the balloon 404, and the balloon distal end 404D can also be coupled to the catheter shaft 410. In still other embodiments, the balloon distal end 404D can be coupled to another structure of the catheter 402. Additionally, the balloon 404 can be inflated with the balloon fluid 432, e.g., from the fluid pump 138 (illustrated in FIG. 1), that is directed into the balloon interior 446 of the balloon 404 via the inflation conduit 140 (illustrated in FIG. 1).

However, in this embodiment, the balloon integrity protection system 442 is somewhat different than in the previous embodiments. In particular, as shown in FIG. 4, the balloon integrity protection system 442 includes a second balloon 460 that substantially completely, if not entirely, encircles the balloon 404 (i.e. with the balloon 404 positioned substantially completely, if not entirely, within the second balloon 460), and is positioned substantially directly adjacent to the balloon 404 such that the balloon assembly 403 comprises a multilayer balloon composite. Additionally, as shown in FIG. 4, the second balloon 460 includes a second balloon proximal end 460P that is coupled to the balloon proximal end 404P of the balloon 404, and a second balloon distal end 460D that is coupled to the balloon distal end 404D of the balloon 404. Further, in contrast to the previous embodiments, in this embodiment, the second balloon 460 includes a second balloon wall 460W that is positioned substantially directly adjacent to the balloon wall 430 of the balloon 404.

In this embodiment, the balloon 404 and the second balloon 460 are formed from different materials from one another. More particularly, in this embodiment, the balloon 404 has a higher melting temperature than the second balloon 460. It is appreciated, however, that the balloon 404 may require the semi-compliance of the second balloon 460 for strength purposes. With such design, the balloon 404 can function to provide desired insulation for the balloon assembly 403, while the second balloon 460 can be utilized to provide pressure containment for the balloon assembly 403.

In one non-exclusive alternative embodiment, the balloon 404 can be formed from a silicone-based material, which has a high melt temperature (e.g., in certain applications around 1700K or similar), and the second balloon 460 can be formed from a more traditional balloon material such as PEBAX™, which has a lower melt temperature (e.g., around 450K or similar). Alternatively, the balloon 404 and/or the second balloon 460 can be formed from other suitable materials, so long as the balloon 404 has a higher melt temperature than the second balloon 460. In certain non-exclusive embodiments, the melt temperature of the balloon 404 can be at least approximately 10, 25, 50, 75, 100, 200, 300, 400, 500, 600, 700, 800, 900, 1000, 1100, 1200, 1300, 1400, or 1500 degrees Kelvin higher than the melt temperature of the second balloon 460.

Figure 5:
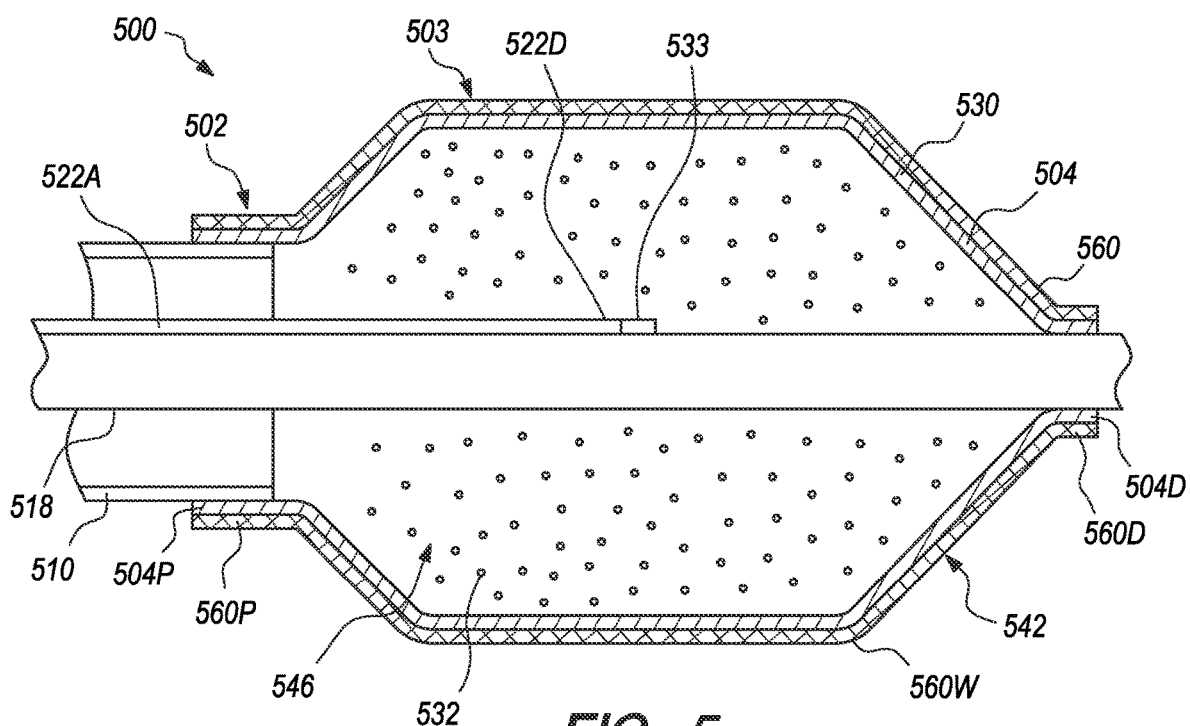
FIG. 5 is a schematic cross-sectional view of a portion of the catheter system including another embodiment of the balloon integrity protection system.

FIG. 5 is a schematic cross-sectional view of a portion of the catheter system 500 including another embodiment of the balloon integrity protection system 542. As with the previous embodiments, as illustrated in FIG. 5, the catheter system 500 can include a catheter 502 including a catheter shaft 510, a balloon assembly 503 including a balloon 504 having a balloon wall 530 that defines a balloon interior 546, a balloon proximal end 504P, and a balloon distal end 504D, a balloon fluid 532 that is retained substantially within the balloon interior 546, and a guidewire lumen 518 that extends into and runs through the balloon interior 546; and an energy guide 522A including a plasma generator 533 that is included and/or incorporated at a guide distal end 522D of the energy guide 522A. Additionally, as with the previous embodiments, the catheter system 500, the catheter 502 and/or the balloon assembly 503 can further include the balloon integrity protection system 542 that is operatively coupled to the balloon 504 and that is configured to inhibit rupture or other damage to the balloon 504 or otherwise protect the integrity of the balloon 504 during use of the catheter system 500. Alternatively, in other embodiments, the catheter system 500 can include more components or fewer components than what is specifically illustrated and described herein. For example, certain components that were illustrated in FIG. 1, e.g., the guidewire 112, the light source 124, the power source 125, the system controller 126, the GUI 127, the handle assembly 128, the source manifold 136 and the fluid pump 138, are not specifically illustrated in FIG. 5 for purposes of clarity, but would likely be included in any embodiment of the catheter system 500.

The catheter 502, including the catheter shaft 510, the balloon 504, and the guidewire lumen 518, is generally similar in design and operation to what has been described in detail herein above. Thus, such components will not be described in detail again in relation to the embodiment shown in FIG. 5.

As above, the balloon 504 is selectively movable between a deflated configuration suitable for advancing the catheter 502 through a patient's vasculature, and an inflated configuration suitable for anchoring the catheter 502 in position relative to the treatment site 106 (illustrated in FIG. 1). In some embodiments, the balloon proximal end 504P can be coupled to the catheter shaft 510, and the balloon distal end 504D can be coupled to the guidewire lumen 518. In other embodiments, the catheter shaft 510 can extend fully through the balloon 504, and the balloon distal end 504D can also be coupled to the catheter shaft 510. In still other embodiments, the balloon distal end 504D can be coupled to another structure of the catheter 502. Additionally, the balloon 504 can be inflated with the balloon fluid 532, e.g., from the fluid pump 138 (illustrated in FIG. 1), that is directed into the balloon interior 546 of the balloon 504 via the inflation conduit 140 (illustrated in FIG. 1).

Further, in this embodiment, the balloon integrity protection system 542 is substantially similar to the embodiment illustrated and described in relation to FIG. 4. In particular, as shown in FIG. 5, the balloon integrity protection system 542 includes a second balloon 560 that substantially completely, if not entirely, encircles the balloon 504 (i.e. with the balloon 504 positioned substantially completely, if not entirely, within the second balloon 560), and is positioned substantially directly adjacent to the balloon 504 such that the balloon assembly 503 comprises a multilayer balloon composite. As shown, the second balloon 560 includes a second balloon proximal end 560P that is coupled to the balloon proximal end 504P of the balloon 504, and a second balloon distal end 560D that is coupled to the balloon distal end 504D of the balloon 504. Additionally, in this embodiment, the second balloon 560 includes a second balloon wall 560W that is positioned substantially directly adjacent to the balloon wall 530 of the balloon 504.

In this embodiment, the balloon 504 and the second balloon 560 are again formed from different materials from one another. However, in this embodiment, the balloon 504 has a lower melting temperature than the second balloon 560. With such design, the balloon 504 is configured to provide the required semi-compliant strength, while the second balloon 560 serves to maintain pressure in the event of the plasma melting or otherwise damaging the balloon 504.

In one non-exclusive alternative embodiment, the balloon 504 can be formed from a more traditional balloon material such as PEBAX™, which has a lower melt temperature (e.g., around 450K or similar), and the second balloon 560 can be formed from a silicone-based material, which has a high melt temperature (e.g., in certain applications around 1700K or similar). Alternatively, the balloon 504 and/or the second balloon 560 can be formed from other suitable materials, so long as the balloon 504 has a lower melt temperature than the second balloon 560. In certain non-exclusive embodiments, the melt temperature of the balloon 504 can be at least approximately 10, 25, 50, 75, 100, 200, 300, 400, 500, 600, 700, 800, 900, 1000, 1100, 1200, 1300, 1400, or 1500 degrees Kelvin lower than the melt temperature of the second balloon 560.

Figure 6:
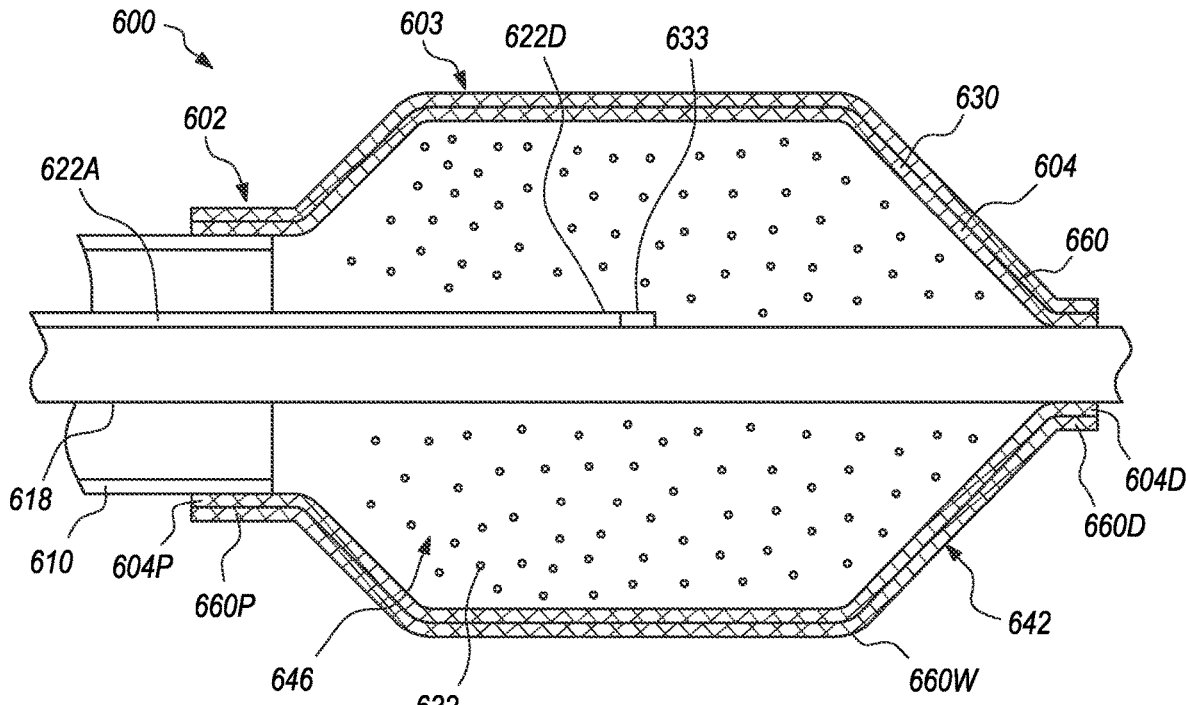
FIG. 6 is a schematic cross-sectional view of a portion of the catheter system including yet another embodiment of the balloon integrity protection system.

FIG. 6 is a schematic cross-sectional view of a portion of the catheter system 600 including yet another embodiment of the balloon integrity protection system 642. As with the previous embodiments, as illustrated in FIG. 6, the catheter system 600 can include a catheter 602 including a catheter shaft 610, a balloon assembly 603 including a balloon 604 having a balloon wall 630 that defines a balloon interior 646, a balloon proximal end 604P, and a balloon distal end 604D, a balloon fluid 632 that is retained substantially within the balloon interior 646, and a guidewire lumen 618 that extends into and runs through the balloon interior 646; and an energy guide 622A including a plasma generator 633 that is included and/or incorporated at a guide distal end 622D of the energy guide 622A. Additionally, as with the previous embodiments, the catheter system 600, the catheter 602 and/or the balloon assembly 603 can further include the balloon integrity protection system 642 that is operatively coupled to the balloon 604 and that is configured to inhibit rupture or other damage to the balloon 604 or otherwise protect the integrity of the balloon 604 during use of the catheter system 600. Alternatively, in other embodiments, the catheter system 600 can include more components or fewer components than what is specifically illustrated and described herein. For example, certain components that were illustrated in FIG. 1, e.g., the guidewire 112, the light source 124, the power source 125, the system controller 126, the GUI 127, the handle assembly 128, the source manifold 136 and the fluid pump 138, are not specifically illustrated in FIG. 6 for purposes of clarity, but would likely be included in any embodiment of the catheter system 600.

The catheter 602, including the catheter shaft 610, the balloon 604, and the guidewire lumen 618, is generally similar in design and operation to what has been described in detail herein above. Thus, such components will not be described in detail again in relation to the embodiment shown in FIG. 6.

As above, the balloon 604 is selectively movable between a deflated configuration suitable for advancing the catheter 602 through a patient's vasculature, and an inflated configuration suitable for anchoring the catheter 602 in position relative to the treatment site 106 (illustrated in FIG. 1). In some embodiments, the balloon proximal end 604P can be coupled to the catheter shaft 610, and the balloon distal end 604D can be coupled to the guidewire lumen 618. In other embodiments, the catheter shaft 610 can extend fully through the balloon 604, and the balloon distal end 604D can also be coupled to the catheter shaft 610. In still other embodiments, the balloon distal end 604D can be coupled to another structure of the catheter 602. Additionally, the balloon 604 can be inflated with the balloon fluid 632, e.g., from the fluid pump 138 (illustrated in FIG. 1), that is directed into the balloon interior 646 of the balloon 604 via the inflation conduit 140 (illustrated in FIG. 1).

Further, in this embodiment, the balloon integrity protection system 642 is somewhat similar to the embodiments illustrated and described in relation to FIGS. 4 and 5. In particular, as shown in FIG. 6, the balloon integrity protection system 642 includes a second balloon 660 that substantially completely, if not entirely, encircles the balloon 604 (i.e. with the balloon 604 positioned substantially completely, if not entirely, within the second balloon 660), and is positioned substantially directly adjacent to the balloon 604 such that the balloon assembly 603 comprises a multi-layer balloon composite. As shown, the second balloon 660 includes a second balloon proximal end 660P that is coupled to the balloon proximal end 604P of the balloon 604, and a second balloon distal end 660D that is coupled to the balloon distal end 604D of the balloon 604. Additionally, in this embodiment, the second balloon 660 includes a second balloon wall 660W that is positioned substantially directly adjacent to the balloon wall 630 of the balloon 604.

In this embodiment, the balloon 604 and the second balloon 660 are again formed from different materials from one another. More particularly, in this embodiment, the balloon 604 can be formed from an open cell foam material and the second balloon 660 can be formed from a more traditional balloon material, e.g., PEBAX™. As described in this embodiment, the open cell foam material of the balloon 604 serves to separate the balloon material of the second balloon 660 from the plasma that is being formed within the balloon fluid 632 within the balloon interior 646. Additionally, in one such embodiment, voids that are formed within the open cell foam material of the balloon 604 can be filled with an inflation media that serves as an additional insulation layer between the plasma and the balloon material of the second balloon 660.

Figure 7:
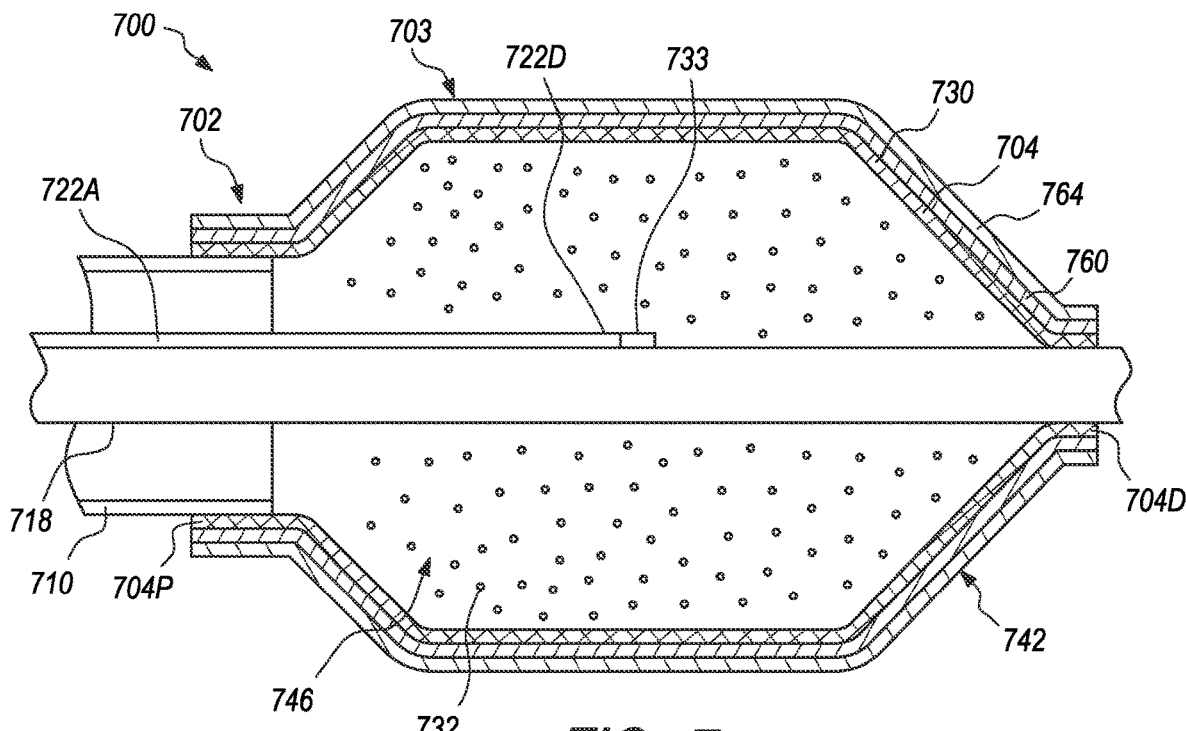
FIG. 7 is a schematic cross-sectional view of a portion of the catheter system including another embodiment of the balloon integrity protection system.

FIG. 7 is a schematic cross-sectional view of a portion of the catheter system 700 including another embodiment of the balloon integrity protection system 742. As with the previous embodiments, as illustrated in FIG. 7, the catheter system 700 can include a catheter 702 including a catheter shaft 710, a balloon assembly 703 including a balloon 704 having a balloon wall 730 that defines a balloon interior 746, a balloon proximal end 704P, and a balloon distal end 704D, a balloon fluid 732 that is retained substantially within the balloon interior 746, and a guidewire lumen 718 that extends into and runs through the balloon interior 746; and an energy guide 722A including a plasma generator 733 that is included and/or incorporated at a guide distal end 722D of the energy guide 722A. Additionally, as with the previous embodiments, the catheter system 700, the catheter 702 and/or the balloon assembly 703 can further include the balloon integrity protection system 742 that is operatively coupled to the balloon 704 and that is configured to inhibit rupture or other damage to the balloon 704 or otherwise protect the integrity of the balloon 704 during use of the catheter system 700. Alternatively, in other embodiments, the catheter system 700 can include more components or fewer components than what is specifically illustrated and described herein. For example, certain components that were illustrated in FIG. 1, e.g., the guidewire 112, the light source 124, the power source 125, the system controller 126, the GUI 127, the handle assembly 128, the source manifold 136 and the fluid pump 138, are not specifically illustrated in FIG. 7 for purposes of clarity, but would likely be included in any embodiment of the catheter system 700.

The catheter 702, including the catheter shaft 710, the balloon 704, and the guidewire lumen 718, is generally similar in design and operation to what has been described in detail herein above. Thus, such components will not be described in detail again in relation to the embodiment shown in FIG. 7.

As above, the balloon 704 is selectively movable between a deflated configuration suitable for advancing the catheter 702 through a patient's vasculature, and an inflated configuration suitable for anchoring the catheter 702 in position relative to the treatment site 106 (illustrated in FIG. 1). In some embodiments, the balloon proximal end 704P can be coupled to the catheter shaft 710, and the balloon distal end 704D can be coupled to the guidewire lumen 718. In other embodiments, the catheter shaft 710 can extend fully through the balloon 704, and the balloon distal end 704D can also be coupled to the catheter shaft 710. In still other embodiments, the balloon distal end 704D can be coupled to another structure of the catheter 702. Additionally, the balloon 704 can be inflated with the balloon fluid 732, e.g., from the fluid pump 138 (illustrated in FIG. 1), that is directed into the balloon interior 746 of the balloon 704 via the inflation conduit 140 (illustrated in FIG. 1).

However, in this embodiment, the balloon integrity protection system 742 is somewhat different than in the previous embodiments. In particular, as shown in FIG. 7, the balloon integrity protection system 742 includes a second balloon 760 and a third balloon 764 that are positioned substantially directly adjacent to one another to form a multilayer balloon composite. More specifically, the balloon 704 is shown as the inner most balloon, the second balloon 760 is positioned substantially directly adjacent to the balloon 704 and substantially completely, if not entirely, encircles the balloon 704, and the third balloon 764 is the outer most balloon that is positioned substantially directly adjacent to the second balloon 760 and substantially completely, if not entirely, encircles the second balloon 760.

In this embodiment, the balloon 704 and the third balloon 764 can be formed from more traditional balloon materials, e.g., PEBAX™ or another suitable balloon material, and the second balloon 760 can be formed from a non-traditional balloon material. In such embodiment, the non-traditional balloon material of the second balloon 760 (i.e. the middle balloon) can be configured to reflect and/or absorb light and heat that may be generated in the balloon assembly 703. In certain non-exclusive alternative embodiments, the second balloon 760 can be formed from one or more of a metallic foil, a carbon foil, a closed cell membrane filled with gas or liquid, or another suitable material that can reflect/absorb light and heat.

Figure 8:
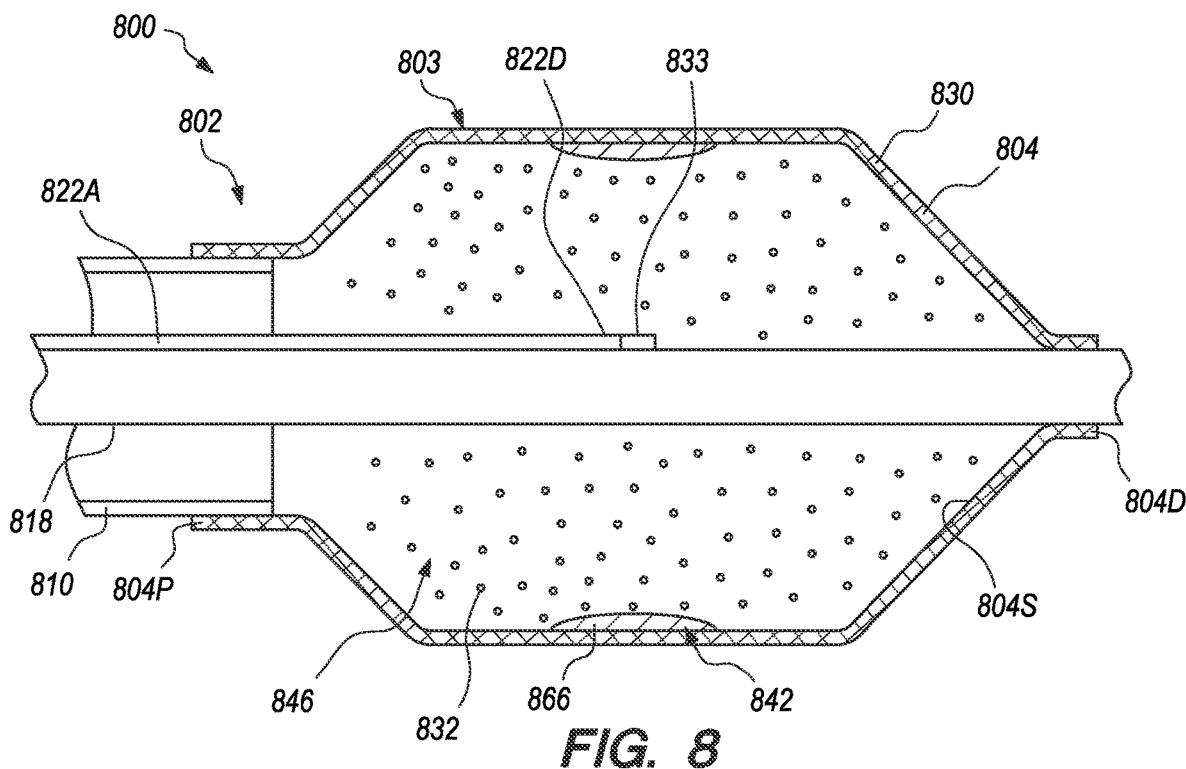
FIG. 8 is a schematic cross-sectional view of a portion of the catheter system including still another embodiment of the balloon integrity protection system.

FIG. 8 is a schematic cross-sectional view of a portion of the catheter system 800 including still another embodiment of the balloon integrity protection system 842. As with the previous embodiments, as illustrated in FIG. 8, the catheter system 800 can include a catheter 802 including a catheter shaft 810, a balloon assembly 803 including a balloon 804 having a balloon wall 830 that defines a balloon interior 846, a balloon proximal end 804P, and a balloon distal end 804D, a balloon fluid 832 that is retained substantially within the balloon interior 846, and a guidewire lumen 818 that extends into and runs through the balloon interior 846; and an energy guide 822A including a plasma generator 833 that is included and/or incorporated at a guide distal end 822D of the energy guide 822A. Additionally, as with the previous embodiments, the catheter system 800, the catheter 802 and/or the balloon assembly 803 can further include the balloon integrity protection system 842 that is operatively coupled to the balloon 804 and that is configured to inhibit rupture or other damage to the balloon 804 or otherwise protect the integrity of the balloon 804 during use of the catheter system 800. Alternatively, in other embodiments, the catheter system 800 can include more components or fewer components than what is specifically illustrated and described herein. For example, certain components that were illustrated in FIG. 1, e.g., the guidewire 112, the light source 124, the power source 125, the system controller 126, the GUI 127, the handle assembly 128, the source manifold 136 and the fluid pump 138, are not specifically illustrated in FIG. 8 for purposes of clarity, but would likely be included in any embodiment of the catheter system 800.

The catheter 802, including the catheter shaft 810, the balloon 804, and the guidewire lumen 818, is generally similar in design and operation to what has been described in detail herein above. Thus, such components will not be described in detail again in relation to the embodiment shown in FIG. 8.

As above, the balloon 804 is selectively movable between a deflated configuration suitable for advancing the catheter 802 through a patient's vasculature, and an inflated configuration suitable for anchoring the catheter 802 in position relative to the treatment site 106 (illustrated in FIG. 1). In some embodiments, the balloon proximal end 804P can be coupled to the catheter shaft 810, and the balloon distal end 804D can be coupled to the guidewire lumen 818. In other embodiments, the catheter shaft 810 can extend fully through the balloon 804, and the balloon distal end 804D can also be coupled to the catheter shaft 810. In still other embodiments, the balloon distal end 804D can be coupled to another structure of the catheter 802. Additionally, the balloon 804 can be inflated with the balloon fluid 832, e.g., from the fluid pump 138 (illustrated in FIG. 1), that is directed into the balloon interior 846 of the balloon 804 via the inflation conduit 140 (illustrated in FIG. 1).

However, in this embodiment, the balloon integrity protection system 842 is somewhat different than in the previous embodiments. In particular, as shown in FIG. 8, the balloon integrity protection system 842 includes composite material 866 that is added onto a surface 804S of the balloon 804, e.g., an inner surface of the balloon 804, only near the plasma generators 833 to provide a selective balloon composite. For example, as shown in FIG. 8, the composite material 866 can be added onto the surface 804S of the balloon 804 as one or more islands or circumferentially about the surface 804S of the balloon 804. With such design, the goal is to maintain the native balloon performance of the balloon 804, e.g., in terms of crossability, trackability, pushability, etc., as close as possible, while still providing a certain measure of insulation to protect the integrity of the balloon 804, i.e. to inhibit rupture or other damage to the balloon 804, during use of the catheter system 800.

The material for the composite material 866 can be varied to suit the specific requirements of the catheter system 800, the balloon assembly 803 and/or the balloon integrity protection system 842. In certain embodiments, the composite material 866 may be formed from a material having a higher melt temperature and/or having the ability to absorb/reflect light and heat substantially better than the native balloon material that is used to form the balloon 804. In certain non-exclusive alternative embodiments, the composite material 866 can be formed from one or more of a metallic foil, a carbon foil, a closed cell membrane filled with gas or liquid, or another suitable material that can reflect/absorb light and heat.

Additionally, it is appreciated that the composite material 866 can be added onto the surface 804S of the balloon 804 using any appropriate methods and/or machinery. For example, one non-exclusive machine capable of such operation is a PLA Giken Extruder, available from PLA Giken Co., Ltd., of Osaka, Japan. Alternatively, the composite material 866 can be added onto the surface 804S of the balloon 804 using another appropriate method or machine.

Figure 9:
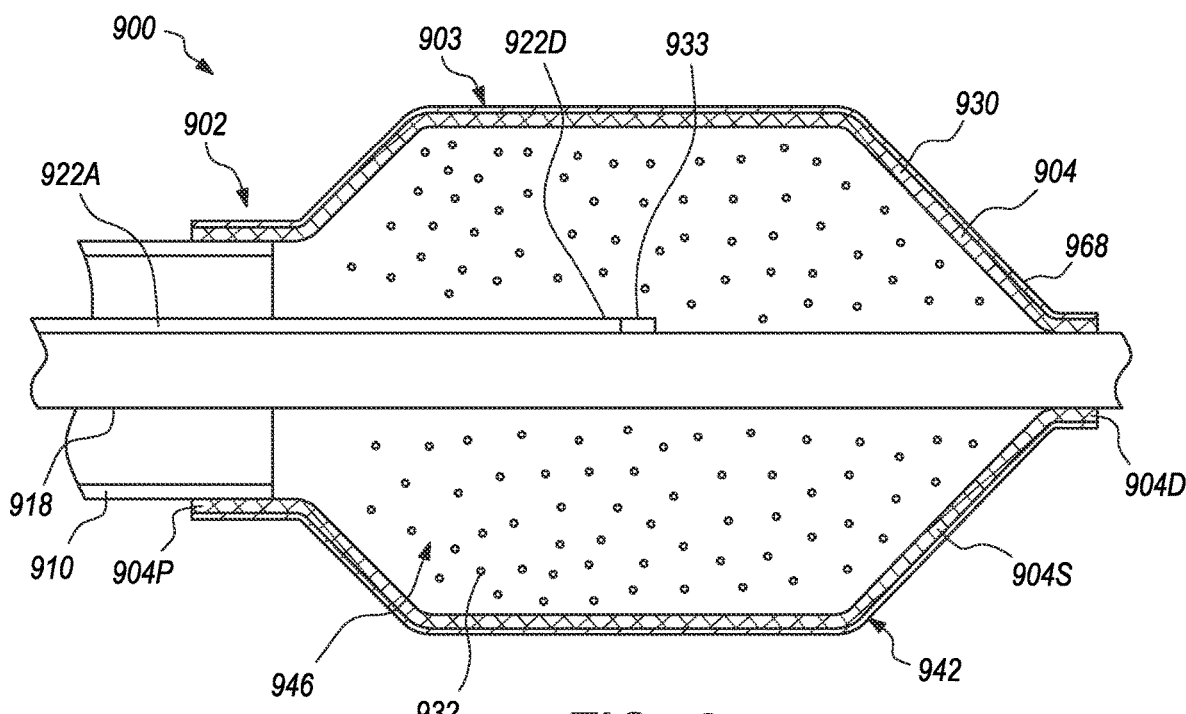
FIG. 9 is a schematic cross-sectional view of a portion of the catheter system including another embodiment of the balloon integrity protection system.

FIG. 9 is a schematic cross-sectional view of a portion of the catheter system 900 including another embodiment of the balloon integrity protection system 942. As with the previous embodiments, as illustrated in FIG. 9, the catheter system 900 can include a catheter 902 including a catheter shaft 910, a balloon assembly 903 including a balloon 904 having a balloon wall 930 that defines a balloon interior 946, a balloon proximal end 904P, and a balloon distal end 904D, a balloon fluid 932 that is retained substantially within the balloon interior 946, and a guidewire lumen 918 that extends into and runs through the balloon interior 946; and an energy guide 922A including a plasma generator 933 that is included and/or incorporated at a guide distal end 922D of the energy guide 922A. Additionally, as with the previous embodiments, the catheter system 900, the catheter 902 and/or the balloon assembly 903 can further include the balloon integrity protection system 942 that is operatively coupled to the balloon 904 and that is configured to inhibit rupture or other damage to the balloon 904 or otherwise protect the integrity of the balloon 904 during use of the catheter system 900. Alternatively, in other embodiments, the catheter system 900 can include more components or fewer components than what is specifically illustrated and described herein. For example, certain components that were illustrated in FIG. 1, e.g., the guidewire 112, the light source 124, the power source 125, the system controller 126, the GUI 127, the handle assembly 128, the source manifold 136 and the fluid pump 138, are not specifically illustrated in FIG. 9 for purposes of clarity, but would likely be included in any embodiment of the catheter system 900.

The catheter 902, including the catheter shaft 910, the balloon 904, and the guidewire lumen 918, is generally similar in design and operation to what has been described in detail herein above. Thus, such components will not be described in detail again in relation to the embodiment shown in FIG. 9.

As above, the balloon 904 is selectively movable between a deflated configuration suitable for advancing the catheter 902 through a patient's vasculature, and an inflated configuration suitable for anchoring the catheter 902 in position relative to the treatment site 106 (illustrated in FIG. 1). In some embodiments, the balloon proximal end 904P can be coupled to the catheter shaft 910, and the balloon distal end 904D can be coupled to the guidewire lumen 918. In other embodiments, the catheter shaft 910 can extend fully through the balloon 904, and the balloon distal end 904D can also be coupled to the catheter shaft 910. In still other embodiments, the balloon distal end 904D can be coupled to another structure of the catheter 902. Additionally, the balloon 904 can be inflated with the balloon fluid 932, e.g., from the fluid pump 138 (illustrated in FIG. 1), that is directed into the balloon interior 946 of the balloon 904 via the inflation conduit 140 (illustrated in FIG. 1).

However, in this embodiment, the balloon integrity protection system 942 is somewhat different than in the previous embodiments. In particular, as shown in FIG. 9, the balloon integrity protection system 942 includes a braided material layer 968, e.g., a high strength fiber, that is wrapped around a surface 904S of the balloon 904, e.g., an outer surface of the balloon 904, to provide a braided balloon composite. For example, in one such embodiment, the balloon 904 can be formed from a traditional balloon material, and the braided material layer 968 can be wrapped around the surface 904S of the balloon 904 in a particular manner so as to effectively provide desired hoop and axial strength. With such design, the balloon assembly 903 is configured to be compliant, but also designed to keep the pressure within the balloon 904.

Additionally, in this embodiment, the braid pattern for the braided material layer 968 can be wrapped in such a manner such that it is specifically configured to shorten the balloon 904 upon inflation of the balloon 904. More particularly, in such embodiment, as the balloon 904 shortens during inflation, the catheter shaft 910 is flexed away from the wall of the blood vessel 108 (illustrated in FIG. 1), thereby protecting the balloon material from the high temperature plasma.

It is appreciated that the braided material layer 968 can be formed from any suitable materials. For example, in certain non-exclusive alternative embodiments, the braided material layer 968 can be formed from one or more of nitinol, stainless steel, carbon, aramid, rayon, polyester, aromatic polyester (such as Vectran), nylon, and natural (silk, wool, cotton and linen) fibers and/or other suitable materials.

Figure 10:
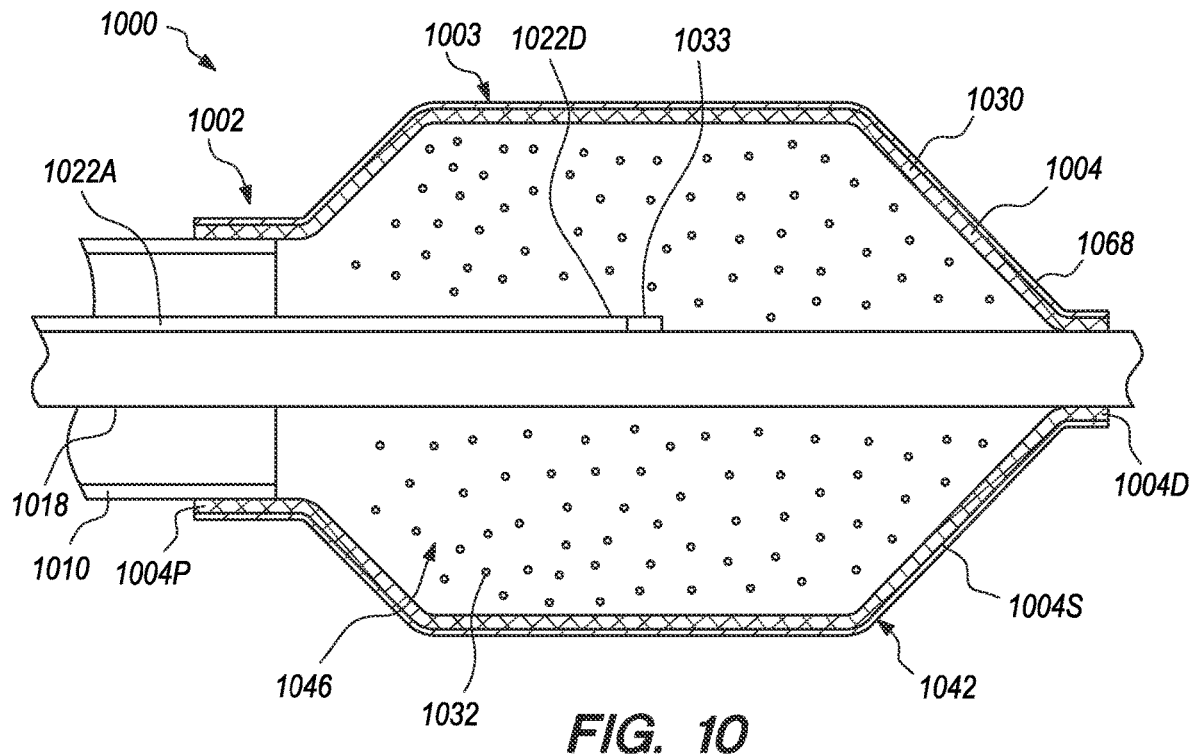
FIG. 10 is a schematic cross-sectional view of a portion of the catheter system including yet another embodiment of the balloon integrity protection system.

FIG. 10 is a schematic cross-sectional view of a portion of the catheter system 1000 including yet another embodiment of the balloon integrity protection system 1042. As with the previous embodiments, as illustrated in FIG. 10, the catheter system 1000 can include a catheter 1002 including a catheter shaft 1010, a balloon assembly 1003 including a balloon 1004 having a balloon wall 1030 that defines a balloon interior 1046, a balloon proximal end 1004P, and a balloon distal end 1004D, a balloon fluid 1032 that is retained substantially within the balloon interior 1046, and a guidewire lumen 1018 that extends into and runs through the balloon interior 1046; and an energy guide 1022A including a plasma generator 1033 that is included and/or incorporated at a guide distal end 1022D of the energy guide 1022A. Additionally, as with the previous embodiments, the catheter system 1000, the catheter 1002 and/or the balloon assembly 1003 can further include the balloon integrity protection system 1042 that is operatively coupled to the balloon 1004 and that is configured to inhibit rupture or other damage to the balloon 1004 or otherwise protect the integrity of the balloon 1004 during use of the catheter system 1000. Alternatively, in other embodiments, the catheter system 1000 can include more components or fewer components than what is specifically illustrated and described herein. For example, certain components that were illustrated in FIG. 1, e.g., the guidewire 112, the light source 124, the power source 125, the system controller 126, the GUI 127, the handle assembly 128, the source manifold 136 and the fluid pump 138, are not specifically illustrated in FIG. 10 for purposes of clarity, but would likely be included in any embodiment of the catheter system 1000.

The catheter 1002, including the catheter shaft 1010, the balloon 1004, and the guidewire lumen 1018, is generally similar in design and operation to what has been described in detail herein above. Thus, such components will not be described in detail again in relation to the embodiment shown in FIG. 10.

As above, the balloon 1004 is selectively movable between a deflated configuration suitable for advancing the catheter 1002 through a patient's vasculature, and an inflated configuration suitable for anchoring the catheter 1002 in position relative to the treatment site 106 (illustrated in FIG. 1). In some embodiments, the balloon proximal end 1004P can be coupled to the catheter shaft 1010, and the balloon distal end 1004D can be coupled to the guidewire lumen 1018. In other embodiments, the catheter shaft 1010 can extend fully through the balloon 1004, and the balloon distal end 1004D can also be coupled to the catheter shaft 1010. In still other embodiments, the balloon distal end 1004D can be coupled to another structure of the catheter 1002. Additionally, the balloon 1004 can be inflated with the balloon fluid 1032, e.g., from the fluid pump 138 (illustrated in FIG. 1), that is directed into the balloon interior 1046 of the balloon 1004 via the inflation conduit 140 (illustrated in FIG. 1).

Further, in this embodiment, the balloon integrity protection system 1042 is somewhat similar to the embodiment illustrated and described in relation to FIG. 9. In particular, as shown in FIG. 10, the balloon integrity protection system 1042 includes a braided material layer 1068, e.g., a high strength fiber, that is wrapped around a surface 1004S of the balloon 1004, e.g., an outer surface of the balloon 1004, to provide a braided balloon composite. In one such embodiment, the balloon 1004 can be formed from a traditional balloon material and the braided material layer 1068 can be formed from a high strength fiber that is wrapped around the surface 1004S of the balloon 1004 in such a manner to provide hoop and axial strength. Additionally, in this embodiment, the braided material layer 1068 can be wrapped around the surface 1004S of the balloon 1004 in a manner so as to allow pinholes, but to still minimize the possibility of balloon rupture. Stated in another manner, the braided material layer 1068 is specifically designed to allow small tears in the balloon 1004, but is wrapped in a manner and/or made from a material to inhibit propagation of the tears in the balloon 1004.

Additionally, in this embodiment, the braided material layer 1068 may further be wrapped in such a manner so as to cause the catheter shaft 1010 to flex away from the wall of the blood vessel 108 (illustrated in FIG. 1) to provide additional clearance between the plasma and the balloon material.

It is appreciated that the braided material layer 1068 can be formed from any suitable materials. For example, in certain non-exclusive alternative embodiments, the braided material layer 1068 can be formed from one or more of nitinol, stainless steel, carbon, aramid, rayon, polyester, aromatic polyester (such as Vectran), nylon, and natural (silk, wool, cotton and linen) fibers and/or other suitable materials.

Figure 11:
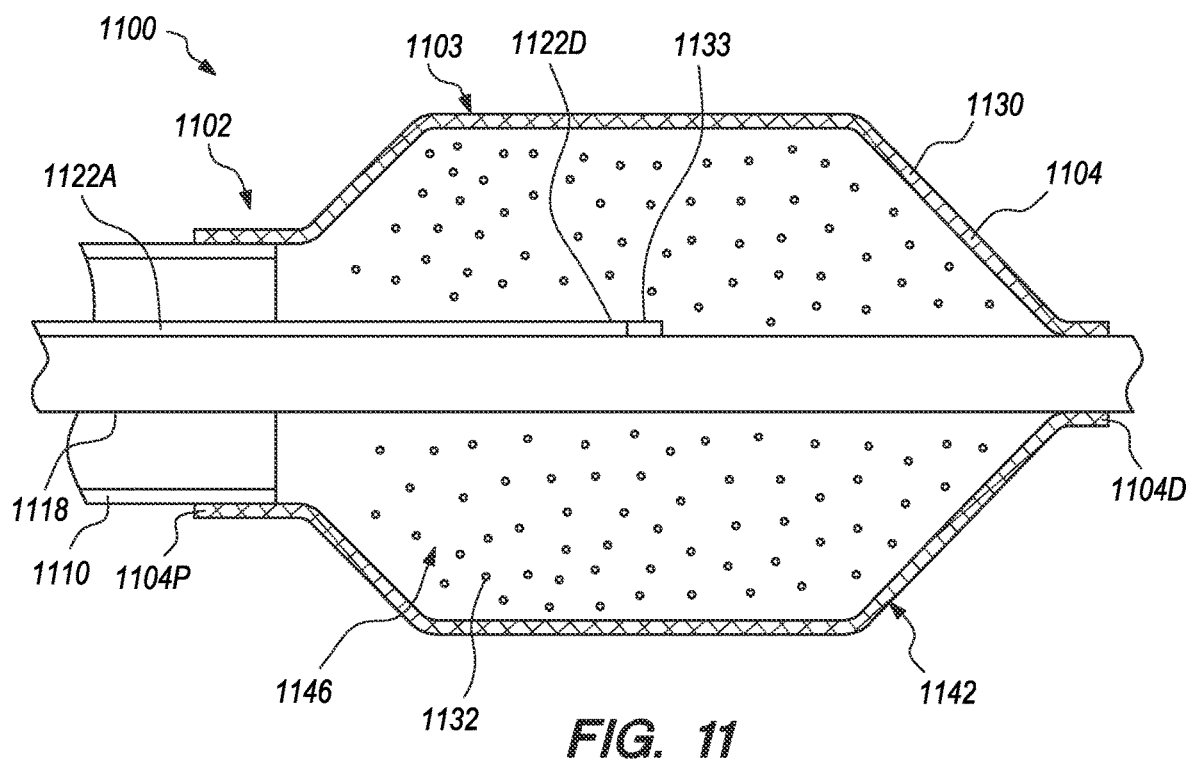
FIG. 11 is a schematic cross-sectional view of a portion of the catheter system including another embodiment of the balloon integrity protection system.

FIG. 11 is a schematic cross-sectional view of a portion of the catheter system 1100 including another embodiment of the balloon integrity protection system 1142. As with the previous embodiments, as illustrated in FIG. 11, the catheter system 1100 can include a catheter 1102 including a catheter shaft 1110, a balloon assembly 1103 including a balloon 1104 having a balloon wall 1130 that defines a balloon interior 1146, a balloon proximal end 1104P, and a balloon distal end 1104D, a balloon fluid 1132 that is retained substantially within the balloon interior 1146, and a guidewire lumen 1118 that extends into and runs through the balloon interior 1146; and an energy guide 1122A including a plasma generator 1133 that is included and/or incorporated at a guide distal end 1122D of the energy guide 1122A. Additionally, as with the previous embodiments, the catheter system 1100, the catheter 1102 and/or the balloon assembly 1103 can further include the balloon integrity protection system 1142 that is operatively coupled to the balloon 1104 and that is configured to inhibit rupture or other damage to the balloon 1104 or otherwise protect the integrity of the balloon 1104 during use of the catheter system 1100. Alternatively, in other embodiments, the catheter system 1100 can include more components or fewer components than what is specifically illustrated and described herein. For example, certain components that were illustrated in FIG. 1, e.g., the guidewire 112, the light source 124, the power source 125, the system controller 126, the GUI 127, the handle assembly 128, the source manifold 136 and the fluid pump 138, are not specifically illustrated in FIG. 11 for purposes of clarity, but would likely be included in any embodiment of the catheter system 1100.

The catheter 1102, including the catheter shaft 1110, the balloon 1104, and the guidewire lumen 1118, is generally similar in design and operation to what has been described in detail herein above. Thus, such components will not be described in detail again in relation to the embodiment shown in FIG. 11.

As above, the balloon 1104 is selectively movable between a deflated configuration suitable for advancing the catheter 1102 through a patient's vasculature, and an inflated configuration suitable for anchoring the catheter 1102 in position relative to the treatment site 106 (illustrated in FIG. 1). In some embodiments, the balloon proximal end 1104P can be coupled to the catheter shaft 1110, and the balloon distal end 1104D can be coupled to the guidewire lumen 1118. In other embodiments, the catheter shaft 1110 can extend fully through the balloon 1104, and the balloon distal end 1104D can also be coupled to the catheter shaft 1110. In still other embodiments, the balloon distal end 1104D can be coupled to another structure of the catheter 1102. Additionally, the balloon 1104 can be inflated with the balloon fluid 1132, e.g., from the fluid pump 138 (illustrated in FIG. 1), that is directed into the balloon interior 1146 of the balloon 1104 via the inflation conduit 140 (illustrated in FIG. 1).

However, in this embodiment, the balloon integrity protection system 1142 is somewhat different than in the previous embodiments. In particular, as shown in FIG. 11, the balloon integrity protection system 1142 includes the balloon 1104 being formed as an electro-spun balloon, e.g., as a fine braid variation, through a process of electrospinning. Electrospinning is a fiber production method which uses electric force to draw charged threads of polymer solutions or polymer melts up to fiber diameters in the order of some hundred nanometers. In particular, when a sufficiently high voltage is applied to a liquid droplet, the body of the liquid becomes charged, and electrostatic repulsion counteracts the surface tension and the droplet is stretched; and at a critical point a stream of liquid erupts from the surface.

In such embodiment, it is appreciated that the balloon 1104 can be formed as a gas-tight braided balloon, i.e. with a melt temperature that is significantly higher than the melt temperature for traditional balloon materials. As such, the electro-spun balloon material provides greater temperature protection against plasma than traditional balloon materials. Additionally, it is further appreciated that in different embodiments, the electro-spun balloon material can be used alone or as a composite with traditional balloon materials.

Figure 12:
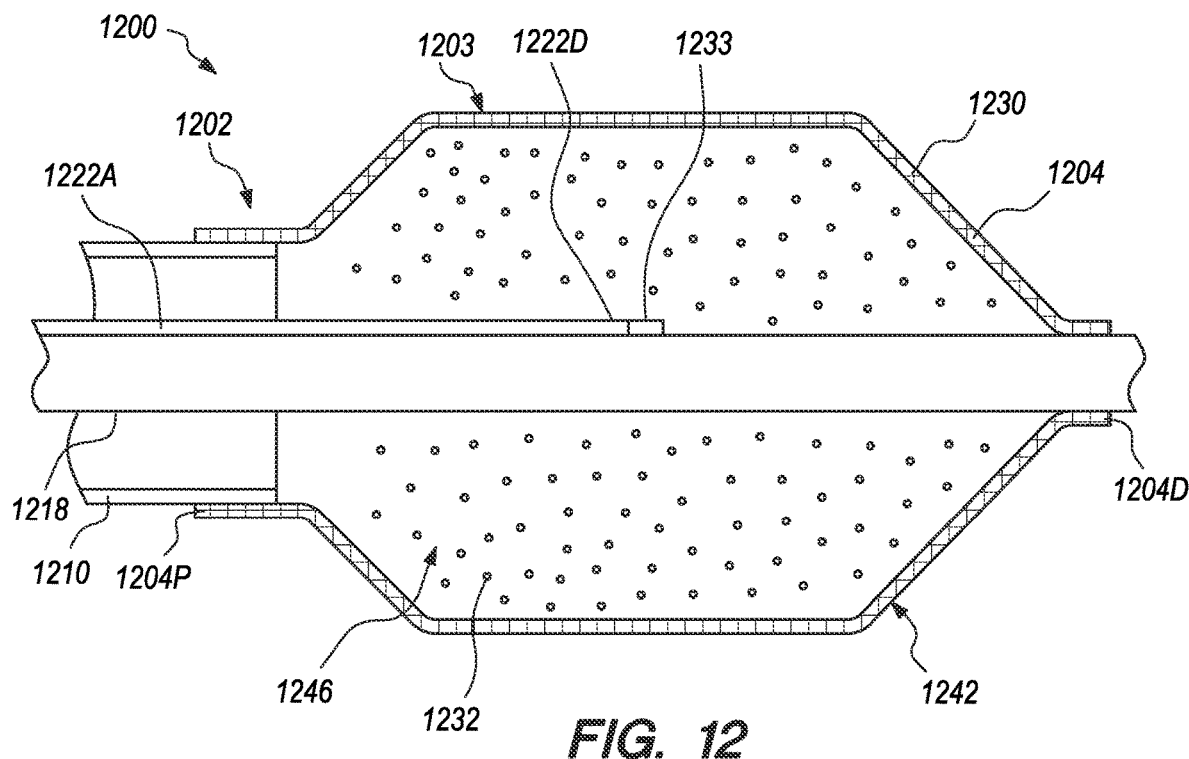
FIG. 12 is a schematic cross-sectional view of a portion of the catheter system including still another embodiment of the balloon integrity protection system.

FIG. 12 is a schematic cross-sectional view of a portion of the catheter system 1200 including still another embodiment of the balloon integrity protection system 1242. As with the previous embodiments, as illustrated in FIG. 12, the catheter system 1200 can include a catheter 1202 including a catheter shaft 1210, a balloon assembly 1203 including a balloon 1204 having a balloon wall 1230 that defines a balloon interior 1246, a balloon proximal end 1204P, and a balloon distal end 1204D, a balloon fluid 1232 that is retained substantially within the balloon interior 1246, and a guidewire lumen 1218 that extends into and runs through the balloon interior 1246; and an energy guide 1222A including a plasma generator 1233 that is included and/or incorporated at a guide distal end 1222D of the energy guide 1222A. Additionally, as with the previous embodiments, the catheter system 1200, the catheter 1202 and/or the balloon assembly 1203 can further include the balloon integrity protection system 1242 that is operatively coupled to the balloon 1204 and that is configured to inhibit rupture or other damage to the balloon 1204 or otherwise protect the integrity of the balloon 1204 during use of the catheter system 1200. Alternatively, in other embodiments, the catheter system 1200 can include more components or fewer components than what is specifically illustrated and described herein. For example, certain components that were illustrated in FIG. 1, e.g., the guidewire 112, the light source 124, the power source 125, the system controller 126, the GUI 127, the handle assembly 128, the source manifold 136 and the fluid pump 138, are not specifically illustrated in FIG. 12 for purposes of clarity, but would likely be included in any embodiment of the catheter system 1200.

The catheter 1202, including the catheter shaft 1210, the balloon 1204, and the guidewire lumen 1218, is generally similar in design and operation to what has been described in detail herein above. Thus, such components will not be described in detail again in relation to the embodiment shown in FIG. 12.

As above, the balloon 1204 is selectively movable between a deflated configuration suitable for advancing the catheter 1202 through a patient's vasculature, and an inflated configuration suitable for anchoring the catheter 1202 in position relative to the treatment site 106 (illustrated in FIG. 1). In some embodiments, the balloon proximal end 1204P can be coupled to the catheter shaft 1210, and the balloon distal end 1204D can be coupled to the guidewire lumen 1218. In other embodiments, the catheter shaft 1210 can extend fully through the balloon 1204, and the balloon distal end 1204D can also be coupled to the catheter shaft 1210. In still other embodiments, the balloon distal end 1204D can be coupled to another structure of the catheter 1202. Additionally, the balloon 1204 can be inflated with the balloon fluid 1232, e.g., from the fluid pump 138 (illustrated in FIG. 1), that is directed into the balloon interior 1246 of the balloon 1204 via the inflation conduit 140 (illustrated in FIG. 1).

However, in this embodiment, the balloon integrity protection system 1242 is somewhat different than in the previous embodiments. In particular, as shown in FIG. 12, the balloon integrity protection system 1242 includes the balloon 1204 being from electrically conductive balloon material. In one non-exclusive alternative embodiment, the balloon 1204 can be formed from PEBAX™ MV-1074. Alternatively, the balloon 1204 can be formed from one or more of PEBAX™ MH-1657, Polyacetylene, polypyrrole, polyindole, polyaniline, poly(p-phenylene vinylene), poly (thiophene), poly(3,4-ethylenedioxythiophene), poly(p-phenylene sulfide) and/or other suitable anti-static materials.

With such design, in the event that an arc plasma contacts the balloon 1204, the material used for the balloon 1204 can function to spread the distribution of charge to thus minimize focused electrocution or electrocautery.

Figure 13:
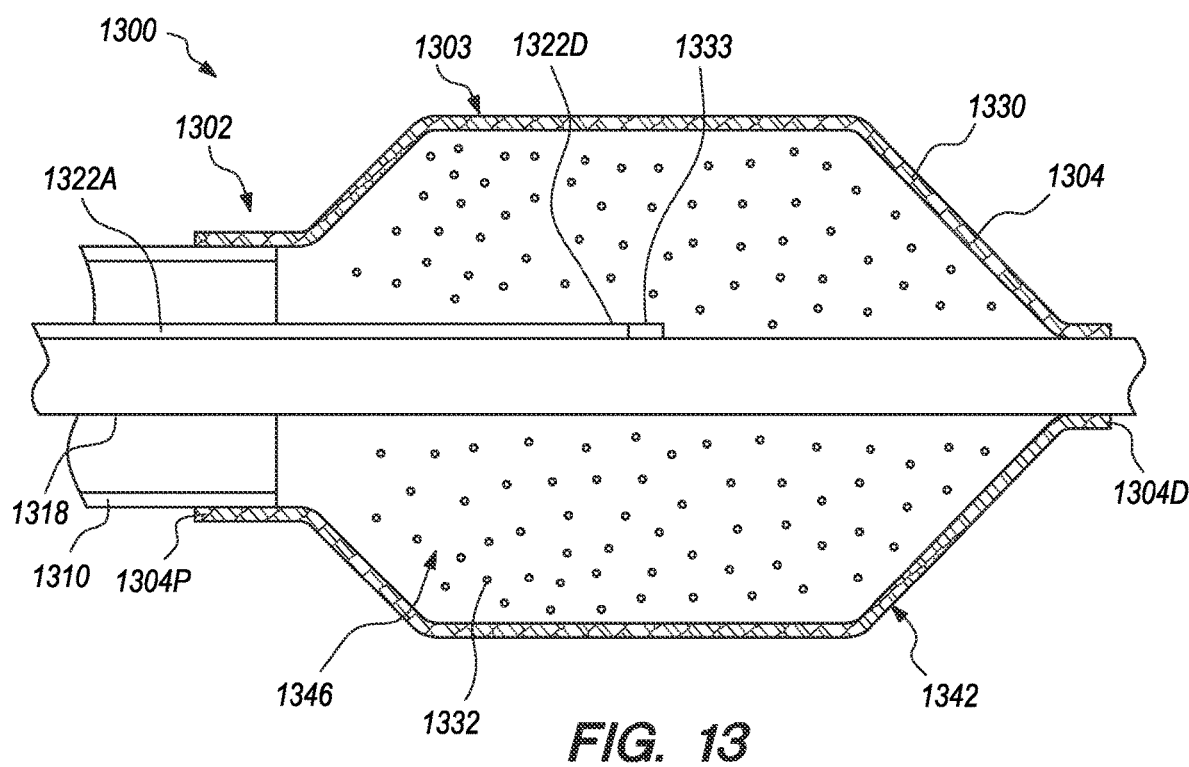
FIG. 13 is a schematic cross-sectional view of a portion of the catheter system including another embodiment of the balloon integrity protection system.

FIG. 13 is a schematic cross-sectional view of a portion of the catheter system 1300 including another embodiment of the balloon integrity protection system 1342. As with the previous embodiments, as illustrated in FIG. 13, the catheter system 1300 can include a catheter 1302 including a catheter shaft 1310, a balloon assembly 1303 including a balloon 1304 having a balloon wall 1330 that defines a balloon interior 1346, a balloon proximal end 1304P, and a balloon distal end 1304D, a balloon fluid 1332 that is retained substantially within the balloon interior 1346, and a guidewire lumen 1318 that extends into and runs through the balloon interior 1346; and an energy guide 1322A including a plasma generator 1333 that is included and/or incorporated at a guide distal end 1322D of the energy guide 1322A. Additionally, as with the previous embodiments, the catheter system 1300, the catheter 1302 and/or the balloon assembly 1303 can further include the balloon integrity protection system 1342 that is operatively coupled to the balloon 1304 and that is configured to inhibit rupture or other damage to the balloon 1304 or otherwise protect the integrity of the balloon 1304 during use of the catheter system 1300. Alternatively, in other embodiments, the catheter system 1300 can include more components or fewer components than what is specifically illustrated and described herein. For example, certain components that were illustrated in FIG. 1, e.g., the guidewire 112, the light source 124, the power source 125, the system controller 126, the GUI 127, the handle assembly 128, the source manifold 136 and the fluid pump 138, are not specifically illustrated in FIG. 13 for purposes of clarity, but would likely be included in any embodiment of the catheter system 1300.

The catheter 1302, including the catheter shaft 1310, the balloon 1304, and the guidewire lumen 1318, is generally similar in design and operation to what has been described in detail herein above. Thus, such components will not be described in detail again in relation to the embodiment shown in FIG. 13.

As above, the balloon 1304 is selectively movable between a deflated configuration suitable for advancing the catheter 1302 through a patient's vasculature, and an inflated configuration suitable for anchoring the catheter 1302 in position relative to the treatment site 106 (illustrated in FIG. 1). In some embodiments, the balloon proximal end 1304P can be coupled to the catheter shaft 1310, and the balloon distal end 1304D can be coupled to the guidewire lumen 1318. In other embodiments, the catheter shaft 1310 can extend fully through the balloon 1304, and the balloon distal end 1304D can also be coupled to the catheter shaft 1310. In still other embodiments, the balloon distal end 1304D can be coupled to another structure of the catheter 1302. Additionally, the balloon 1304 can be inflated with the balloon fluid 1332, e.g., from the fluid pump 138 (illustrated in FIG. 1), that is directed into the balloon interior 1346 of the balloon 1304 via the inflation conduit 140 (illustrated in FIG. 1).

However, in this embodiment, the balloon integrity protection system 1342 is somewhat different than in the previous embodiments. In particular, as shown in FIG. 13, the balloon integrity protection system 1342 includes the balloon 1304 being from thermally conductive balloon material. In such embodiment, the balloon material may have a melt temperature that is similar to the melt temperature of traditional balloon materials, but with greatly enhanced thermal conductivity. With such design, the enhanced thermal conductivity of the balloon material would allow for heat dissipation at such high rates that the balloon material stays below the melt temperature of the balloon material when in contact with plasma, thereby inhibiting holes from forming in the balloon material.

It is appreciated that the balloon 1304 can be formed from any suitable thermally conductive balloon materials. For example, in certain non-exclusive alternative embodiments, the balloon 1304 can be formed from one or more of graphite, aluminum nitride and/or boron nitride mixed with polydimethylsiloxane (PDMS), polyurethane, polymers such as PEBAX™, nylon and/or other suitable thermally conductive balloon materials.

FIG. 14 is a schematic cross-sectional view of a portion of the catheter system 1400 including yet another embodiment of the balloon integrity protection system 1442. As illustrated in FIG. 14, the catheter system 1400 can include a catheter 1402 including a catheter shaft 1410, a balloon assembly 1403 including a balloon 1404 having a balloon wall 1430 that defines a balloon interior 1446, a balloon proximal end 1404P, and a balloon distal end 1404D, and a balloon fluid 1432 that is retained substantially within the balloon interior 1446; and an energy guide 1422A including a plasma generator 1433 that is included and/or incorporated at a guide distal end 1422D of the energy guide 1422A. A guidewire lumen that would also likely be included in the catheter 1402 is not illustrated in FIG. 14. Additionally, as with the previous embodiments, the catheter system 1400, the catheter 1402 and/or the balloon assembly 1403 can further include the balloon integrity protection system 1442 that is operatively coupled to the balloon 1404 and that is configured to inhibit rupture or other damage to the balloon 1404 or otherwise protect the integrity of the balloon 1404 during use of the catheter system 1400. Alternatively, in other embodiments, the catheter system 1400 can include more components or fewer components than what is specifically illustrated and described herein. For example, certain components that were illustrated in FIG. 1, e.g., the guidewire 112, the light source 124, the power source 125, the system controller 126, the GUI 127, the handle assembly 128, the source manifold 136 and the fluid pump 138, are not specifically illustrated in FIG. 14 for purposes of clarity, but would likely be included in any embodiment of the catheter system 1400.

The catheter 1402, including the catheter shaft 1410, the balloon 1404, and the guidewire lumen, is generally similar in design and operation to what has been described in detail herein above. Thus, such components will not be described in detail again in relation to the embodiment shown in FIG. 14.

As above, the balloon 1404 is selectively movable between a deflated configuration suitable for advancing the catheter 1402 through a patient's vasculature, and an inflated configuration suitable for anchoring the catheter 1402 in position relative to the treatment site 106 (illustrated in FIG. 1). In some embodiments, the balloon proximal end 1404P can be coupled to the catheter shaft 1410, and the balloon distal end 1404D can also be coupled to the catheter shaft 1410. In other embodiments, the balloon distal end 1404D can be coupled to the guidewire lumen or another structure of the catheter 1402. Additionally, the balloon 1404 can be inflated with the balloon fluid 1432, e.g., from the fluid pump 138 (illustrated in FIG. 1), that is directed into the balloon interior 1446 of the balloon 1404 via the inflation conduit 140 (illustrated in FIG. 1).

However, in this embodiment, the balloon integrity protection system 1442 is somewhat different than in the previous embodiments. In particular, as shown in FIG. 14, the balloon integrity protection system 1442 includes modifications to the catheter shaft 1410 that are configured to better enable the plasma and/or the plasma generators 1433 to be maintained separated from the balloon 1404. More specifically, as illustrated in FIG. 14, the catheter shaft 1410 can include one or more of a shaft recess 1470 and at least one shaft projection 1472 (two shaft projections 1472 are illustrated in FIG. 14) such that the plasma generator 1433 can be positioned in a recessed manner relative to the balloon 1404.

In this embodiment, the shaft recess 1470 entails removing material from the catheter shaft 1410 and positioning the light guide 1422A such that the plasma generator 1433 is positioned substantially within the shaft recess 1470. With such design, the plasma generator 1433, and thus the plasma that is generated in the balloon fluid 1432 within the balloon interior 1446, is maintained a greater distance separated from the balloon 1404.

Additionally, as shown, the at least one shaft projection 1472 can be positioned along the catheter shaft 1410 and about the plasma generator 1433, e.g., about the shaft recess 1470, to better separate the plasma generator 1433, and thus the plasma that is generated in the balloon fluid 1432 within the balloon interior 1446, from at least certain portions of the balloon 1404.

It is appreciated that with an increased separation between the plasma generator 1433, and thus the plasma, from the balloon 1404, the balloon 1404 will be less susceptible to potential rupture or other damage due to the heat generated by the formation of the plasma in the balloon fluid 1432.

FIG. 15 is a schematic cross-sectional view of a portion of the catheter system 1500 including another embodiment of the balloon integrity protection system 1542. As illustrated in FIG. 15, the catheter system 1500 can include a catheter 1502 including a catheter shaft 1510, a balloon assembly 1503 including a balloon 1504 having a balloon wall 1530 that defines a balloon interior 1546, a balloon proximal end 1504P, and a balloon distal end 1504D, and a balloon fluid 1532 that is retained substantially within the balloon interior 1546; and at least one energy guide 1522A (two energy guides 1522A are illustrated in FIG. 15) including a plasma generator 1533 that is included and/or incorporated at a guide distal end 1522D of the energy guide 1522A. A guidewire lumen that would also likely be included in the catheter 1502 is not illustrated in FIG. 15. Additionally, as with the previous embodiments, the catheter system 1500, the catheter 1502 and/or the balloon assembly 1503 can further include the balloon integrity protection system 1542 that is operatively coupled to the balloon 1504 and that is configured to inhibit rupture or other damage to the balloon 1504 or otherwise protect the integrity of the balloon 1504 during use of the catheter system 1500. Alternatively, in other embodiments, the catheter system 1500 can include more components or fewer components than what is specifically illustrated and described herein. For example, certain components that were illustrated in FIG. 1, e.g., the guidewire 112, the light source 124, the power source 125, the system controller 126, the GUI 127, the handle assembly 128, the source manifold 136 and the fluid pump 138, are not specifically illustrated in FIG. 15 for purposes of clarity, but would likely be included in any embodiment of the catheter system 1500.

The catheter 1502, including the catheter shaft 1510, the balloon 1504, and the guidewire lumen, is generally similar in design and operation to what has been described in detail herein above. Thus, such components will not be described in detail again in relation to the embodiment shown in FIG. 15.

As above, the balloon 1504 is selectively movable between a deflated configuration suitable for advancing the catheter 1502 through a patient's vasculature, and an inflated configuration suitable for anchoring the catheter 1502 in position relative to the treatment site 106 (illustrated in FIG. 1). In some embodiments, the balloon proximal end 1504P can be coupled to the catheter shaft 1510, and the balloon distal end 1504D can also be coupled to the catheter shaft 1510. In other embodiments, the balloon distal end 1504D can be coupled to the guidewire lumen or another structure of the catheter 1502. Additionally, the balloon 1504 can be inflated with the balloon fluid 1532, e.g., from the fluid pump 138 (illustrated in FIG. 1), that is directed into the balloon interior 1546 of the balloon 1504 via the inflation conduit 140 (illustrated in FIG. 1).

However, in this embodiment, the balloon integrity protection system 1542 is somewhat different than in the previous embodiments. In particular, similar to the embodiment illustrated in FIG. 14, the balloon integrity protection system 1542 shown in FIG. 15 includes a shaft recess 1570 that is formed into the catheter shaft 1510, e.g., about a circumference of the catheter shaft 1510. With such design, the energy guides 1522A can be positioned within the shaft recess 1570 so that the energy guides 1522A are positioned with a greater separation distance relative to the balloon 1504.

Additionally, as also shown in FIG. 15, this embodiment of the balloon integrity protection system 1542 further includes a protection cage 1574 that is positioned about and/or fitted over the plasma generators 1533 to provide further separation between the plasma and the balloon 1504. The protection cage 1574 may serve to provide a recess and/or to further shift the catheter shaft 1510 away from the balloon 1504.

The protection cage 1574 can be formed from any suitable materials. For example, in certain non-exclusive alternative embodiments, the protection cage 1574 can be formed from one or more of a polymeric material, a metallic material (e.g., nitinol), or other suitable materials.

As with the previous embodiment, it is appreciated that with an increased separation between the plasma generator 1533, and thus the plasma, from the balloon 1504, the balloon 1504 will be less susceptible to potential rupture or other damage due to the heat generated by the formation of the plasma in the balloon fluid 1532.

Figure 16:
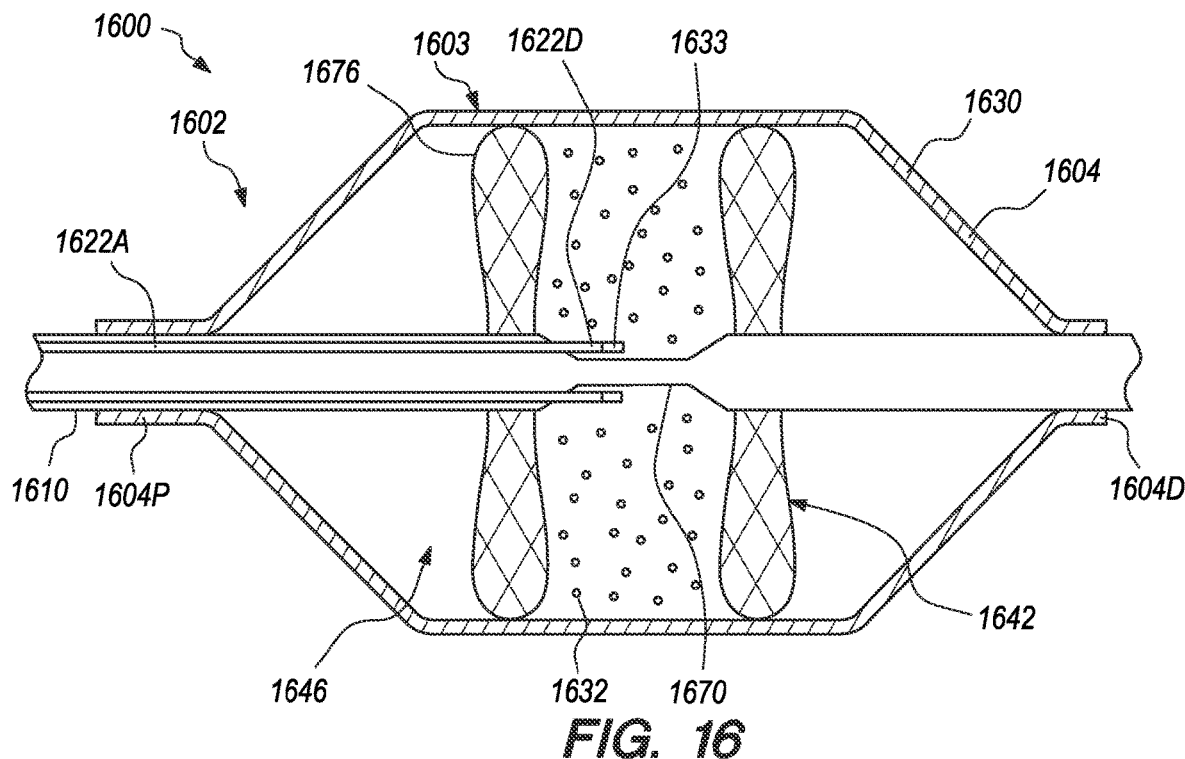
FIG. 16 is a schematic cross-sectional view of a portion of the catheter system including still another embodiment of the balloon integrity protection system.

FIG. 16 is a schematic cross-sectional view of a portion of the catheter system 1600 including still another embodiment of the balloon integrity protection system 1642. As illustrated in FIG. 16, the catheter system 1600 can include a catheter 1602 including a catheter shaft 1610, a balloon assembly 1603 including a balloon 1604 having a balloon wall 1630 that defines a balloon interior 1646, a balloon proximal end 1604P, and a balloon distal end 1604D, and a balloon fluid 1632 that is retained substantially within the balloon interior 1646; and at least one energy guide 1622A (two energy guides 1622A are illustrated in FIG. 16) including a plasma generator 1633 that is included and/or incorporated at a guide distal end 1622D of the energy guide 1622A. A guidewire lumen that would also likely be included in the catheter 1602 is not illustrated in FIG. 16. Additionally, as with the previous embodiments, the catheter system 1600, the catheter 1602 and/or the balloon assembly 1603 can further include the balloon integrity protection system 1642 that is operatively coupled to the balloon 1604 and that is configured to inhibit rupture or other damage to the balloon 1604 or otherwise protect the integrity of the balloon 1604 during use of the catheter system 1600. Alternatively, in other embodiments, the catheter system 1600 can include more components or fewer components than what is specifically illustrated and described herein. For example, certain components that were illustrated in FIG. 1, e.g., the guidewire 112, the light source 124, the power source 125, the system controller 126, the GUI 127, the handle assembly 128, the source manifold 136 and the fluid pump 138, are not specifically illustrated in FIG. 16 for purposes of clarity, but would likely be included in any embodiment of the catheter system 1600.

The catheter 1602, including the catheter shaft 1610, the balloon 1604, and the guidewire lumen, is generally similar in design and operation to what has been described in detail herein above. Thus, such components will not be described in detail again in relation to the embodiment shown in FIG. 16.

As above, the balloon 1604 is selectively movable between a deflated configuration suitable for advancing the catheter 1602 through a patient's vasculature, and an inflated configuration suitable for anchoring the catheter 1602 in position relative to the treatment site 106 (illustrated in FIG. 1). In some embodiments, the balloon proximal end 1604P can be coupled to the catheter shaft 1610, and the balloon distal end 1604D can also be coupled to the catheter shaft 1610. In other embodiments, the balloon distal end 1604D can be coupled to the guidewire lumen or another structure of the catheter 1602. Additionally, the balloon 1604 can be inflated with the balloon fluid 1632, e.g., from the fluid pump 138 (illustrated in FIG. 1), that is directed into the balloon interior 1646 of the balloon 1604 via the inflation conduit 140 (illustrated in FIG. 1).

However, in this embodiment, the balloon integrity protection system 1642 is somewhat different than in the previous embodiments. In particular, similar to the embodiments illustrated in FIGS. 14 and 15, the balloon integrity protection system 1642 shown in FIG. 16 includes a shaft recess 1670 that is formed into the catheter shaft 1610, e.g., about a circumference of the catheter shaft 1610. With such design, the energy guides 1622A can be positioned within the shaft recess 1670 so that the energy guides 1622A are positioned with a greater separation distance relative to the balloon 1604.

Additionally, in the embodiment illustrated in FIG. 16, the balloon integrity protection system 1642 further includes a pair of small, high-pressure separator balloons 1676 that, as shown, can be positioned about the catheter shaft 1610 at either end of the shaft recess 1670. The separator balloons 1676 are configured to, when inflated, extend substantially completely from the catheter shaft 1610 to the balloon wall 1630 of the balloon 1604, e.g., a traditional angioplasty balloon, on either side of the plasma generator 1633. With such design, the plasma that is generated in the balloon fluid 1632 within the balloon interior 1646 will be effectively restrained within the area between the separator balloons 1676. As such, the separator balloons 1676 effectively provide a recess for the plasma. Further, the separator balloons 1676 may additionally serve to shift the catheter shaft 1610 away from the wall of the blood vessel 108 (illustrated in FIG. 1) and hence away from the balloon 1604.

As noted herein, any additional separation between the plasma and the balloon 1604 can result in the balloon 1604 being less susceptible to potential rupture or other damage due to the heat generated by the formation of the plasma in the balloon fluid 1632.

Figure 17:
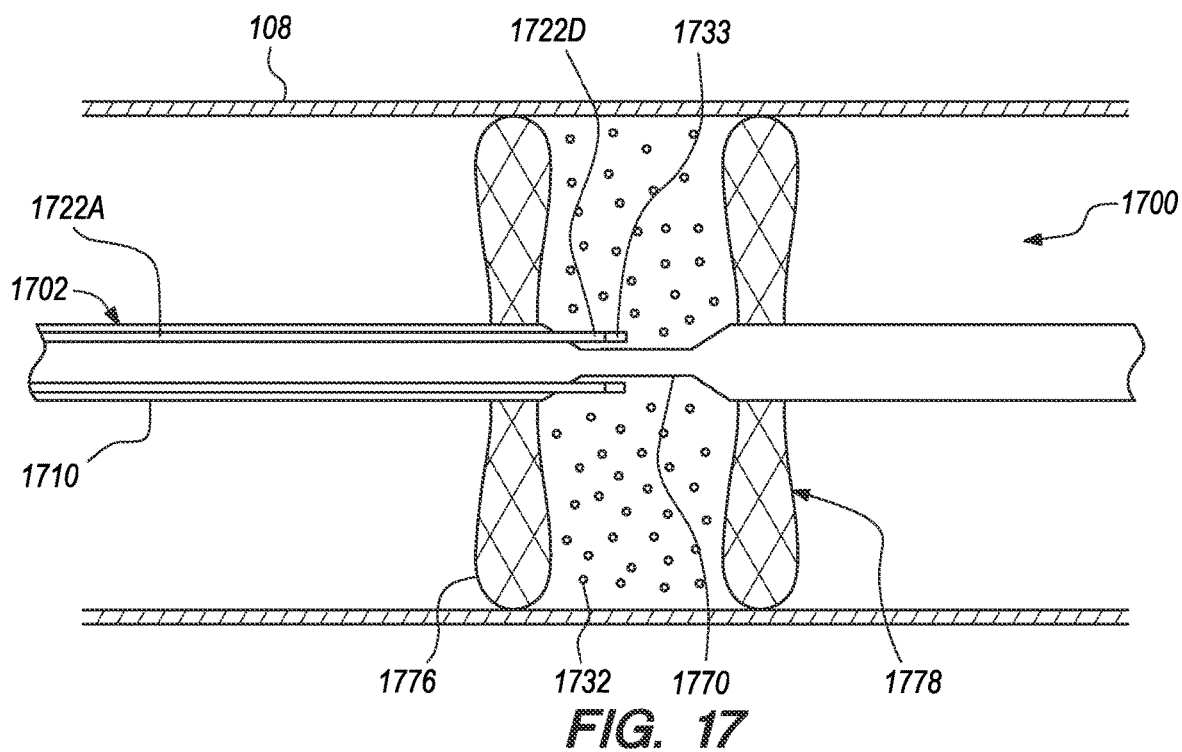
FIG. 17 is a schematic cross-sectional view of a portion of the catheter system including an embodiment of a vessel integrity protection system.

FIG. 17 is a schematic cross-sectional view of a portion of the catheter system 1700 including an embodiment of a vessel integrity protection system 1778. As illustrated in FIG. 17, the catheter system 1700 is somewhat similar to the embodiment illustrated in FIG. 16. However, in this embodiment, the catheter system 1700 does not include the balloon, and the catheter system 1700 is simply positioned within the blood vessel 108 without the traditional angioplasty balloon. More particularly, as shown in this embodiment, the catheter system 1700 can include a catheter 1702 including a catheter shaft 1710; and at least one energy guide 1722A (two energy guides 1722A are illustrated in FIG. 17) including a plasma generator 1733 that is included and/or incorporated at a guide distal end 1722D of the energy guide 1722A. A guidewire lumen that would also likely be included in the catheter 1702 is not illustrated in FIG. 17. Additionally, the catheter system 1700 and/or the catheter 1702 can further include the vessel integrity protection system 1778 that is configured protect the integrity of the blood vessel 108 during use of the catheter system 1700. Alternatively, in other embodiments, the catheter system 1700 can include more components or fewer components than what is specifically illustrated and described herein. For example, certain components that were illustrated in FIG. 1, e.g., the guidewire 112, the light source 124, the power source 125, the system controller 126, the GUI 127, the handle assembly 128, the source manifold 136 and the fluid pump 138, are not specifically illustrated in FIG. 17 for purposes of clarity, but would likely be included in any embodiment of the catheter system 1700.

The catheter 1702, including the catheter shaft 1710, and the guidewire lumen, is generally similar in design and operation to what has been described in detail herein above. Thus, such components will not be described in detail again in relation to the embodiment shown in FIG. 17.

Additionally, the balloon fluid 1732, e.g., from the fluid pump 138 (illustrated in FIG. 1), can be directed into the blood vessel via the inflation conduit 140 (illustrated in FIG. 1).

As illustrated in this embodiment, the vessel integrity protection system 1778 is substantially similar to the balloon integrity protection system 1642 illustrated and described in relation to FIG. 16. For example, as shown in FIG. 17, the vessel integrity protection system 1778 includes a shaft recess 1770 and a pair of small, high-pressure separator balloons 1776. Alternatively, the vessel integrity protection system 1778 can include more components or fewer components than those specifically illustrated in FIG. 17.

As shown, the shaft recess 1770 is again formed into the catheter shaft 1710, e.g., about a circumference of the catheter shaft 1710. With such design, the energy guides 1722A can be positioned within the shaft recess 1770 so that the energy guides 1722A are positioned with a greater separation distance relative to the blood vessel 108.

Additionally, in this embodiment, the separator balloons 1776 are again positioned about the catheter shaft 1710 at either end of the shaft recess 1770. The separator balloons 1776 are configured to, when inflated, extend substantially completely from the catheter shaft 1710 to the wall of the blood vessel 108 on either side of the plasma generator 1733. With such design, the plasma that is generated in the balloon fluid 1732 will be effectively restrained within the area between the separator balloons 1776. As such, the separator balloons 1776 effectively provide a recess for the plasma and further provide a seal against the wall of the blood vessel 108 creating a volume to perform intravascular lithotripsy. Thus, the plasma and the resulting pressure waves can be more restricted to be directed toward intravascular lesions to be treated.

Further, the separator balloons 1776 may additionally serve to shift the catheter shaft 1710 away from the wall of the blood vessel 108. It is appreciated that any additional separation between the plasma and the wall of the blood vessel 108 will help protect the blood vessel 108 from being potentially damaged by the plasma.

Figure 18:
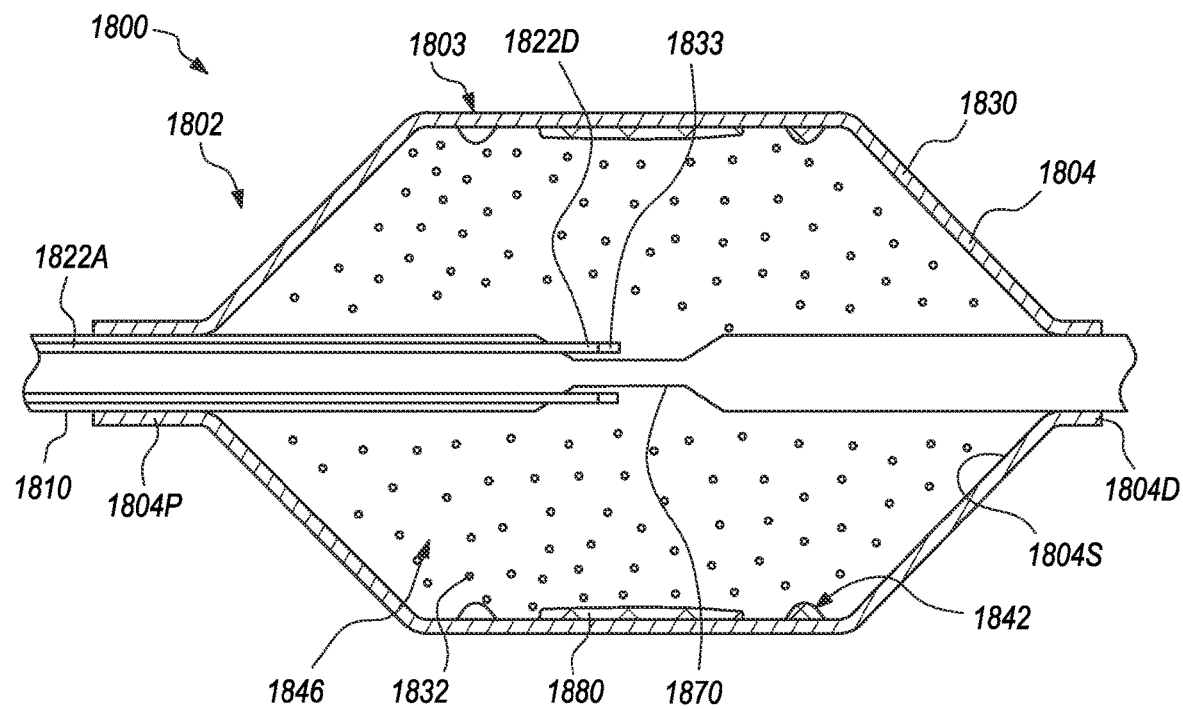
FIG. 18 is a schematic cross-sectional view of a portion of the catheter system including yet another embodiment of the balloon integrity protection system.

FIG. 18 is a schematic cross-sectional view of a portion of the catheter system 1800 including yet another embodiment of the balloon integrity protection system 1842. As illustrated in FIG. 18, the catheter system 1800 can include a catheter 1802 including a catheter shaft 1810, a balloon assembly 1803 including a balloon 1804 having a balloon wall 1830 that defines a balloon interior 1846, a balloon proximal end 1804P, and a balloon distal end 1804D, and a balloon fluid 1832 that is retained substantially within the balloon interior 1846; and at least one energy guide 1822A (two energy guides 1822A are illustrated in FIG. 18) including a plasma generator 1833 that is included and/or incorporated at a guide distal end 1822D of the energy guide 1822A. A guidewire lumen that would also likely be included in the catheter 1802 is not illustrated in FIG. 18. Additionally, as with the previous embodiments, the catheter system 1800, the catheter 1802 and/or the balloon assembly 1803 can further include the balloon integrity protection system 1842 that is operatively coupled to the balloon 1804 and that is configured to inhibit rupture or other damage to the balloon 1804 or otherwise protect the integrity of the balloon 1804 during use of the catheter system 1800. Alternatively, in other embodiments, the catheter system 1800 can include more components or fewer components than what is specifically illustrated and described herein. For example, certain components that were illustrated in FIG. 1, e.g., the guidewire 112, the light source 124, the power source 125, the system controller 126, the GUI 127, the handle assembly 128, the source manifold 136 and the fluid pump 138, are not specifically illustrated in FIG. 18 for purposes of clarity, but would likely be included in any embodiment of the catheter system 1800.

The catheter 1802, including the catheter shaft 1810, the balloon 1804, and the guidewire lumen, is generally similar in design and operation to what has been described in detail herein above. Thus, such components will not be described in detail again in relation to the embodiment shown in FIG. 18.

As above, the balloon 1804 is selectively movable between a deflated configuration suitable for advancing the catheter 1802 through a patient's vasculature, and an inflated configuration suitable for anchoring the catheter 1802 in position relative to the treatment site 106 (illustrated in FIG. 1). In some embodiments, the balloon proximal end 1804P can be coupled to the catheter shaft 1810, and the balloon distal end 1804D can also be coupled to the catheter shaft 1810. In other embodiments, the balloon distal end 1804D can be coupled to the guidewire lumen or another structure of the catheter 1802. Additionally, the balloon 1804 can be inflated with the balloon fluid 1832, e.g., from the fluid pump 138 (illustrated in FIG. 1), that is directed into the balloon interior 1846 of the balloon 1804 via the inflation conduit 140 (illustrated in FIG. 1).

However, in this embodiment, the balloon integrity protection system 1842 is somewhat different than in the previous embodiments. In particular, similar to the embodiments illustrated in FIGS. 14-16, the balloon integrity protection system 1842 shown in FIG. 18 includes a shaft recess 1870 that is formed into the catheter shaft 1810, e.g., about a circumference of the catheter shaft 1810. With such design, the energy guides 1822A can be positioned within the shaft recess 1870 so that the energy guides 1822A are positioned with a greater separation distance relative to the balloon 1804.

Additionally, in the embodiment illustrated in FIG. 18, the balloon integrity protection system 1842 further includes one or more raised features 1880 that can formed and/or molded onto a surface 1804S of the balloon 1804, e.g., an inner surface of the balloon 1804. More particularly, the one or more raised features 1880 can be provided in the form of ribs (circumferential raised features) and/or splines (axial raised features) that are formed and/or molded onto the surface 1804S of the balloon 1804. In certain embodiments, the raised features 1880 can be aligned, at least generally, with the plasma generators 1833 in order to provide maximum separation between the balloon wall 1830 and the plasma that is generated in the balloon fluid 1832 within the balloon interior 1846.

The material for the raised features 1880 can be varied to suit the specific requirements of the catheter system 1800, the balloon assembly 1803 and/or the balloon integrity protection system 1842. For example, in certain non-exclusive alternative embodiments, the raised features 1880 can be formed from standard balloon materials such as polydimethylsiloxane (PDMS), polyurethane, polymers such as PEBAX™ or nylon. Still alternatively, the raised features 1880 can be formed from one or more of Nitinol, stainless steel, carbon, aramid, rayon, polyester, nylon, and natural (silk, wool, cotton and linen) fibers, Polyacetylene, polypyrrole, polyindole, polyaniline, poly(p-phenylene vinylene), poly(thiophene), poly(3,4-ethylenedioxythiophene), poly(p-phenylene sulfide), or other suitable materials.

As noted herein, any additional separation between the plasma and the balloon 1804 can result in the balloon 1804 being less susceptible to potential rupture or other damage due to the heat generated by the formation of the plasma in the balloon fluid 1832.

Figure 19:
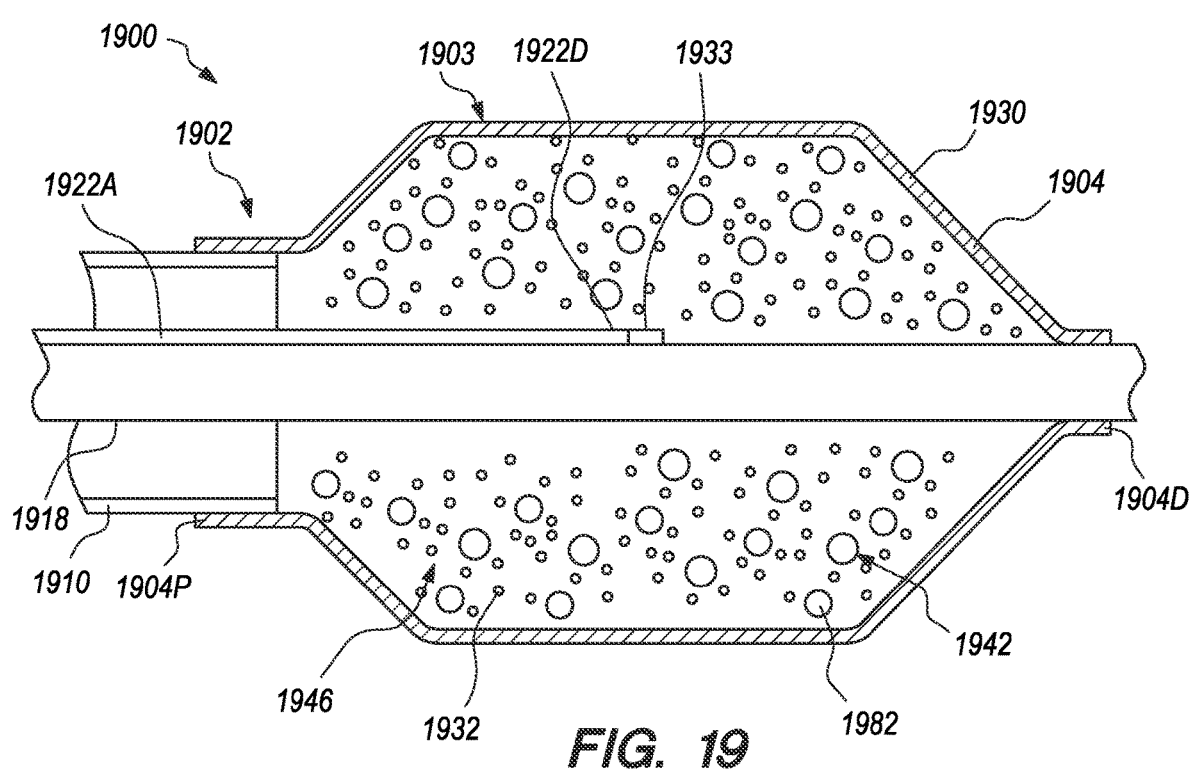
FIG. 19 is a schematic cross-sectional view of a portion of the catheter system including another embodiment of the balloon integrity protection system.

FIG. 19 is a schematic cross-sectional view of a portion of the catheter system 1900 including another embodiment of the balloon integrity protection system 1942. As with the previous embodiments, as illustrated in FIG. 19, the catheter system 1900 can include a catheter 1902 including a catheter shaft 1910, a balloon assembly 1903 including a balloon 1904 having a balloon wall 1930 that defines a balloon interior 1946, a balloon proximal end 1904P, and a balloon distal end 1904D, a balloon fluid 1932 that is retained substantially within the balloon interior 1946, and a guidewire lumen 1918 that extends into and runs through the balloon interior 1946; and an energy guide 1922A including a plasma generator 1933 that is included and/or incorporated at a guide distal end 1922D of the energy guide 1922A. Additionally, as with the previous embodiments, the catheter system 1900, the catheter 1902 and/or the balloon assembly 1903 can further include the balloon integrity protection system 1942 that is operatively coupled to the balloon 1904 and that is configured to inhibit rupture or other damage to the balloon 1904 or otherwise protect the integrity of the balloon 1904 during use of the catheter system 1900. Alternatively, in other embodiments, the catheter system 1900 can include more components or fewer components than what is specifically illustrated and described herein. For example, certain components that were illustrated in FIG. 1, e.g., the guidewire 112, the light source 124, the power source 125, the system controller 126, the GUI 127, the handle assembly 128, the source manifold 136 and the fluid pump 138, are not specifically illustrated in FIG. 19 for purposes of clarity, but would likely be included in any embodiment of the catheter system 1900.

The catheter 1902, including the catheter shaft 1910, the balloon 1904, and the guidewire lumen 1918, is generally similar in design and operation to what has been described in detail herein above. Thus, such components will not be described in detail again in relation to the embodiment shown in FIG. 19.

As above, the balloon 1904 is selectively movable between a deflated configuration suitable for advancing the catheter 1902 through a patient's vasculature, and an inflated configuration suitable for anchoring the catheter 1902 in position relative to the treatment site 106 (illustrated in FIG. 1). In some embodiments, the balloon proximal end 1904P can be coupled to the catheter shaft 1910, and the balloon distal end 1904D can be coupled to the guidewire lumen 1918. In other embodiments, the catheter shaft 1910 can extend fully through the balloon 1904, and the balloon distal end 1904D can also be coupled to the catheter shaft 1910. In still other embodiments, the balloon distal end 1904D can be coupled to another structure of the catheter 1902. Additionally, the balloon 1904 can be inflated with the balloon fluid 1932, e.g., from the fluid pump 138 (illustrated in FIG. 1), that is directed into the balloon interior 1946 of the balloon 1904 via the inflation conduit 140 (illustrated in FIG. 1).

However, in this embodiment, the balloon integrity protection system 1942 is somewhat different than in the previous embodiments. In particular, as shown in FIG. 19, the balloon integrity protection system 1942 includes leak plugging material 1982 (also sometimes referred to as "self-healing material") that can be distributed within the balloon interior 1946 in addition to the balloon fluid 1932. For example, in certain embodiments, during catheter assembly, the balloon 1904 can be loaded with an assortment of leak plugging material 1982 in the form of "corks" or beads that during in-vivo inflation with the balloon fluid 1932 disperse within the balloon 1904.

During use of the catheter system 1900, if the plasma melts a hole in the balloon wall 1930, the leak plugging material 1982 will migrate through the hole to plug the leak in order to inhibit propagation of the holes and/or rupture of the balloon 1904. It is appreciated that the leak plugging material 1982 can be formed to be any suitable size in order to effectively plug any holes that may develop in the balloon wall 1930 during use of the catheter system 1900. For example, in certain embodiments, the leak plugging material 1982 can be provided in the form of "corks" or beads that are between approximately one μm and 100 μm in diameter. More particularly, in some such embodiments, the leak plugging material 1982 can be provided in the form of "corks" or beads that are approximately 1 μm, 2 μm, 5 μm, 7 μm, 10 μm, 15 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 95 μm, or 100 μm in diameter. Alternatively, the leak plugging material 1982 can be provided in the form of "corks" or beads that are greater than 100 μm or less than one μm in diameter.

Additionally, the leak plugging material 1982 can be formed from any suitable materials. For example, in alternative embodiments, the leak plugging material 1982 can be non-absorbable or bio-absorbable. It is appreciated that bio-absorbable material has the advantage that such leak plugging material 1982 smaller than the hole size that escape the balloon 1904 before being plugged will metabolize within the microvascular before causing blockage that could lead to ischemia. Further, in certain non-exclusive alternative embodiments, the leak plugging material 1982 can be formed from gelatin, collagen, fibrin, polylactic acid, polyglycolic acid, poly(lactic-co-glycolic) acid, and polycaprolactone or other suitable materials used in closure devices.

Figure 20:
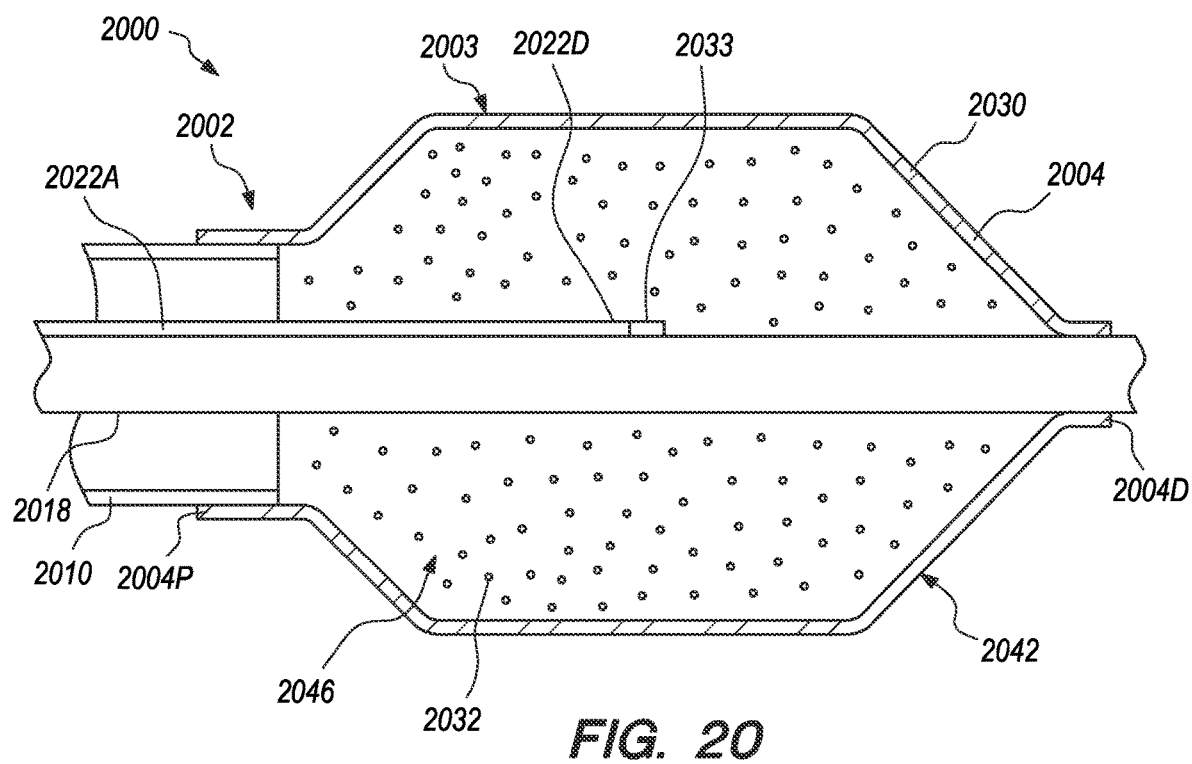
FIG. 20 is a schematic cross-sectional view of a portion of the catheter system including still yet another embodiment of the balloon integrity protection system.

FIG. 20 is a schematic cross-sectional view of a portion of the catheter system 2000 including still yet another embodiment of the balloon integrity protection system 2042. As with the previous embodiments, as illustrated in FIG. 20, the catheter system 2000 can include a catheter 2002 including a catheter shaft 2010, a balloon assembly 2003 including a balloon 2004 having a balloon wall 2030 that defines a balloon interior 2046, a balloon proximal end 2004P, and a balloon distal end 2004D, a balloon fluid 2032 that is retained substantially within the balloon interior 2046, and a guidewire lumen 2018 that extends into and runs through the balloon interior 2046; and an energy guide 2022A including a plasma generator 2033 that is included and/or incorporated at a guide distal end 2022D of the energy guide 2022A. Additionally, as with the previous embodiments, the catheter system 2000, the catheter 2002 and/or the balloon assembly 2003 can further include the balloon integrity protection system 2042 that is operatively coupled to the balloon 2004 and that is configured to inhibit rupture or other damage to the balloon 2004 or otherwise protect the integrity of the balloon 2004 during use of the catheter system 2000. Alternatively, in other embodiments, the catheter system 2000 can include more components or fewer components than what is specifically illustrated and described herein. For example, certain components that were illustrated in FIG. 1, e.g., the guidewire 112, the light source 124, the power source 125, the system controller 126, the GUI 127, the handle assembly 128, the source manifold 136 and the fluid pump 138, are not specifically illustrated in FIG. 20 for purposes of clarity, but would likely be included in any embodiment of the catheter system 2000.

The catheter 2002, including the catheter shaft 2010, the balloon 2004, and the guidewire lumen 2018, is generally similar in design and operation to what has been described in detail herein above. Thus, such components will not be described in detail again in relation to the embodiment shown in FIG. 20.

As above, the balloon 2004 is selectively movable between a deflated configuration suitable for advancing the catheter 2002 through a patient's vasculature, and an inflated configuration suitable for anchoring the catheter 2002 in position relative to the treatment site 106 (illustrated in FIG. 1). In some embodiments, the balloon proximal end 2004P can be coupled to the catheter shaft 2010, and the balloon distal end 2004D can be coupled to the guidewire lumen 2018. In other embodiments, the catheter shaft 2010 can extend fully through the balloon 2004, and the balloon distal end 2004D can also be coupled to the catheter shaft 2010. In still other embodiments, the balloon distal end 2004D can be coupled to another structure of the catheter 2002. Additionally, the balloon 2004 can be inflated with the balloon fluid 2032, e.g., from the fluid pump 138 (illustrated in FIG. 1), that is directed into the balloon interior 2046 of the balloon 2004 via the inflation conduit 140 (illustrated in FIG. 1).

However, in this embodiment, the balloon integrity protection system 2042 is somewhat different than in the previous embodiments. In particular, as shown in FIG. 20, the balloon integrity protection system 2042 includes the balloon 2004 being optically opaque, i.e. to the wavelength of light energy from the light source 124 (illustrated in FIG. 1). With such design, any potential stray light, e.g., potential stray laser light, within the balloon interior 2046 is inhibited from being able escape from the balloon interior 2046 for purposes of protecting the user or patient from any vascular damage that may otherwise occur due to the presence of such stray light.

It should be noted that, as used in this specification and the appended claims, the singular forms "a," "an," and "the" include plural referents unless the content and/or context clearly dictates otherwise. It should also be noted that the term "or" is generally employed in its sense including "and/or" unless the content or context clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

The headings used herein are provided for consistency with suggestions under 37 CFR 1.77 or otherwise to provide organizational cues. These headings shall not be viewed to limit or characterize the invention(s) set out in any claims that may issue from this disclosure. As an example, a description of a technology in the "Background" is not an admission that technology is prior art to any invention(s) in this disclosure. Neither is the "Summary" or "Abstract" to be considered as a characterization of the invention(s) set forth in issued claims.

The embodiments described herein are not intended to be exhaustive or to limit the invention to the precise forms disclosed in the present detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

It is understood that although a number of different embodiments of the catheter systems have been illustrated and described herein, one or more features of any one embodiment can be combined with one or more features of one or more of the other embodiments, provided that such combination satisfies the intent of the present invention.

While a number of exemplary aspects and embodiments of the catheter systems have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope, and no limitations are intended to the details of construction or design herein shown.

What is claimed is:

1. A catheter system for treating a treatment site within or adjacent to a vessel wall of a blood vessel, or a heart valve, the catheter system comprising:
    an energy source that generates energy;
    a catheter shaft that extends into the blood vessel, the catheter shaft including a shaft recess;
    an energy guide that is configured to receive energy from the energy source and guide the energy into the blood vessel; and
    a plasma generator that is positioned at a guide distal end of the energy guide, the plasma generator being configured to generate the plasma in a fluid within the blood vessel; and
    wherein the energy guide is positioned such that the plasma generator is positioned substantially within the shaft recess.

2. The catheter system of claim 1 further including a balloon that is positionable substantially adjacent to the treatment site, the balloon having a balloon wall that defines a balloon interior, the balloon being configured to retain a balloon fluid within the balloon interior.

3. The catheter system of claim 2 further comprising a pair of separator balloons that are positioned about the catheter shaft at either end of the shaft recess.

4. The catheter system of claim 2 wherein the plasma formation causes rapid bubble formation and imparts pressure waves upon the balloon wall adjacent to the treatment site.

5. The catheter system of claim 2 wherein the energy source is a laser source that provides pulses of laser energy, and the energy guide includes an optical fiber.

6. The catheter system of claim 2 wherein the energy source is a high voltage energy source that provides pulses of high voltage.

7. The catheter system of claim 2 wherein a composite material is positioned on a surface of the balloon.

8. The catheter system of claim 2 wherein the balloon is formed from thermally conductive balloon material.

9. The catheter system of claim 2 wherein the balloon is optically opaque.

10. The catheter system of claim 2 further comprising a balloon integrity protection system that is operatively coupled to the balloon, the balloon integrity protection system being configured to inhibit rupture of the balloon due to the plasma formed in the balloon fluid within the balloon interior during use of the catheter system.

11. A catheter system for treating a treatment site within or adjacent to a vessel wall or a heart valve, the catheter system comprising:
    an energy source that generates pulses of energy;
    a balloon that is positionable substantially adjacent to the treatment site, the balloon having a balloon wall that defines a balloon interior, the balloon being configured to retain a balloon fluid within the balloon interior;
    a catheter shaft that extends into the balloon interior, the balloon being coupled to the catheter shaft, the catheter shaft including a shaft recess;
    an energy guide that is configured to receive the energy from the energy source and guide the energy into the balloon interior so that plasma is formed in the balloon fluid within the balloon interior;
    a plasma generator that is positioned at a guide distal end of the energy guide, the plasma generator being configured to generate the plasma, the energy guide being positioned so that the plasma generator is positioned substantially within the shaft recess; and
    a balloon integrity protection system that is operatively coupled to the balloon, the balloon integrity protection system being configured to inhibit temperature-induced rupture of the balloon due to the plasma formed in the balloon fluid within the balloon interior during use of the catheter system.

12. The catheter system of claim 11 wherein the plasma formation causes rapid bubble formation and imparts pressure waves upon the balloon wall adjacent to the treatment site.

13. The catheter system of claim 11 wherein the energy source is a laser source that provides pulses of laser energy.

14. The catheter system of claim 13 wherein the energy guide includes an optical fiber.

15. The catheter system of claim 11 wherein the energy source is a high voltage energy source that provides pulses of high voltage.

16. The catheter system of claim 15 wherein the energy guide includes an electrode pair including spaced apart electrodes that extend into the balloon interior; and wherein pulses of high voltage from the energy source are applied to the electrodes and form an electrical arc across the electrodes.

17. The catheter system of claim 11 wherein the balloon integrity protection system includes a second balloon that is positioned to substantially encircle the balloon, the second balloon including a second balloon wall that is positioned such that a majority of the second balloon wall is positioned spaced apart from the balloon wall.

18. The catheter system of claim 11 wherein the balloon integrity protection system includes a second balloon that is positioned to substantially encircle the balloon, the second balloon including a second balloon wall that is positioned such that the second balloon wall is positioned substantially directly adjacent to the balloon wall.

19. The catheter system of claim 11 wherein the balloon integrity protection system includes a composite material that is positioned on a surface of the balloon.

20. The catheter system of claim 11 wherein the balloon integrity protection system includes a braided material layer that is wrapped around a surface of the balloon to provide a braided balloon composite.

21. The catheter system of claim 11 wherein the balloon is formed as an electro-spun balloon.

22. The catheter system of claim 11 wherein the balloon is formed from electrically conductive balloon material.

23. The catheter system of claim 11 wherein the balloon is formed from thermally conductive balloon material.

24. The catheter system of claim 11 wherein the balloon integrity protection system includes a leak plugging material that is distributed within the balloon interior, the leak plugging material being configured to plug leaks in the balloon that may develop during use of the catheter system.

25. The catheter system of claim 11 wherein the balloon integrity protection system includes the balloon being optically opaque.

26. The catheter system of claim 11 wherein the balloon includes a drug-eluting coating.

* * * * *